(12) United States Patent
Woiwode et al.

(10) Patent No.: US 10,561,638 B2
(45) Date of Patent: Feb. 18, 2020

(54) METHODS FOR TREATING DEPENDENCE

(71) Applicant: Biotie Therapies, Inc., Ardsley, NY (US)

(72) Inventors: Tom Woiwode, South San Francisco, CA (US); Mark Moran, South San Francisco, CA (US); Lesley Pickford, South San Francisco, CA (US)

(73) Assignee: Biotie Therapies, Inc., Ardsley, NY (US)

( * ) Notice: Subject to any disclaimer, the term of this patent is extended or adjusted under 35 U.S.C. 154(b) by 0 days.

(21) Appl. No.: 14/099,882

(22) Filed: Dec. 6, 2013

(65) Prior Publication Data
US 2014/0099336 A1  Apr. 10, 2014

Related U.S. Application Data

(63) Continuation of application No. 12/187,166, filed on Aug. 6, 2008, now abandoned.

(60) Provisional application No. 60/935,323, filed on Aug. 6, 2007, provisional application No. 60/956,555, filed on Aug. 17, 2007, provisional application No. 60/960,591, filed on Oct. 4, 2007.

(51) Int. Cl.
| | | |
|---|---|---|
| *A61K 31/4164* | (2006.01) | |
| *A61K 45/06* | (2006.01) | |
| *A61K 9/08* | (2006.01) | |
| *A61K 31/415* | (2006.01) | |
| *A61K 31/417* | (2006.01) | |

(52) U.S. Cl.
CPC ............ *A61K 31/4164* (2013.01); *A61K 9/08* (2013.01); *A61K 31/415* (2013.01); *A61K 31/417* (2013.01); *A61K 45/06* (2013.01)

(58) Field of Classification Search
CPC .............. A61K 31/415; A61K 31/4164; A61K 31/417; A61K 45/06; A61K 9/08
See application file for complete search history.

(56) References Cited

U.S. PATENT DOCUMENTS

| | | | |
|---|---|---|---|
| 5,958,896 A | 9/1999 | Renshaw et al. | |
| 6,593,367 B1 | 7/2003 | Dewey et al. | |
| 2003/0040015 A1 | 2/2003 | Kim et al. | |
| 2006/0058336 A1 | 3/2006 | Nakinishi et al. | |
| 2009/0054403 A1* | 2/2009 | Woiwode et al. | 514/214.02 |
| 2009/0054414 A1* | 2/2009 | Woiwode et al. | 514/221 |
| 2009/0082341 A1* | 3/2009 | Woiwode et al. | 514/221 |
| 2010/0105748 A1 | 4/2010 | Weinshenker et al. | |

FOREIGN PATENT DOCUMENTS

| | | |
|---|---|---|
| AU | 2008283903 | 1/2014 |
| CN | 106983747 | 7/2017 |
| EP | 2218804 A4 | 8/2011 |
| EP | 3251670 | 12/2017 |
| JP | 03-500411 A | 1/1991 |
| JP | 2000-506832 A | 6/2000 |
| JP | 2014-148551 A | 8/2014 |
| RU | 2252756 C1 | 5/2005 |
| RU | 2279871 C2 | 7/2006 |
| RU | 2300378 C2 | 6/2007 |
| WO | 2009/021055 A1 | 2/2009 |

OTHER PUBLICATIONS

Whitworth et al., "Comparison of acamprosate and placebo in long-term treatment of alcohol dependence," The Lancet (1996) vol. 347, pp. 1438-1442.*
Köhnke et al., "A Genotype-Controlled Analysis of Plasma Dopamine β-Hydroxylase in Healthy and Alcohol Subjects: Evidence for Alcohol-Related Differences in Noradrenergic Function," Biol. Psychiatry, 2002; 52: 1151-1158.*
Chinese Third Office Action, Chinese Application No. 200880109939. 4, dated Mar. 25, 2014, 12 pages.
Mexican Office Action, Mexican Application No. 10/001390, dated Feb. 27, 2014, 4 pages.
Singapore Office Action (Search and Examination Report), Singapore Patent Application No. 201000486-9, dated May 13, 2011, 17 pages.
Remington: The Science and Practice of Pharmacy, $19^{th}$ ed., vol. II., Mack Publishings Co., Pennsylvania, USA (1995) (Chapter 92, pp. 1615-1649).
Carroll et al., "Efficacy of Disulfiram and Cognitive Behavior Therapy in Cocaine-Dependent Outpatients," Arch. Gen. Psychiatry, Mar. 2004, pp. 264-272, vol. 61.
Nich, C. et al., "Sex differences in cocaine-dependent individuals' response to disulfiram treatment", Addictive Behaviors, 2004, vol. 29, pp. 1123-1128.
PCT International Search Report and Written Opinion, PCT/US 08/72357, dated Nov. 14, 2008, 12 pages.
Cubells, J.F. et al., "A Haplotype at the DBH Locus, Associated with Low Plasma Dopamine β-Hydroxylase Activity, Also Associates with Cocaine-Induced Paranoia," Molecular Psychiatry, Jan. 2000, pp. 56-63, vol. 5, No. 1.
European Extended Search Report, European Application No. 08797300. 4, dated Nov. 24, 2010, 6 pages.
New Zealand Examination Report, New Zealand Application No. 583192, dated Nov. 10, 2010, 2 pages.
Petrakis, I.L. et al., "Disulfiram Treatment for Cocaine Dependence in Methadone-Maintained Opioid Addicts," Addiction, Feb. 2000, pp. 219-228, vol. 95, No. 2.

(Continued)

*Primary Examiner* — Sahar Javanmard
(74) *Attorney, Agent, or Firm* — Kilpatrick Townsend & Stockton LLP

(57) ABSTRACT

Provided are methods of treating patients suffering from or susceptible to at least one symptom of abuse of, dependence on, or withdrawal from at least one substance with Compound A. Also provided are methods of treating at least one phase of substance dependence on at least one substance in patients and certain methods of treating at least one phase of cocaine dependence in patients.

9 Claims, 11 Drawing Sheets

(56) References Cited

OTHER PUBLICATIONS

Philippine Office Action, Philippine Application No. 12010500230, dated Feb. 23, 2011, 1 page.
Stanley, W.C. et al., "Catecholamine Modulatory Effects of Nepicastat (RS-25560-197), a Novel, Potent and Selective Inhibitor of Dopamine-β-Hydroxylase," British Journal of Pharmacology, 1997, pp. 1803-1809, vol. 121, No. 8.
Australian Office Action, Australian Application No. 2008283903, dated Dec. 21, 2012, 5 pages.
Beliaev, A. et al., "Synthesis and Biological Evaluation of Novel, Peripherally Selective Chromanyl Imidazolethione-Based Inhibitors of Dopamine β-Hydroxylase," J. Med. Chem., 2006, pp. 1191-1197, vol. 49.
Canadian Office Action, Canadian Application No. 2,695,372, dated Feb. 7, 2012, 5 pages.
Chinese First Office Action, Chinese Application No. 200880109939.4, dated Aug. 20, 2012, 18 pages.
Chinese Second Office Action, Chinese Application No. 200880109939.4, dated Jul. 9, 2013, 11 pages.
Israel Notification Prior to Examination of Patent Application No. 203722, Israel Application No. 203722, dated Jul. 12, 2012, 3 pages.
Israel Notification of Defects in Patent Application No. 203722, Israel Application No. 203722, dated Apr. 2, 2013, 2 pages.
English Version of Japanese First Office Action, Japanese Application No. 2010-520285, dated May 7, 2013, 2 pages.
Kosten, T.R., "Advances in the Pharmacotherapy of Stimulant Dependence: From Alcohol Antagonists to Xenova Vaccines," Clinical Neuroscience Research, 2005, pp. 169-173. vol. 5.
Kuran, W., "Dopamine Agonists—Clinical Applications beyond Parkinson's Disease," Neurol. Neurochir. Pol., Mar.-Apr. 2007;41(2 Suppl 1):S54-8 (English abstract only).
"The Merck Manual of Diagnosis and Therapy" Moscow: Mir, 1997, vol. 2, p. 23, entry "Cocaine Type Dependence"), reprint of The Merck Manual Copyright 1992 by Merck & Co., Inc., Whitehouse Station, New Jersey, U.S.A.
O'Brien, "Pharmacotherapy in Narcology" [online] [retrieved on Mar. 29, 2012] (retrieved from the Internet on <URL:narcom.ru/publ/info/918) , entries "Pharmacological Aspects of Cocaine Use" and "Medication Treatment."
Philippine Office Action, Philippine Application No. 1/2010/500230, dated Jul. 24, 2013, 1 page.
Russian Office Action, Russian Application No. 2010108249/21(011617), dated Apr. 29, 2012, 4 pages.
Russian Decision to Grant, Russian Application No. 2010108249/21(011617), dated Apr. 25, 2013, 5 pages.
United States Office Action, U.S. Appl. No. 12/187,166, dated Jun. 6, 2013, 17 pages.
United States Office Action, U.S. Appl. No. 12/187,166, dated Mar. 1, 2012, 16 pages.
United States Office Action, U.S. Appl. No. 12/187,166, dated May 31, 2011, 18 pages.
Mexican Office Action, Mexican Application No. 10/001390, dated Oct. 17, 2013, 4 pages.
European Examination Report, European Application No. 08797300.4, dated Feb. 21, 2014, 5 pages.
Japanese Office Action, Japanese Application No. 2010-520285, dated Feb. 4, 2014, 4 pages.
Philippine Application No. 1/2010/500230, Subsequent Substantive Examination Report, dated Dec. 3, 2015, 1 page.
Chinese Application No. 200880109939.4, Reexamination Notice, dated Feb. 4, 2016, 17 pages.
Japanese Application No. 2014-107381, Office Action dated Feb. 23, 2016, 6 pages.
AU2014202047, "Examination Report", dated Jul. 31, 2015, 6 pages.
CN200880109939.4 , "Office Action", dated Sep. 12, 2014, 15 pages.
IL203722 , "Office Action", dated Jun. 12, 2014, 2 pages.
IL203722 , "Office Action", dated Aug. 19, 2015, 3 pages.
JP2014-107381 , "Office Action", dated May 12, 2015, 4 pages.
MX/A/2010/001390 , "Office Action", dated Jul. 8, 2014, 2 pages.
MX/A/2010/001390 , "Office Action", dated Feb. 16, 2015, 6 pages.
IN1066/chenp/2010, Examination Report, dated Nov. 12, 2015, 3 pages.
Colombo, et al., "The Dopamine β-Hydroxylase Inhibitor, Nepicastat, Reduces Different Alcohol-Related Behaviors in Rats," Alcoholism: Clinical and Experimental Research, vol. 38, No. 9, Sep. 2014.
PH1-2015-502210, "Office Action", dated Aug. 5, 2016, 2 pages.
Gaval-Cruz, et al., "Mechanisms of Disulfiram-induced Cocaine Abstinence: Antabuse and Cocaine Relapse," Molecular Interventions, vol. 9, Issue 4, Aug. 2009, 13 pages.
MX/a/2010/001390, "Office Action," dated Mar. 1, 2016 (8 pages) and translation (10 pages).
Kojima et al., Seitai-No-Kagaku, 1998, vol. 49 No. 5, pp. 488-489.
Petrakis et al., "Naltrexone and Disulfiram in Patients With Alcohol Dependence and Current Depression," J. Clin. Psychopharmacol., 2007, vol. 27, No. 2, pp. 160-165.
Prigatano, et al., "Neuropsychological Functioning in Recidivist Alcoholics Treated with Disulfiram," Alcohol. Clin. Exp. Res., 1977, vol. 1, No. 1, pp. 81-85.
Japanese Application No. 2014-107381, Office Action dated May 9, 2017, 8 pages.
Japanese Application No. 2016-162881, Office Action dated Jun. 27, 2017, 10 pages.
Australian Patent Application No. 2014202047, Examination Report No. 1 dated May 19, 2017, 5 pages.
Manvich et al., "Dopamine β-Hydroxylase Inhibitors Enhance the Discriminative Stimulus Effects of Cocaine in Rats," J. Pharmacol. Exp. Ther. 347:564-573, Dec. 2013, 10 pages.
Merck Manual, 18th edition, 2005, URL: http://merckmanual.jp/mmpej/print/sec15/ch198f.html, plus English translation, 4 pages.
Jupp et al., "New horizons for therapeutics in drug and alcohol abuse," Pharmacology & Therapeutics 125 (2010) pp. 138-168, 31 pages.
EP17185804.0 , "Extended European Search Report", dated Oct. 23, 2017, 9 pages.
IL203722 , "Office Action", dated Jul. 25, 2017, 5 pages.
MXA2015009454 , "Office Action", dated Oct. 6, 2017, 8 pages.
"4 sympatheticoparalytic drug", Handbook of Practical Drug for the Circulatory System, chief editor: Zhang Chuanhai, Jilin People's Publishing House, Apr. 2006, p. 3.
CN201611204491.7, "Office Action", dated Mar. 26, 2019, 21 pages.
EP17165804.0, "Office Action", dated Jun. 18, 2019, 4 pages.
Goldstein, et al., "Inhibition of Dopamine-13-Hydroxylase by Disulfiram", Life Sciences, vol. 3, 1964, pp. 763-767.
JP2016-162881, "Office Action," dated Feb. 6, 2018, 8 pages.
Yakuzai-Gaku, New, 4th Edition, 3rd issue, 2003, pp. 370, 5 pages.
Nestler, Eric J.; "Is there a common molecular pathway for addiction?"; Nature Neuroscience, vol. 8, No. 11; Nov. 2005; published online Oct. 26, 2005; pp. 1445-1449.

\* cited by examiner

Figure 2

| ENZYME | ASSAY |
|---|---|
| Tyrosine hydroxylase | Release of [$^3$H$_2$O] associated with conversion of L-[3,5-$^3$H]-tyrosine to DOPA |
| Acetyl CoA synthetase | Utilization of [$^3$H]-acetic sodium acetate |
| Acyl-CoA, Cholesterol acyltransferase | Formation of cholesteryl ester from [1-$^{14}$C]-palmitoyl-CoA and endogenous cholesterol |
| Ca$^{2+}$/Calmodulin-protein kinase II | Phosphorylation [$^{32}$P] of BB40 (a synthetic peptide substrate) |
| Cyclooxygenase-1 | Oxidation of arachidonic acid followed by spectrophotometric quantitaion of malondialdehyde |
| HMG-CoA reductase | Formation of [$^{14}$C]-mevalonic acid fom [$^{14}$C]-HMG-CoA |
| Neutral endopeptidase (human) | Formation of 4-methoxy-2-naphthylamine from glutaryl-ala-ala-phe-4-methoxy-2-naphthylamide |
| Nitric oxide synthase (constitutive) | Conversion of [$^3$H]-arginine to [$^3$H]-citrulline |
| Nitric oxide synthase (inducible) | Measurement of iNOS reaction products (NO$_2$ and NO$_3$) in cytosol preparation from mouse macrophages induced by interferon-γ and lipopolysaccharide |
| Phosphodiesterase III (human) | Conversion of [$^3$H]-cAMP to [$^3$H]-AMP which is subsequently converted to [$^3$H]-adenosine |
| Phospholipase A$_2$ | Formation of [$^{14}$C]-palmitate from [$^{14}$C]-3-phosphatidylcholine |
| Protein kinase C (non-selective) | Phosphorylation [$^{32}$P]of Histone III |

Figure 3

| ENZYME OR RECEPTOR | IC$_{50}$ (enzyme) or pKi (receptor) |
|---|---|
| *Enzymes* | |
| Dopamine-β-hydroxylase (bovine) | 8.5 nM |
| Dopamine-β-hydroxylase (human) | 9 nM |
| Acetyl CoA Synthetase | < 10 μM |
| Acyl-CoA: Cholesterol Acyltransferase | < 10 μM |
| Ca$^{2+}$/Calmodulin Protein Kinase II | < 10 μM |
| Cyclooxygenase-1 | < 10 μM |
| HMG-CoA Reductase | < 10 μM |
| Neutral Endopeptidase (human) | < 10 μM |
| Nitric oxide synthase (constitutive) | < 10 μM |
| Nitric oxide synthase (inducible) | < 10 μM |
| Phosphodiesterase III (human) | < 10 μM |
| Phospholipase A$_2$ | < 10 μM |
| Protein Kinase (non-selective) | < 10 μM |
| | |
| *Receptors* | |
| α$_{1A}$, α$_{1B}$ adrenoceptors | < 5 |
| α$_{2A}$, α$_{2B}$ adrenoceptors | < 5 |
| β$_1$, β$_2$ adrenoceptors | < 5 |
| M$_1$ muscarinic receptors | < 5 |
| D$_1$, D$_2$ dopamine receptors | < 5 |
| μ-opioid receptors | < 5 |
| 5-HT$_{1A}$, 5-HT$_{2A}$, 5-HT$_{2C}$ serotonin receptors | < 5 |

Figure 4

| ENZYME | N | CONCENTRATION OF NEPICASTAT (µM) | % INHIBITION OF ENZYME | IC$_{50}$* (µM) |
|---|---|---|---|---|
| Tyrosine hydroxylase | 2 | 100 | 11 | >100 |
| NO synthase (constitutive) | 2 | 10 | 6 | >10 |
| NO synthase (inducible) | 2 | 10 | -1 | >10 |
| Phosphodiesterase III | 2 | 100 | -9 | >100 |
| Phospholipase A$_2$ | 2 | 300 | 3 | >300 |
| Neutral endopeptidase (human) | 2 | 10 | -12 | >10 |
| CA$^{2+}$/calmodulin dependent protein kinase II | 2 | 100 | 53 | ~100 |
| Acetyl CoA synthetase | 2 | 100 | -4 | >100 |
| Acyl CoA-cholesterol acyl transferase | 2 | 100 | 6 | >100 |
| HMG-CoA reductase | 2 | 30 | 16 | >30 |
| Protein kinase (non-selective) | 2 | 300 | 39 | >300 |
| Cyclooxygenase-1 | 2 | 300 | 44 | >300 |

* Approximate estimation of IC$_{50}$

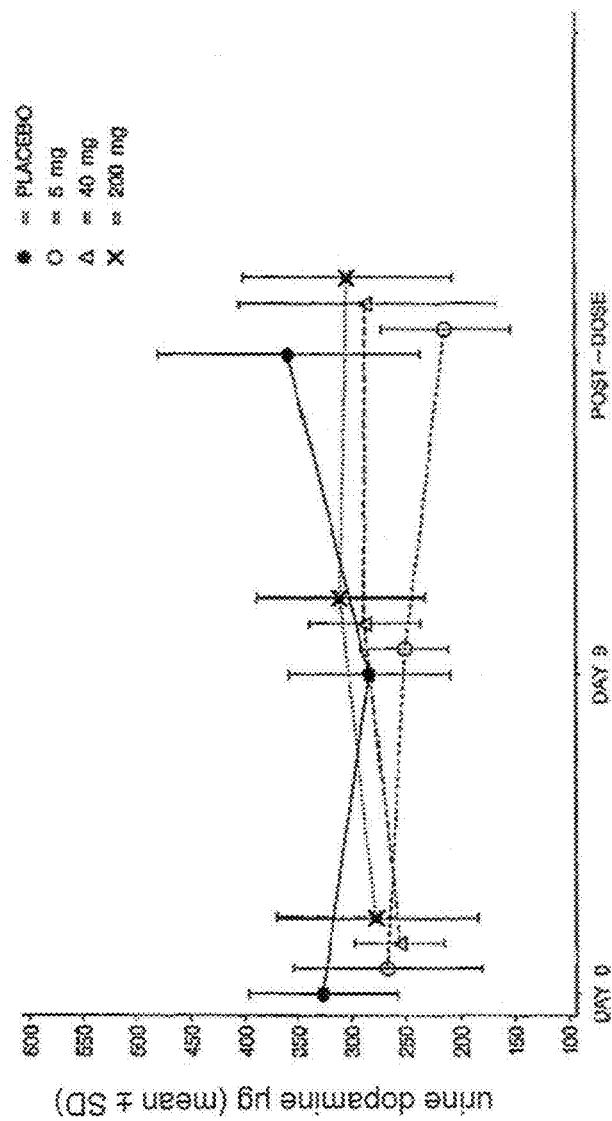

METHODS FOR TREATING DEPENDENCE

CROSS-REFERENCE TO RELATED APPLICATIONS

This application is a continuation of U.S. Ser. No. 12/187,166 filed Aug. 6, 2008 which claims the benefit of and priority under 35 U.S.C. § 119(e) to U.S. Provisional Patent Application Ser. Nos. 60/935,323, "Methods for Treating Dependence Using Nepicastat" filed Aug. 6, 2007, 60/956,555, "Methods for Treating Dependence Using Nepicastat" filed Aug. 17, 2007, and 60/960,591, "Methods for Treating Dependence Using Nepicastat" filed Oct. 4, 2007, which are all incorporated herein by reference in their entirety.

FIELD OF INVENTION

Provided are certain methods of treating patients suffering from or susceptible to at least one symptom of abuse of, dependence on, or withdrawal from at least one substance with Compound A. Also provided are certain methods of treating at least one phase of substance dependence on at least one substance in patients and certain methods of treating at least one phase of cocaine dependence in patients.

BACKGROUND OF THE INVENTION

Substance abuse and dependence are characterized by substance craving, seeking, and use with loss of control in limiting intake of the substance. These behaviors occur despite significant substance use related problems and at the expense of other behaviors. In 2004, approximately 22.5 million Americans aged 12 or older needed treatment for substance (alcohol or illicit drug) abuse. The latest estimate for the costs to society of illicit drug abuse alone is $181 billion (2002).

The problem of cocaine abuse and dependence is a major medical, social, and legal concern. According to the 2005 National Survey on Drug Use and Health, approximately 13.9% of Americans aged 12 and older have tried cocaine at least once in their lifetimes and 3.3% have tried crack cocaine at least once in their lifetimes. More troublesome, in 2005, there were 2.4 million persons who were current cocaine users, which is greater than in 2004 when the number was 2.0 million. Similarly, the number of current crack users increased from 467,000 in 2004 to 682,000 in 2005. In 2004, the Drug Abuse Warning Network estimated 940,953 drug-related emergency room visits nationwide, and cocaine was the involved in the majority of these.

Clearly, there is a need for a broadly effective treatment approach, and one including a medication component may be more effective than current behavioral treatments such as cognitive behavioral therapy or contingency management alone. A variety of treatments have been studied in clinical trials, without noteworthy success. In particular, numerous randomized controlled clinical trials of antidepressants have been completed, including trials of desipramine, fluoxetine, bupropion, and imipramine. Clinical trials of mood stabilizers, including carbamazepine and lithium have also been completed, as have trials of phenyloin, direct or indirect dopamine agonists, including bromocriptine, pergolide, amantadine, mazindole, and methylphenidate. A range of other agents, including ritanserin, gepirone, nimodipine, and naltrexone have been studied as well. None of these compounds has proved reliably efficacious. Several medications acting on GABA systems have been evaluated as treatments for cocaine dependence, including tiagabine, baclofen, and vigabatrin. Results for tiagabine have been equivocal, those for baclofen have been slightly more encouraging, though not compelling. Studies of vigabatrin have been perhaps equally encouraging, though based primarily on open-label trials. The outcomes from these development efforts have generally been discouraging.

The dopamine β-hydroxylase (DBH) inhibitor disulfuram is the most effective pharmacologic treatment for cocaine dependence currently available. Unfortunately, disulfuram non-specifically inhibits several enzymes, including aldehyde dehydrogenase and plasma esterases. Disulfuram and related compounds chelate copper, which is a necessary cofactor for a variety of enzymes, including aldehyde dehydrogenase, plasma esterases and DBH. By inhibiting aldehyde dehydrogenase, disulfuram alters the metabolism of alcohol (ethanol), producing the disulfuram-ethanol reaction. This reaction consists of flushing, nausea, and hypotension.

Inhibition of plasma esterases slows the elimination of cocaine, which can result in elevations in plasma cocaine levels. In laboratory studies evaluating effects of intranasal cocaine during treatment with disulfuram, disulfuram treatment markedly increased plasma cocaine levels. Increased cocaine levels were not associated with alterations in physiologic or subjective effects of cocaine, however. Six-fold elevations in plasma cocaine levels were observed in one controlled study, and greater elevations may occur in the context of uncontrolled illicit use. A subsequent study using IV cocaine dosing documented that disulfuram slowed the elimination of cocaine, presumably by inhibiting plasma esterases. Slow absorption following intranasal dosing accounted for the increases in plasma concentrations observed earlier.

Several studies have shown preliminary efficacy of disulfuram as a treatment of cocaine dependence. In human laboratory studies, treatment with disulfuram reduced the positive subjective effects produced by cocaine. Patients with comorbid alcohol and cocaine dependence had improved outcomes when treated with disulfuram, up to 500 mg. Similarly, buprenorphine-maintained opiate- and cocaine-dependent patients reduced cocaine use during treatment with disulfuram. Recently, results from a large clinical trial suggested that disulfuram 250 mg per day was associated with reduced cocaine use compared to placebo, regardless of alcohol use pattern or type of psychotherapy provided. In this study, 112 cocaine-dependent volunteers were randomized to placebo or disulfuram, and provided one of two psychotherapies. Disulfuram treatment was associated with reduced cocaine use documented by the provision of fewer cocaine-positive urine samples compared to placebo treatment. The effect size was modest and this outcome remains to be replicated.

Disulfuram inhibits DBH, the single enzyme that mediates the synthesis of norepinephrine (NE). DBH is expressed in noradrenergic neurons and is localized within synaptic vesicles and is released along with NE. DBH can be measured in the plasma, and the concentration of DBH is highly heritable and variability in activity is largely accounted for by variability at the DBH locus. The T variant (−1021C→T) is associated with diminished DBH gene transcription and with lower DBH activity. This allele is fairly common. The frequency of the T allele is reported to be 20% among African-Americans, 22% among Northern European Americans and 16% among Japanese. The corresponding haplotype frequencies are 0.32, 0.34, and 0.09 for these populations, respectively.

Several reports indicate that disulfuram is more effective in patients with lower DBH activity. It has been shown that in subjects with low DBH activity, the proportion of cocaine-positive urines decreased over time during treatment with disulfuram 250 mg/day relative to placebo but significantly increased over time during treatment with 62.5 mg and 125 mg disulfuram/day (p's<0.04). In those with high DBH activity, the proportion of cocaine-positive urines increased over time with disulfuram at 62.5 mg/day relative to placebo (p=0.001). Thus, the efficacy of 250 mg/day disulfuram treatment appears limited to those with low DBH activity, which corresponds to the C→T genotype. Doses of disulfuram lower than 250 mg/day appear to increase cocaine use, possibly by reducing cocaine clearance by inhibiting plasma esterases, thus increasing the abuse-related euphoric effects of cocaine.

Disulfuram more effectively reduces cocaine use in patients with the DBH C→T genotype associated with lower DBH activity. Presumably, disulfuram more completely inhibits DBH in those with lower DBH activity, so that disulfuram is more effective in those with the lower activity C→T genotype. The observation that disulfuram is more effective in patients with the low-activity DBH C→T genotype confirms that inhibition of DBH is a key mechanism of action for disulfuram as a therapy for cocaine dependence.

While disulfuram provides a proof-of-concept that DBH inhibitors are promising treatments for cocaine dependence, the usefulness of disulfuram itself as a treatment for cocaine dependence is severely limited by its interactions with alcohol and cocaine.

SUMMARY OF THE INVENTION

Provided are methods of treating patients suffering from or susceptible to at least one symptom of abuse of, dependence on, or withdrawal from at least one substance. The methods include administering to the patient a therapeutically effective amount of Compound A.

Also provided are methods of treating at least one phase of substance dependence on at least one substance in a patient, in which the at least one phase is selected from acquisition, maintenance, extinction, and relapse. The methods include administering to the patient a therapeutically effective amount of Compound A.

Also provided are methods of treating at least one phase of cocaine dependence in a patient, in which the at least one phase is selected from acquisition, maintenance, extinction, and relapse. The methods include administering to the patient a therapeutically effective amount of Compound A.

DESCRIPTION OF DRAWINGS

FIG. 2 shows the details of the individual enzymatic assays.

FIG. 3 shows a table with the affinities (IC50s or PKi) of nepicastat with DBH and a range of selected enzymes and receptors.

FIG. 4 shows the effects of nepicastat on % inhibition of enzyme activity.

FIG. 5 shows the urinary dopamine levels in normal volunteers after 24 hour treatment with nepicastat.

DETAILED DESCRIPTION

Figure 1:
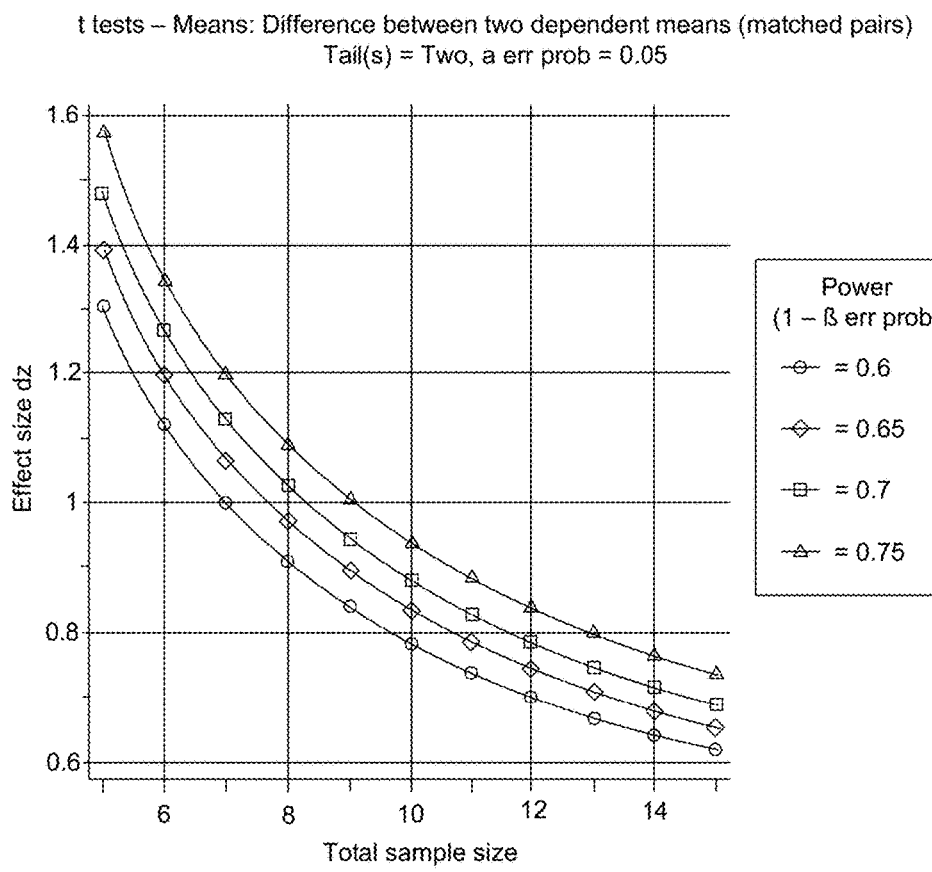
FIG. 1 shows the effect size achieved with sample sizes ranging from 5 to 15.

As used in the present specification, the following words and phrases are generally intended to have the meanings as set forth below, except to the extent that the context in which they are used indicates otherwise.

As used herein "Compound A" includes (S)-5-Aminomethyl-1-(5,7-difluoro-1,2,3,4-tetrahydronaphth-2-yl)-2,3-dihydro-2-thioxo-1H-imidazole, (R)-5-Aminomethyl-1-(5,7-difluoro-1,2,3,4-tetrahydronaphth-2-yl)-2,3-dihydro-2-thioxo-1H-imidazole, and mixtures thereof, as well as pharmaceutically acceptable salts thereof, such as the hydrochloride salt. In some embodiments nepicastat is used ((S)-5-Aminomethyl-1-(5,7-difluoro-1,2,3,4-tetrahydronaphth-2-yl)-2,3-dihydro-2-thioxo-1H-imidazole hydrochloride).

As used herein, "Compound B" refers to (R)-5-Aminomethyl-1-(5,7-difluoro-1,2,3,4-tetrahydronaphth-2-yl)-2,3-dihydro-2-thioxo-1H-imidazole, as well as pharmaceutically acceptable salts thereof, such as the hydrochloride salt.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH2)n-COOH where n is 0-4, and like salts.

In addition, if a compound is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "patient," as used herein, refers to a mammal. In certain embodiments, the term "patient" refers to a human.

The terms "administer," "administering," or "administration," as used herein, refer to either directly administering Compound A or a composition thereof to a patient.

The terms "treat" or "treating," as used herein, refers to partially or completely alleviating, inhibiting, preventing, ameliorating and/or relieving the condition, or at least one symptom thereof.

The terms "suffer" or "suffering" as used herein refers to one or more conditions that a patient has been diagnosed with, or is suspected to have.

The term "susceptible" as used herein refers to having a likelihood of being affected by at least one symptom of a condition.

Those of ordinary skill in the art will appreciate that "substance abuse" often involves symptoms of physical and/or psychological "dependence." Also, when the substance of abuse is withdrawn from a dependent individual, the individual often develops certain symptoms including sleep and mood disturbance and intense craving of the substance of abuse, known as "withdrawal." The methods described herein encompass treatment of substance abuse itself, dependence, and also of withdrawal.

The term "substance abuse," as used herein, can be defined with reference to criteria set forth in the Diagnostic and Statistical Manual of Mental Disorders, 4$^{th}$ Ed. Text revision (2000) ("DSM-IV TR"), which was prepared by the Task Force on DSM-IV of the American Psychiatric Association. A feature of substance abuse is a maladaptive pattern of substance use manifested by recurrent and significant adverse consequences related to the repeated use of substances. As recited in the DSM-IV TR, substance abuse is defined as maladaptive pattern of substance abuse leading to clinically significant impairment or distress, as manifested by at least one of the following symptoms, occurring within a 12-month period: (1) recurrent substance use resulting in a failure to fulfill major role obligations at work, school, or home; (2) recurrent substance use in situations in which it is physically hazardous; (3) recurrent substance-related legal problems; and (4) continued substance use despite having persistent or recurrent social or interpersonal problems caused or exacerbated by the effects of the substance. In addition, the DSM-IV TR requires that the symptoms of substance abuse have never met the criteria for substance dependence. In some embodiments, treatment of substance abuse with nepicastat reduces the amount or frequency of substance use in a patient. In some embodiments, treatment of substance abuse with Compound A in a patient reduces at least one DSM-IV TR symptom for substance abuse. In some embodiments, treatment with Compound A in a patient reduces at least one symptom of substance abuse which includes by way of example and without limitation at least one of euphoria, apathy, irritability, recklessness, poor judgment, compulsion, aggression, anger, craving for the substance being abused, and mood disorders. In some embodiments, treatment with Compound A reduces the substance craving induced by a stressful event in a patient.

As used herein, the phrase "reduces a symptom" refers to reducing at least one of the frequency and amplitude of a symptom of a condition in a patient. In certain embodiments the patient enters remission and no longer experiences the symptom.

As used herein, the phrase "increases a symptom" refers to increasing at least one of the frequency and amplitude of a symptom of a condition in a patient.

The term "substance dependence," as used herein, can be defined with reference to criteria set forth in the DSM-IV TR. The symptoms for substance dependence set forth in DSM-IV TR is a pattern of substance use, leading to clinically significant impairment or distress as manifested by at least three selected from the following group, occurring at any time within the same twelve month period: (1) tolerance as defined by either (a) a need for substantially increased amounts of the substance to achieve the desired effect; or (b) substantially diminished effect with continued use of the same amount of the substance; (2) withdrawal, as demonstrated by either (a) the characteristic withdrawal syndrome for the specific substance; or (b) the same, or a closely related substance is taken to relieve or avoid withdrawal symptoms; (3) the substance is often taken in larger amounts or over a longer period than was intended; (4) there is a persistent desire or unsuccessful efforts to cut down or control substance use; (5) a great deal of time is spent in activities to obtain the substance, use the substance, or recover from its effects; (6) important social, occupational or recreational activities are given up or reduced because of substance use; and (7) the substance use is continued despite knowledge of having a persistent or recurrent physical or psychological problem that is likely to have been caused or exacerbated by the substance. Substance dependence can be with physiological dependence, where evidence of tolerance or withdrawal is present, or without physiological dependence, where no evidence of tolerance or withdrawal is present. In some embodiments, Compound A treatment of substance dependence reduces the amount or frequency of substance use by a patient. In some embodiments, Compound A treatment of substance dependence reduces at least one DSM-IV TR symptom for substance dependence in a patient. In some embodiments, treatment with Compound A in a patient reduces at least one symptom of substance dependence which includes by way of example and without limitation at least one of euphoria, apathy, irritability, recklessness, poor judgment, compulsion, aggression, anger, craving for the substance depended upon, and mood disorders. In some embodiments, treatment with Compound A reduces the substance craving induced by a stressful event in a patient.

As used herein, "remission" refers to a state during which the occurrence of at least one symptom of substance abuse or dependence has been reduced. In some embodiments, the term remission does not apply if the patient is on agonist therapy or in a controlled environment where access to the relevant substance is restricted. In some embodiments remission refers to a state during which the occurrence of at least one symptom of substance abuse or dependence does not occur. In some embodiments, remission refers to a state during which all symptoms of substance abuse or dependence have been reduced in a patient. In some embodiments, remission refers to a state during which no symptoms of substance abuse or dependence occur. In some embodiments, remission refers to a state during which substance use does not occur.

In some embodiments, the remission is characterized by at least one of early full remission, early partial remission, sustained full remission, and sustained partial remission and only applies after none of the symptoms for substance abuse and dependence have been present for at least one month. The definition of these four types of remission are based on the interval of time that has elapsed since the cessation of dependence (early versus sustained remission) and whether there is continued presence of at least one symptom of substance dependence or abuse (partial versus full remission).

The qualifier "early full remission" is used when for at least one month, but for less than twelve months, no symptom of substance dependence or substance abuse has been met.

The qualifier "early partial remission" is used when for at least one month but less than 12 months, at least one symptom of substance dependence or substance abuse has been met, but the criteria for substance dependence or substance abuse have not been met.

The term "sustained full remission" is used when none of the symptoms of substance dependence or substance abuse have been met at any time during a period of at least twelve months.

The term "sustained partial remission" is used when for at least twelve months, at least one symptom of substance dependence or substance abuse has been met, but the criteria for substance dependence or substance abuse have not been met.

In some embodiments, Compound A treatment promotes remission in a patient. In some embodiments, Compound A treatment prolongs a period of remission period in a patient.

The phrase "prolong a period of remission" refers to increasing the interval of time during which the patient is in remission. In some embodiments, a stressful event can cause remission to end in a patient. In some embodiments, relapse occurs at the end of remission. In some embodiments, Compound A treatment reduces the likelihood that remission will end in a patient after a stressful event. In some embodiments, Compound A treatment promotes at least one of early partial remission, sustained full remission, sustained partial remission, and sustained full remission.

"Withdrawal" refers to a collection of symptoms that arise when administration of a relevant substance is reduced, delayed, or stopped. The substance-specific symptoms of withdrawal can cause clinically significant distress or impairment in social, occupational or other important areas of functioning, for example. These symptoms are not due to a general medical condition and are not better accounted for by another mental disorder. Withdrawal usually, but not necessarily, is associated with substance dependence. In some embodiments, treatment with Compound A reduces at least one symptom of withdrawal in a patient. In some embodiments, withdrawal symptoms include for example and without limitation apathy, irritability, recklessness, poor judgment, compulsion, aggression, anger, substance craving, mood disorders, and sleep disorders. In some embodiments, treatment with Compound A reduces the substance craving induced by a stressful event in a patient.

The term substance dependence can be characterized by the presence of at least one of the following conditions characterized in the DSM-IV TR: Alcohol Abuse; Alcohol Dependence; Alcohol Intoxication; Alcohol Intoxication Delirium; Alcohol Withdrawal; Alcohol Withdrawal Delirium; Alcohol-Induced Anxiety Disorder; Alcohol-Induced Mood Disorder; Alcohol-Induced Persisting Amnestic Disorder; Alcohol-Induced Persisting Dementia; Alcohol-Induced Psychotic Disorder, With Delusions; Alcohol-Induced Psychotic Disorder, With Hallucinations; Alcohol-Induced Sexual Dysfunction; Alcohol-Induced Sleep Disorder; Alcohol-Related Disorder Not Otherwise Specified (NOS); Amphetamine Abuse; Amphetamine Dependence; Amphetamine Intoxication; Amphetamine Intoxication Delirium; Amphetamine Withdrawal; Amphetamine-Induced Anxiety Disorder; Amphetamine-Induced Mood Disorder; Amphetamine-Induced Psychotic Disorder, With Delusions; Amphetamine-Induced Psychotic Disorder, With Hallucinations; Amphetamine-Induced Sexual Dysfunction; Amphetamine-Induced Sleep Disorder; Amphetamine-Related Disorder NOS; Cannabis Abuse; Cannabis Dependence; Cannabis Intoxication; Cannabis Intoxication Delirium; Cannabis-Induced Anxiety Disorder; Cannabis-Induced Psychotic Disorder, With Delusions; Cannabis-Induced Psychotic Disorder, With Hallucinations; Cannabis-Related Disorder NOS; Cocaine Abuse; Cocaine Dependence; Cocaine Intoxication; Cocaine Intoxication Delirium; Cocaine Withdrawal; Cocaine-Induced Anxiety Disorder; Cocaine-Induced Mood Disorder; Cocaine-Induced Psychotic Disorder, With Delusions; Cocaine-Induced Psychotic Disorder, With Hallucinations; Cocaine-Induced Sexual Dysfunction; Cocaine-Induced Sleep Disorder; Cocaine-Related Disorder NOS; Inhalant Abuse; Inhalant Dependence; Inhalant Intoxication; Inhalant Intoxication Delirium; Inhalant-Induced Anxiety Disorder; Inhalant-Induced Mood Disorder; Inhalant-Induced Persisting Dementia; Inhalant-Induced Psychotic Disorder, With Delusions; Inhalant-Induced Psychotic Disorder, With Hallucinations; Inhalant-Related Disorder NOS; Opioid Abuse; Opioid Dependence; Opioid Intoxication; Opioid Intoxication Delirium; Opioid Withdrawal; Opioid-Induced Mood Disorder; Opioid-Induced Psychotic Disorder, With Delusions; Opioid-Induced Psychotic Disorder, With Hallucinations; Opioid-Induced Sexual Dysfunction; Opioid-Induced Sleep Disorder; Opioid-Related Disorder NOS; Phencyclidine Abuse; Phencyclidine Dependence; Phencyclidine Intoxication; Phencyclidine Intoxication Delirium; Phencyclidine-Induced Anxiety Disorder; Phencyclidine-Induced Mood Disorder; Phencyclidine-Induced Psychotic Disorder, With Delusions; Phencyclidine-Induced Psychotic Disorder, With Hallucinations; and Phencyclidine-Related Disorder NOS.

The terms "cessation" and "withdrawal" may be, but need not be, in reference to the following conditions characterized in the DSM-IV TR: Nicotine Withdrawal; Nicotine-Related Disorder Not otherwise Specified; Nicotine Dependence, with physiological dependence; Nicotine Dependence, without physiological dependence; Nicotine Dependence, Early Full Remission; Nicotine Dependence, Early Partial Remission; Nicotine Dependence, Sustained Full Remission; Nicotine Dependence, Sustained Partial Remission; Nicotine Dependence, On Agonist Therapy; Opioid Withdrawal; Opioid-Related Disorder Not Otherwise Specified; Opioid Dependence, with physiological dependence; Opioid Dependence, without physiological dependence; Opioid Dependence, Early Full Remission; Opioid Dependence, Early Partial Remission; Opioid Dependence, Sustained Full Remission; Opioid Dependence, Sustained Partial Remission; Opioid Dependence On Agonist Therapy; and Opioid Dependence in a controlled environment; Ethanol Withdrawal; Ethanol Dependence with Physiological Dependence; Ethanol Withdrawal, without Physiological Dependence; Ethanol Withdrawal, Early Full Remission; Ethanol Withdrawal, Early Partial Remission; Ethanol Withdrawal, Sustained Full Remission; Ethanol Withdrawal, Sustained Partial Remission; Ethanol Withdrawal, on Agonist Therapy; Ethanol Withdrawal, In a Controlled Environment; Amphetamine Withdrawal; and Cocaine Withdrawal.

As used herein, "on agonist therapy" refers to being treated with an agonist for substance abuse, dependence, or withdrawal. The term "agonist" refers to a factor including, but not limited to a chemical compound, such as a small molecule or a complex organic compound or a protein, that triggers a response in a patient that is at least one response or partial response of the substance being abused, depended upon, or withdrawn from by the patient. For example, in some embodiments, "Opioid Dependence On Agonist Therapy" refers to Opioid Dependence on methadone therapy.

Withdrawal symptoms can arise upon reduction of any of a variety of substances. For example, the discontinued use of tobacco products, all of which contain nicotine, typically results in the onset of nicotine withdrawal conditions. Individuals often suffer the symptoms of nicotine withdrawal as a consequence of the discontinued use of tobacco in any form, including, but not limited to smoking of cigarette, cigar, or pipe tobacco, or the oral or intranasal ingestion of tobacco or chewing tobacco. Such oral or intranasal tobacco includes, but is not limited to snuff and chewing tobacco. The cessation of nicotine use or reduction in the amount of nicotine use, is often followed within 24 hours by symptoms including dysphoric, depressed mood; light-headedness; insomnia; irritability, frustration or anger; anxiety; nervous tremor; difficulty concentrating; restlessness; decreased heart rate; increased appetite or weight gain; and the craving for tobacco or nicotine. These symptoms often cause clinically significant distress or impairment in social, occupational, or other important areas of functioning. The methods described herein may be used to alleviate one or more symptoms attributed to nicotine withdrawal when such symptoms are not due to a general medical condition and are not better accounted for by another medical disorder. The present method is also helpful to those who have replaced, or partially replaced, their use of tobacco with the use of nicotine replacement therapy. Thus, such patients can be assisted to reduce and even eliminate entirely their dependence on nicotine in all forms.

The discontinuing or reduction in administration of an opioid, typically self-administration, through injection or orally, through smoking or intranasal ingestion, often results in the presence of a characteristic opioid withdrawal condition. This withdrawal condition can also be precipitated by administration of an opioid antagonist such as naloxone or naltrexone after opioid use. Opioid withdrawal is characterized by symptoms that are generally opposite to the opioid agonist effects. These withdrawal symptoms may include anxiety; restlessness; muscle aches, often in the back and legs; craving for opioids; irritability and increased sensitivity to pain; dysphoric mood; nausea or vomiting; lacrimation; rhinorrhoea; papillary dilation; piloerection; sweating; diarrhea; yawning; fever; and insomnia. When dependence is on short-acting opioids, such as heroin, withdrawal symptoms usually occur within 6-24 hours after the last dose, while with longer-acting opioids, such as methadone, symptoms may take 2-4 days to emerge. These symptoms often cause clinically significant distress or impairment in social, occupational or other important areas of functioning. The methods described herein can be used to alleviate one or more symptoms attributed to opioid withdrawal when such symptoms are not due to a general medical condition and are not better accounted for by another medical disorder.

The discontinuing of or reduction in use of ethanol (e.g., ethanol containing beverages) results in the onset of ethanol withdrawal conditions. Ethanol withdrawal conditions are characterized by symptoms that begin when blood concentrations of ethanol decline sharply, within 4 to 12 hours after ethanol use has been stopped or reduced. These ethanol withdrawal symptoms include craving for ethanol; autonomic hyperactivity (such as sweating or pulse rate greater than 100); hand tremor; insomnia; nausea; vomiting; transient visual, tactile, or auditory hallucinations or illusions; psychomotor agitation; anxiety; and grand mal seizures. These symptoms often cause clinically significant distress or impairment in social, occupational, or other important areas of functioning. The methods described herein may be used to alleviate one or more symptoms attributed to ethanol withdrawal when such symptoms are not due to a general medical condition and are not better accounted for by another medical disorder.

Cocaine abuse and dependence can cause cognitive, behavioral, and physiological symptoms. Symptoms of cocaine abuse and dependence can include varying degrees of attention deficit hyperactivity disorder and euphoria; increased energy, excitement, and sociability; less hunger and fatigue; a marked feeling of physical and mental strength; dysphoria; decreased sensation of pain; and craving for cocaine. Respiratory effects include symptoms such as bronchitis, shortness of breath, and chest pain, and cardiovascular effects include symptoms such as heart palpitations, arrhythmia, cardiomyopathy, and heart attacks. Symptoms also include dilated pupils, nausea, vomiting, headache, vertigo, anxiety, dizziness, psychosis, and confusion. Administration of cocaine through snorting or sniffing can result in ear, nose, and throat effects including nasal irritation, nasal crusting, recurrent nosebleeds, nasal stuffiness, and facial pain. In some embodiments, Compound A treatment reduces at least one symptom of cocaine abuse and dependence in a patient. In some embodiments, nepicstat treatment increases at least one negative subjective symptom of cocaine abuse and dependence.

Cocaine withdrawal symptoms can include a fatigue, lack of pleasure, depression, irritability, sleep disorders, increased appetite, pyschomotor retardation, agitation, extreme suspicion, and craving for cocaine. In some embodiments, Compound A treatment reduces at least one symptom of cocaine withdrawal.

Substance dependence can be characterized by the phases: acquisition, maintenance, extinction, and relapse. As used herein, the term "acquisition" refers to a phase of substance dependence in which dependence on the substance is initiated and acquired by a patient. In some embodiments, Compound A treatment inhibits the development of the acquisition phase in a patient. In some embodiments, Compound A treatment of the acquisition phase reduces at least one of the amount or frequency of substance use by a patient. In some embodiments, Compound A treatment of the acquisition phase reduces at least one DSM-IV symptom of substance abuse and dependence in a patient. In some embodiments, Compound A treatment of the acquisition phase reduces at least one symptom of substance abuse and dependence which include by way of example and without limitation at least one of euphoria, apathy, irritability, recklessness, poor judgment, compulsion, aggression, anger, craving for the substance being abused or depended upon, and mood disorders. In some embodiments, treatment with Compound A reduces the substance craving induced by a stressful event in a patient during the acquisition phase.

"Maintenance" refers to a phase of substance dependence in which there is stable administration to or use of the substance by a patient. In some embodiments, a 10% variance in at least one of the amount and frequency of substance use by a patient is considered a stable behavior. In some embodiments, Compound A treatment of the maintenance phase reduces at least one of the amount and frequency of substance use by a patient. In some embodiments, Compound A treatment of the maintenance phase reduces at least one DSM-IV symptom of substance abuse and dependence in a patient. In some embodiments, Compound A treatment of the maintenance phase reduces at least one symptom of substance abuse and dependence which includes by way of example and without limitation at least one of euphoria, apathy, irritability, recklessness, poor judgment, compulsion, aggression, anger, craving for the substance being abused or depended upon, and mood disorders. In some embodiments, treatment with Compound A reduces the substance craving induced by a stressful event in a patient during the maintenance phase.

"Extinction" refers to a phase of substance dependence in which the substance is not provided to a patient or a patient abstains from use of the substance. In some embodiments, the dependence on the substance is extinguished or reduced in the extinction phase. In some embodiments, at least one withdrawal symptom occurs in the extinction phase. In some embodiments, Compound A treatment promotes the development of the extinction phase in a patient. In some embodiments, Compound A treatment of the extinction phase reduces at least one DSM-IV symptom of substance abuse and dependence in a patient. In some embodiments, Compound A treatment during the extinction phase reduces at least one symptom of substance abuse and dependence which includes by way of example and without limitation at least one of euphoria, apathy, irritability, recklessness, poor judgment, compulsion, aggression, anger, craving for the substance being abused or depended upon, and mood disorders. In some embodiments, Compound A treatment reduces the withdrawal symptoms in a patient in the extinction phase. In some embodiments, treatment with Compound A reduces the substance craving induced by a stressful event in a patient in the extinction phase.

"Relapse" refers to recurrence of at least one symptom of substance abuse or dependence after a period of abstinence in a patient. In some embodiments, the relapse occurs at the end of remission. In some embodiments, a patient has undergone extinction training prior to relapse. In some embodiments, relapse occurs after drug priming, stress, or exposure to an environment related cue or stimulation that was previously associated with substance use. In some embodiments, Compound A treatment reduces the frequency of relapse in a patient. In some embodiments, Compound A treatment of the relapse phase reduces at least one DSM-IV symptom of substance abuse and dependence in a patient. In some embodiments, Compound A treatment of the relapse phase reduces at least one symptom of substance abuse and dependence which includes by way of example and without limitation at least one of euphoria, apathy, irritability, recklessness, poor judgment, compulsion, aggression, anger, craving for the substance being abused or depended upon, and mood disorders. In some embodiments, Compound A treatment reduces the withdrawal symptoms in a patient during the relapse phase. In some embodiments, treatment with Compound A reduces the substance craving induced by a stressful event in a patient during the relapse phase.

Treatment of substance abuse, dependence, and withdrawal may be conducted in stages. In some embodiments, an initial period of abstinence from substance use is preferred before induction of treatment with Compound A in a patient. In some embodiments, an initial low dose of Compound A is administered to a patient. In some embodiments, the amount of Compound A administered to a patient is escalated until a desired therapeutic response is observed. In some embodiments, the amount of Compound A is escalated in order to determine the optimal dose to treat the condition while minimizing symptoms, side effects, and cravings for the substance in a patient.

In some embodiments, Compound A treatment promotes remission. In some embodiments, the dose of Compound A is unchanged or tapered off after remission is reached in a patient.

Provided are methods of treating a patient suffering from or susceptible to at least one symptom of abuse of, dependence on, or withdrawal from at least one substance. The methods include administering to the patient a therapeutically effective amount of Compound A. In some embodiments, the at least one substance is selected from a drug of abuse and a medication. In some embodiments, the drug of abuse is selected from a psychostimulant agent, an opioid, a hallucinogen, an inhalant, a sedative, a tranquilizer, a hypnotic, an anxiolytic, and an illicit substance. In some embodiments, the psychostimulant agent is a beta-phenylisopropylamine derivative. In some embodiments, the beta-phenylisopropylamine derivative is selected from amphetamine, dextroamphetamine, and methamphetamine.

In some embodiments, the psychostimulant agent is selected from ecstasy, phenmetrazine, methylphenidate, diethylpropion, pemoline, mazindol, (−) cathione, and fenfluramine. In some embodiments, the opioid is selected from Lortab, Tramadol, heroin, methadone, hydrocodone, and oxycodone. In some embodiments, the hallucinogen is selected from psilocybin, a hallucinogenic mushroom, lysergic acid diethylamide (LSD), phencyclidine (PCP), and ketamine. In some embodiments, the inhalant is selected from benzene, toluene, o-xylene, m-xylene, p-xylene, ethylbenzene, fluorobenzene, o-difluorobenzene, 1,3,5-trifluorobenzene, 1,2,4-trifluorobenzene, pentafluorotoluene, pentafluorobenzene, and perfluorobenzene. In some embodiments, the medication is selected from an anesthetic, an analgesic, an anticholinergic agent, an antihistamine, a muscle relaxant, a nonsteroidal anti-inflammatory medication, an over the counter medication, and an antidepressant medication. In some embodiments, the drug of abuse is cocaine, alcohol, caffeine, opium, cannabinoid, cannabis, benzodiazapine carisprodol, tobacco, nicotine, Vicodin, Lorcet, Percocet, Percodan, and Tylox. In some embodiments, the drug of abuse is cocaine and the Compound A reduces at least one symptom of cocaine abuse and dependence in the patient selected from attention deficit hyperactivity disorder; euphoria; increased energy, excitement and sociability; less hunger and fatigue; a marked feeling of physical and mental strength; decreased sensation of pain; bronchitis; shortness of breath; chest pain; heart palpitations; arrhythmia; cardiomyopathy; heart attack; dilated pupils; nausea; vomiting; headache; vertigo; dizziness; anxiety; pychosis; confusion; nasal irritation; nasal crusting; recurrent nosebleeds; nasal stuffiness; facial pain; dysphoria; and craving for cocaine. In some embodiments, the drug of abuse is cocaine and the Compound A increases at least one negative subjective symptom of cocaine abuse and dependence. In some embodiments, the drug of abuse is cocaine and the Compound A reduces at least one symptom of cocaine withdrawal selected from fatigue, lack of pleasure, depression, irritability, sleep disorders, increased appetite, pyschomotor retardation, agitation, extreme suspicion, and craving for cocaine. In some embodiments, the Compound A treatment improves a score of the patient on at least one of the attention deficit hyperactivity disorder IV rating scale (ADHD-IV), Hamilton Depression Scale (HAM-D), Hamilton Anxiety Scale (HAM-A), Beck Depression inventory (BDI), apathy scale from Neuropsychiatric Inventory, and a cognitive function rating scale. In some embodiments, the cognitive function rating scale is selected from the Wechsler Adult Intelligence Scale-Revised (WAIS-R), Wechsler Memory Scale-Revised (WMS-R), Rey Auditory Verbal Learning Test (RAVLT, Trials I-VII), Rey Complex Figure Test (RCFT), and the Trail Making Test (TMT, Parts A and B). In some embodiments, the Compound A reduces in the patient at least one of the amount and frequency of substance use by the patient. In some embodiments, the Compound A reduces in the patient at least one symptom of abuse of, dependence on, or withdrawal from the at least one substance. In some embodiments, the Compound A reduces at least one symptom of substance abuse in the patient selected from recurrent substance use resulting in a failure to fulfill major role obligations at work, school, or home; recurrent substance use in situations in which it is physically hazardous; recurrent substance-related legal problems; and continued substance use despite having persistent or recurrent social or interpersonal problems caused or exacerbated by the effects of the substance. In some embodiments, the Compound A reduces at least one symptom of substance dependence in the patient selected from tolerance; withdrawal; the substance is often taken in larger amounts or over a longer period then was intended; there is a persistent desire and/or unsuccessful efforts to cut down or control substance use; a great deal of time is spent in at least one of activities to obtain the substance, use the substance, and recover from its effects; at least one of important social, occupational and recreational activities are given up and/or reduced because of substance use; and the substance use is continued despite knowledge of having a persistent and/or recurrent physical and/or psychological problem that is likely to have been caused or exacerbated by the substance. In some embodiments, the Compound A promotes remission in the patient. In some embodiments, the remission is characterized by at least one of early full remission, early partial remission, sustained full remission, and sustained partial remission. In some embodiments, the Compound A prolongs a period of remission in the patient. In some embodiments, the methods further include treatment with at least one of contingency management and cognitive behavioral therapy. In some embodiments, the methods further include co-administering a therapeutically effective amount of least one other agent selected from a selective serotonin reuptake inhibitor (SSRI), a serotonin-norepinephrine reuptake inhibitor (SNRI), a norepinephrine reuptake inhibitor (NRI), a norepinephrine-dopamine reuptake inhibitor (NDRI), a serotonin 5-hydroxytryptamine1A (5HT1A) antagonist, a dopamine β-hydroxylase inhibitor, an adenosine receptor antagonist, an adenosine A2A receptor antagonist, a monoamine oxidase inhibitor (MAOI), a monoamine oxidase B inhibitor, a sodium channel blocker, a calcium channel blocker, a central and peripheral alpha adrenergic receptor antagonist, a central alpha adrenergic agonist, a central or peripheral beta adrenergic receptor antagonist, a NK-1 receptor antagonist, a corticotropin releasing factor (CRF) antagonist, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, a serotonin 5HT2 antagonist, an opioid, a carboxylase inhibitor, a partial opioid agonist, a partial nicotinic agonist, and an inhalant. In some embodiments, the at least one other agent is a SSRI selected from paroxetine, sertraline, citalopram, escitalopram, and fluoxetine. In some embodiments, the at least one other agent is a SNRI selected from duloxetine, mirtazapine, and venlafaxine. In some embodiments, the at least one other agent is a NRI selected from bupropion and atomoxetine. In some embodiments, the at least other agent is the NDRI bupropion. In some embodiments, the at least one other agent is the dopamine β-hydroxylase inhibitor disulfuram. In some embodiments, the at least one other agent is the adenosine A2A receptor antagonist istradefylline. In some embodiments, the at least one other agent is a sodium channel blocker selected from lamotrigine, carbamazepine, oxcarbazepine, and valproate. In some embodiments, the at least one other agent is a calcium channel blocker selected from nimodopone, lamotrigine, and carbamazepine. In some embodiments, the at least one other agent is the central and peripheral alpha adrenergic receptor antagonist prazosin. In some embodiments, the at least one other agent is the central alpha adrenergic agonist clonidine. In some embodiments, the at least one other agent is the central or peripheral beta adrenergic receptor antagonist propranolol. In some embodiments, the at least one other agent is an atypical antidepressant/antipsychotic selected from bupropion, olanzepine, risperidone, and quetiapine. In some embodiments, the at least one other agent is a tricyclic selected from amitriptyline, amoxapine, desipramine, doxepin, imipramine, nortriptyline, protiptyline, and trimipramine. In some embodiments, the at least one other agent is an anticonvulsant selected from phenyloin, lamotrigine, carbamazepine, oxcarbazepine, valproate, topiramate, tiagabine, vigabatrin, and levetiracetam. In some embodiments, the at least one other agent is the glutamate antagonist topiramate. In some embodiments, the at least one other agent is a GABA agonist selected from baclofen, valproate, and topiramate. In some embodiments, the at least one other agent is the dopamine metabolism enzyme inhibitor carbidopa. In some embodiments, the at least one other agent is the partial dopamine D2 agonist aripiprazole. In some embodiments, the at least one other agent is an opioid receptor antagonist selected from naltrexone and naloxone. In some embodiments, the at least one other agent is a mood stabilizer selected from carbamazepine and lithium. In some embodiments, the at least one other agent is a direct or indirect dopamine agonist selected from dopamine, bromocriptine, pergolide, amantadine, mazindole, and methylphenidate. In some embodiments, the at least other agent is the partial 5HT1 agonist gepirone. In some embodiments, the at least other agent is the serotonin 5HT2 antagonist ritanserin. In some embodiments, the at least other agent is the opioid methadone. In some embodiments, the at least other agent is the partial opioid agonist buprenorphine. In some embodiments, the at least other agent is the partial nicotinic agonist champix. In some embodiments, the at least one other agent is an inhalant selected from benzene, toluene, o-xylene, m-xylene, p-xylene, ethylbenzene, fluorobenzene, o-difluorobenzene, 1,3, 5-trifluorobenzene, 1,2,4-trifluorobenzene, pentafluorotoluene, pentafluorobenzene, and perfluorobenzene. In some embodiments, the methods further include co-administering a therapeutically effective amount of least one other agent selected from benzodiazepine, levodopa, carisprodol, modafenil, acamprosate, gamma-butyrolactone, gamma-hydroxybutyrate, opium, psilopcybin, hallucinogenic mushroom, tobacco, and nicotine. In some embodiments, the Compound A is administered to the patient after a period of abstinence from substance use by the patient. In some embodiments, the therapeutically effective amount of Compound A in the patient is determined by escalating the amount of Compound A administered to the patient until a desired therapeutic response is observed. In some embodiments, the amount of Compound A is tapered off after remission is reached in the patient. In some embodiments, the amount of Compound A is unchanged after remission is reached in the patient.

Also provided are methods of treating at least one phase of substance dependence on at least one substance in a patient. In some embodiments, the at least one phase of substance dependence is selected from acquisition, maintenance, extinction, and relapse. The methods include administering to the patient a therapeutically effective amount of Compound A. In some embodiments, the Compound A inhibits the development of the acquisition phase in the patient. In some embodiments, the Compound A promotes the development of the extinction phase in the patient. In some embodiments, the Compound A reduces the frequency of relapse in the patient. In some embodiments, the at least one substance is selected from a drug of abuse and a medication. In some embodiments, the drug of abuse is selected from a psychostimulant agent, an opioid, a hallucinogen, an inhalant, a sedative, a tranquilizer, a hypnotic, an anxiolytic, and an illicit substance. In some embodiments, the psychostimulant agent is a beta-phenylisopropylamine derivative. In some embodiments, the beta-phenylisopropylamine derivative is selected from amphetamine, dextroamphetamine, and methamphetamine. In some embodiments, the psychostimulant agent is selected from ecstasy, phenmetrazine, methylphenidate, diethylpropion, pemoline, mazindol, (−) cathione, and fenfluramine. In some embodiments, the opioid is selected from Lortab, Tramadol, heroin, methadone, hydrocodone, and oxycodone. In some embodiments, the hallucinogen is selected from psilocybin, a hallucinogenic mushroom, lysergic acid diethylamide (LSD), phencyclidine (PCP), and ketamine. In some embodiments, the inhalant is selected from benzene, toluene, o-xylene, m-xylene, p-xylene, ethylbenzene, fluorobenzene, o-difluorobenzene, 1,3,5-trifluorobenzene, 1,2,4-trifluorobenzene, pentafluorotoluene, pentafluorobenzene, and perfluorobenzene. In some embodiments, the medication is selected from an anesthetic, an analgesic, an anticholinergic agent, an antihistamine, a muscle relaxant, a nonsteroidal anti-inflammatory medication, an over the counter medication, and an antidepressant medication. In some embodiments, the drug of abuse is alcohol, caffeine, opium, cannabinoid, cannabis, benzodiazapine, carisprodol, tobacco, nicotine, Vicodin, Lorcet, Percocet, Percodan, and Tylox. In some embodiments, the Compound A treatment improves a score of the patient on at least one of the ADHD-IV, HAM-D, HAM-A, BDI, apathy scale from Neuropsychiatric Inventory, and a cognitive function rating scale. In some embodiments, the cognitive function rating scale is selected from the WAIS-R, WMS-R, RAVLT, Trials I-VII, RCFT, and TMT, Parts A and B. In some embodiments, the Compound A reduces in the patient at least one of the amount and frequency of use of the at least one substance by the patient. In some embodiments, the Compound A reduces in the patient at least one symptom of abuse of, dependence on, or withdrawal from the at least one substance. In some embodiments, the Compound A reduces at least one symptom of substance abuse in the patient selected from recurrent substance use resulting in a failure to fulfill major role obligations at work, school, or home; recurrent substance use in situations in which it is physically hazardous; recurrent substance-related legal problems; and continued substance use despite having persistent or recurrent social or interpersonal problems caused or exacerbated by the effects of the substance. In some embodiments, the Compound A reduces at least one symptom of substance dependence in the patient selected from tolerance; withdrawal; the substance is often taken in larger amounts or over a longer period then was intended; there is a persistent desire and/or unsuccessful efforts to cut down or control substance use; a great deal of time is spent in at least one of activities to obtain the substance, use the substance, and recover from its effects; at least one of important social, occupational and recreational activities are given up and/or reduced because of substance use; and the substance use is continued despite knowledge of having a persistent and/or recurrent physical and/or psychological problem that is likely to have been caused or exacerbated by the substance. In some embodiments, the Compound A promotes remission in the patient. In some embodiments, the remission is characterized by at least one of early full remission, early partial remission, sustained full remission, and sustained partial remission. In some embodiments, the Compound A prolongs a period of remission in the patient. In some embodiments, the methods further include treatment with at least one of contingency management and cognitive behavioral therapy. In some embodiments, the methods further include co-administering a therapeutically effective amount of least one other agent selected from a selective serotonin reuptake inhibitor (SSRI), a serotonin-norepinephrine reuptake inhibitor (SNRI), a norepinephrine reuptake inhibitor (NRI), a norepinephrine-dopamine reuptake inhibitor (NDRI), a serotonin 5-hydroxytryptamine1A (5HT1A) antagonist, a dopamine β-hydroxylase inhibitor, an adenosine receptor antagonist, an adenosine A2A receptor antagonist, a monoamine oxidase inhibitor (MAOI), a monoamine oxidase B inhibitor, a sodium channel blocker, a calcium channel blocker, a central and peripheral alpha adrenergic receptor antagonist, a central alpha adrenergic agonist, a central or peripheral beta adrenergic receptor antagonist, a NK-1 receptor antagonist, a corticotropin releasing factor (CRF) antagonist, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, a serotonin 5HT2 antagonist, an opioid, a carboxylase inhibitor, a partial opioid agonist, a partial nicotinic agonist, and an inhalant. In some embodiments, the at least one other agent is a SSRI selected from paroxetine, sertraline, citalopram, escitalopram, and fluoxetine. In some embodiments, the at least one other agent is a SNRI selected from duloxetine, mirtazapine, and venlafaxine. In some embodiments, the at least one other agent is a NRI selected from bupropion and atomoxetine. In some embodiments, the at least other agent is the NDRI bupropion. In some embodiments, the at least one other agent is the dopamine β-hydroxylase inhibitor disulfuram. In some embodiments, the at least one other agent is the adenosine A2A receptor antagonist istradefylline. In some embodiments, the at least one other agent is a sodium channel blocker selected from lamotrigine, carbamazepine, oxcarbazepine, and valproate. In some embodiments, the at least one other agent is a calcium channel blocker selected from nimodopone, lamotrigine, and carbamazepine. In some embodiments, the at least one other agent is the central and peripheral alpha adrenergic receptor antagonist prazosin. In some embodiments, the at least one other agent is the central alpha adrenergic agonist clonidine. In some embodiments, the at least one other agent is the central or peripheral beta adrenergic receptor antagonist propranolol. In some embodiments, the at least one other agent is an atypical antidepressant/antipsychotic selected from bupropion, olanzepine, risperidone, and quetiapine. In some embodiments, the at least one other agent is a tricyclic selected from amitriptyline, amoxapine, desipramine, doxepin, imipramine, nortriptyline, protiptyline, and trimipramine. In some embodiments, the at least one other agent is an anticonvulsant selected from phenyloin, lamotrigine, carbamazepine, oxcarbazepine, valproate, topiramate, tiagabine, vigabatrin, and levetiracetam. In some embodiments, the at least one other agent is the glutamate antagonist topiramate. In some embodiments, the at least one other agent is a GABA agonist selected from baclofen, valproate, and topiramate. In some embodiments, the at least one other agent is the dopamine metabolism enzyme inhibitor carbidopa. In some embodiments, the at least one other agent is the partial dopamine D2 agonist aripiprazole. In some embodiments, the at least one other agent is an opioid receptor antagonist selected from naltrexone and naloxone. In some embodiments, the at least one other agent is a mood stabilizer selected from carbamazepine and lithium. In some embodiments, the at least one other agent is a direct or indirect dopamine agonist selected from dopamine, bromocriptine, pergolide, amantadine, mazindole, and methylphenidate. In some embodiments, the at least other agent is the partial 5HT1 agonist gepirone. In some embodiments, the at least other agent is the serotonin 5HT2 antagonist ritanserin. In some embodiments, the at least other agent is the opioid methadone. In some embodiments, the at least other agent is the partial opioid agonist buprenorphine. In some embodiments, the at least other agent is the partial nicotinic agonist champix. In some embodiments, the at least one other agent is an inhalant selected from benzene, toluene, o-xylene, m-xylene, p-xylene, ethylbenzene, fluorobenzene, o-difluorobenzene, 1,3,5-trifluorobenzene, 1,2,4-trifluorobenzene, pentafluorotoluene, pentafluorobenzene, and perfluorobenzene. In some embodiments, the methods further include co-administering a therapeutically effective amount of least one other agent selected from benzodiazepine, levodopa, carisprodol, modafenil, acamprosate, gamma-butyrolactone, gamma-hydroxybutyrate, opium, psilopcybin, hallucinogenic mushroom, tobacco, and nicotine. In some embodiments, the Compound A is administered to the patient after a period of abstinence from substance use by the patient. In some embodiments, the therapeutically effective amount of Compound A in the patient is determined by escalating the amount of Compound A administered to the patient until a desired therapeutic response is observed. In some embodiments, the amount of Compound A is tapered off after remission is reached in the patient. In some embodiments, the amount of Compound A is unchanged after remission is reached in the patient.

Also provided are methods of treating at least one phase of cocaine dependence in a patient. In some embodiments, the at least one phase is selected from acquisition, maintenance, extinction, and relapse. The methods include administering to the patient a therapeutically effective amount of Compound A. In some embodiments, the Compound A inhibits the development of the acquisition phase in the patient. In some embodiments, the Compound A promotes development of the extinction phase in the patient. In some embodiments, the Compound A reduces the frequency of relapse in the patient. In some embodiments, the Compound A reduces in the patient at least one symptom of abuse of, dependence on, or withdrawal from cocaine. In some embodiments, the Compound A reduces at least one symptom of cocaine abuse in the patient selected from recurrent cocaine use resulting in a failure to fulfill major role obligations at work, school, or home; recurrent cocaine use in situations in which it is physically hazardous; recurrent cocaine-related legal problems; and continued cocaine use despite having persistent or recurrent social or interpersonal problems caused or exacerbated by the effects of the cocaine. In some embodiments, the Compound A reduces at least one symptom of cocaine dependence in the patient selected from tolerance; withdrawal; the cocaine is often taken in larger amounts or over a longer period then was intended; there is a persistent desire or unsuccessful efforts to cut down or control cocaine use; a great deal of time is spent in activities to obtain the cocaine, use the cocaine, or recover from its effects; important social, occupational or recreational activities are given up or reduced because of cocaine use; and the cocaine use is continued despite knowledge of having a persistent or recurrent physical or psychological problem that is likely to have been caused or exacerbated by the cocaine. In some embodiments, the Compound A reduces at least one symptom of cocaine abuse and dependence selected from attention deficit hyperactivity disorder; euphoria; increased energy, excitement and sociability; less hunger and fatigue; a marked feeling of physical and mental strength; decreased sensation of pain; bronchitis; shortness of breath; chest pain; heart palpitations; arrhythmia; cardiomyopathy; heart attack; dilated pupils; nausea; vomiting; headache; vertigo; dizziness; anxiety; pychosis; confusion; nasal irritation; nasal crusting; recurrent nosebleeds; nasal stuffiness; facial pain; dysphoria; and craving for cocaine. In some embodiments, the Compound A increases at least one negative subjective symptom of cocaine abuse and dependence. In some embodiments, the Compound A reduces at least one symptom of cocaine withdrawal selected from fatigue, lack of pleasure, depression, irritability, sleep disorders, increased appetite, pyschomotor retardation, agitation, extreme suspicion, and craving for cocaine. In some embodiments, the Compound A improves a score of the patient on at least one of ADHD-IV, HAM-D, HAM-A, BDI, apathy scale from Neuropsychiatric Inventory, and a cognitive function rating scale. In some embodiments, the cognitive function rating scale is selected from WAIS-R, WMS-R, RAVLT, Trials I-VII, RCFT, and TMT, Parts A and B. In some embodiments, the Compound A reduces at least one of the amount and frequency of cocaine use by the patient. In some embodiments, the Compound A promotes remission in the patient. In some embodiments, the remission is characterized by at least one of early full remission, early partial remission, sustained full remission, and sustained partial remission. In some embodiments, the Compound A prolongs a period of remission in the patient. In some embodiments, the methods further include treatment with at least one of contingency management and cognitive behavioral therapy. In some embodiments, the methods further include co-administering a therapeutically effective amount of least one other agent selected from a selective serotonin reuptake inhibitor (SSRI), a serotonin-norepinephrine reuptake inhibitor (SNRI), a norepinephrine reuptake inhibitor (NRI), a norepinephrine-dopamine reuptake inhibitor (NDRI), a serotonin 5-hydroxytryptamine1A (5HT1A) antagonist, a dopamine β-hydroxylase inhibitor, an adenosine receptor antagonist, an adenosine A2A receptor antagonist, a monoamine oxidase inhibitor (MAOI), a monoamine oxidase B inhibitor, a sodium channel blocker, a calcium channel blocker, a central and peripheral alpha adrenergic receptor antagonist, a central alpha adrenergic agonist, a central or peripheral beta adrenergic receptor antagonist, a NK-1 receptor antagonist, a corticotropin releasing factor (CRF) antagonist, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, a serotonin 5HT2 antagonist, an opioid, a carboxylase inhibitor, a partial opioid agonist, a partial nicotinic agonist, and an inhalant. In some embodiments, the at least one other agent is a SSRI selected from paroxetine, sertraline, citalopram, escitalopram, and fluoxetine. In some embodiments, the at least one other agent is a SNRI selected from duloxetine, mirtazapine, and venlafaxine. In some embodiments, the at least one other agent is a NRI selected from bupropion and atomoxetine. In some embodiments, the at least other agent is the NDRI bupropion. In some embodiments, the at least one other agent is the dopamine β-hydroxylase inhibitor disulfuram. In some embodiments, the at least one other agent is the adenosine A2A receptor antagonist istradefylline. In some embodiments, the at least one other agent is a sodium channel blocker selected from lamotrigine, carbamazepine, oxcarbazepine, and valproate. In some embodiments, the at least one other agent is a calcium channel blocker selected from nimodopone, lamotrigine, and carbamazepine. In some embodiments, the at least one other agent is the central and peripheral alpha adrenergic receptor antagonist prazosin. In some embodiments, the at least one other agent is the central alpha adrenergic agonist clonidine. In some embodiments, the at least one other agent is the central or peripheral beta adrenergic receptor antagonist propranolol. In some embodiments, the at least one other agent is an atypical antidepressant/antipsychotic selected from bupropion, olanzepine, risperidone, and quetiapine. In some embodiments, the at least one other agent is a tricyclic selected from amitriptyline, amoxapine, desipramine, doxepin, imipramine, nortriptyline, protiptyline, and trimipramine. In some embodiments, the at least one other agent is an anticonvulsant selected from phenyloin, lamotrigine, carbamazepine, oxcarbazepine, valproate, topiramate, tiagabine, vigabatrin, and levetiracetam. In some embodiments, the at least one other agent is the glutamate antagonist topiramate. In some embodiments, the at least one other agent is a GABA agonist selected from baclofen, valproate, and topiramate. In some embodiments, the at least one other agent is the dopamine metabolism enzyme inhibitor carbidopa. In some embodiments, the at least one other agent is the partial dopamine D2 agonist aripiprazole. In some embodiments, the at least one other agent is an opioid receptor antagonist selected from naltrexone and naloxone. In some embodiments, the at least one other agent is a mood stabilizer selected from carbamazepine and lithium. In some embodiments, the at least one other agent is a direct or indirect dopamine agonist selected from dopamine, bromocriptine, pergolide, amantadine, mazindole, and methylphenidate. In some embodiments, the at least other agent is the partial 5HT1 agonist gepirone. In some embodiments, the at least other agent is the serotonin 5HT2 antagonist ritanserin. In some embodiments, the at least other agent is the opioid methadone. In some embodiments, the at least other agent is the partial opioid agonist buprenorphine. In some embodiments, the at least other agent is the partial nicotinic agonist champix. In some embodiments, the at least one other agent is an inhalant selected from benzene, toluene, o-xylene, m-xylene, p-xylene, ethylbenzene, fluorobenzene, o-difluorobenzene, 1,3,5-trifluorobenzene, 1,2,4-trifluorobenzene, pentafluorotoluene, pentafluorobenzene, and perfluorobenzene. In some embodiments, the methods further include co-administering a therapeutically effective amount of least one other agent selected from benzodiazepine, levodopa, carisprodol, modafenil, acamprosate, gamma-butyrolactone, gamma-hydroxybutyrate, opium, psilopcybin, hallucinogenic mushroom, tobacco, and nicotine. In some embodiments, the Compound A is administered to the patient after a period of abstinence from cocaine use by the patient. In some embodiments, the therapeutically effective amount of Compound A in the patient is determined by escalating the amount of Compound A administered to the patient until a desired therapeutic response is observed. In some embodiments, the amount of Compound A is tapered off after remission from cocaine dependence is reached in the patient. In some embodiments, the amount of Compound A is unchanged after remission from cocaine dependence is reached in the patient. In some embodiments, the Compound A treats at least one symptom of abuse of, dependence on, or withdrawal from at least one secondary substance in the patient. In some embodiments, the at least one secondary substance is selected from a drug of abuse and a medication. In some embodiments, the drug of abuse is selected from a psychostimulant agent, an opioid, a hallucinogen, an inhalant, a sedative, a tranquilizer, a hypnotic, an anxiolytic, and an illicit substance. In some embodiments, the psychostimulant agent is a beta-phenylisopropylamine derivative. In some embodiments, the beta-phenylisopropylamine derivative is selected from amphetamine, dextroamphetamine, and methamphetamine. In some embodiments, the psychostimulant agent is selected from ecstasy, phenmetrazine, methylphenidate, diethylpropion, pemoline, mazindol, (−) cathione, and fenfluramine. In some embodiments, the opioid is selected from Lortab, Tramadol, heroin, methadone, hydrocodone, and oxycodone. In some embodiments, the hallucinogen is selected from psilocybin, a hallucinogenic mushroom, lysergic acid diethylamide (LSD), phencyclidine (PCP), and ketamine. In some embodiments, the inhalant is selected from benzene, toluene, o-xylene, m-xylene, p-xylene, ethylbenzene, fluorobenzene, o-difluorobenzene, 1,3,5-trifluorobenzene, 1,2,4-trifluorobenzene, pentafluorotoluene, pentafluorobenzene, and perfluorobenzene. In some embodiments, the medication is selected from an anesthetic, an analgesic, an anticholinergic agent, an antihistamine, a muscle relaxant, a nonsteroidal anti-inflammatory medication, an over the counter medication, and an antidepressant medication. In some embodiments, the drug of abuse is alcohol, caffeine, opium, cannabinoid, cannabis, benzodiazapine, carisprodol, tobacco, nicotine, Vicodin, Lorcet, Percocet, Percodan, and Tylox.

Pharmaceutically acceptable derivatives include acids, bases, enol ethers, and esters, esters, hydrates, solvates, and prodrug forms. The derivative is selected such that its pharmokinetic properties are superior with respect to at least one characteristic to the corresponding neutral agent. The Compound A may be derivatized prior to formulation.

A therapeutically effective amount of Compound A or a pharmaceutically acceptable derivative may vary widely depending on the severity of the addiction or dependence, the age and relative health of the subject, the potency of the compound used and other factors. In certain embodiments a therapeutically effective amount is from about 0.1 milligram per kg (mg/kg) body weight per day to about 50 mg/kg body weight per day. In other embodiments the amount is about 1.0 to about 10 mg/kg/day. Therefore, in certain embodiments a therapeutically effective amount for a 70 kg human is from about 7.0 to about 3500 mg/day, while in other embodiments it is about 70 to about 700 mg/day.

One of ordinary skill in the art of treating such diseases will be able to ascertain a therapeutically effective amount of Compound A for treatment or prevention of addiction or dependence without undue experimentation and in reliance upon personal knowledge and the disclosure of this application. In general, by way of example and without limitation, Compound A will be administered as pharmaceutical compositions by one of the following routes: oral, systemic (e.g., transdermal, intranasal or by suppository) or parenteral (e.g., intramuscular, intravenous or subcutaneous). Compositions can, by way of example and without limitation, take the form of tablets, pills, capsules, semisolids, powders, sustained release formulations, solutions, suspensions, elixirs, aerosols, or any other appropriate composition and are comprised of, in general, Compound A in combination with at least one pharmaceutically acceptable excipient. Acceptable excipients are, by way of example and without limitation, non-toxic, aid administration, and do not adversely affect the therapeutic benefit of the compound. Such excipient may be, for example, any solid, liquid, semisolid or, in the case of an aerosol composition, gaseous excipient that is generally available to one of skill in the art.

Solid pharmaceutical excipients include by way of example and without limitation starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from for example and without limitation water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include by way of example and without limitation water, saline, aqueous dextrose and glycols. Compressed gases may be used to disperse the compound in aerosol form. Inert gases suitable for this purpose are by way of example and without limitation nitrogen, carbon dioxide, nitrous oxide, etc.

The pharmaceutical preparations can by way of example and without limitation, moreover, contain preservatives, solubilizers, stabilizers, wetting agents, emulsifiers, sweeteners, colorants, flavorants, salts for varying the osmotic pressure, buffers, masking agents or antioxidants. In certain embodiments, they can contain still other therapeutically valuable substances. Other suitable pharmaceutical carriers and their formulations are described in A. R. Alfonso *Remington's Pharmaceutical Sciences* 1985, 17th ed. Easton, Pa.: Mack Publishing Company.

The amount of Compound A in the composition may vary widely depending for example, upon the type of formulation, size of a unit dosage, kind of excipients and other factors known to those of skill in the art of pharmaceutical sciences. In general, the final composition will comprise from 10% w to 90% w of the compound, preferably 25% w to 75% w, with the remainder being the excipient or excipients. Preferably the pharmaceutical composition is administered in a single unit dosage form for continuous treatment or in a single unit dosage form ad libitum when relief of symptoms is specifically required.

EXAMPLES

Example 1

Following oral administration of [$^{14}$C]-nepicastat, the majority of the radioactivity in plasma was associated with nepicastat, an N-linked glucuronide of nepicastat (Metabolite 2, M2), and an unidentified polar fraction (M1). There was no significant accumulation of nepicastat with multiple dosing and $T_{1/2}$ was similar after single and multiple doses. $T_{1/2}$ was 10-14 hours. No significant differences in the $C_{max}$ or AUC for nepicastat were noted between subjects with the fast acetylator phenotype and those with the slow acetylator phenotype, although $C_{max}$ and AUC for the N-acetyl metabolite were, as expected, much lower in the slow acetylators than in the fast acetylators. In a study comparing the pharmacokinetics of a 40 mg tablet taken while fasting or after a meal, there was no significant difference in the plasma concentrations. $T_{max}$ was increased to 3.5 hours after a meal from 1.4 hours in the fasted state.

The pharmacokinetics of nepicastat after a single 40 mg dose was compared in men and women. The AUC in women was approximately 43% greater than in men and the $C_{max}$ approximately 23% greater in women than in men. The T½ was longer in women than in men. Comparing the pharmacokinetics of nepicastat following 10 days of dosing with a 40 mg dose, the AUC was higher in healthy subjects than in patients with CHEF, with no difference in the T½. There was no significant accumulation with multiple dosing in either population.

In humans, compound-related radioactivity is rapidly eliminated. On average, 87.4% of the administered radiolabel was recovered in the first 72 hours with 82.4% in the urine and 5.01% in the feces. After 10 days, the mean total recovery of the radiolabel was 93.8%. In plasma, the Tax, for the radioactivity was 1-2 hours (similar to that for nepicastat). In both rapid and slow acetylators, an N-linked glucuronide of nepicastat accounted for the greatest percentage of the total radioactivity in plasma (26.8%) and urine (57.9%) over 0 to 48 hours. The terminal T1/2 for total radioactivity in plasma was found to be very long (~100 hours), most likely due to a polar fraction present in low concentrations that was slowly eliminated.

Example 2

In a study designed to assess the effects of nepicastat on cognitive function, subjects treated with 5 or 40 mg of nepicastat demonstrated no significant impairment of mood, sleep, or cognition. In studies of thyroid uptake of $^{123}$I, doses of 5, 40, and 100 mg of nepicastat demonstrated no differences from placebo. Reduction of uptake after a single 200 mg dose of nepicastat was significantly greater than placebo, but significantly less than that following a 10 mg dose of methimazole. In single-dose Phase I studies, doses from 5 to 800 mg (dose calculation based on the hydrochloride salt) of nepicastat were generally well tolerated in healthy men.

Example 3

In a multiple-dose Phase I study of nepicastat, doses of 5 and 40 mg were generally well tolerated in healthy men.

Five of the 6 subjects treated for 8 days or longer with 200 mg developed a rash which resolved spontaneously.

One subject developed atrial arrhythmias and intermittent right bundle branch block after 6 days of dosing with 200 mg of nepicastat.

Example 4

Sixteen non-treatment-seeking cocaine-dependent volunteers are studied as inpatients using a double-blind, placebo-controlled, within-subjects design. After giving informed consent, potential volunteers complete outpatient psychiatric and medical screening. Eligible volunteers are admitted and a physical examination, EKG, pregnancy testing and psychiatric testing are completed. The study utilizes a dose-escalation design in which participants (n=12) receive ascending doses of cocaine (0 mg, 10 mg, 20 mg, and 40 mg) during daily treatment with ascending doses of nepicastat (0 mg, 80 mg, 160 mg). A parallel group of participants (n=4) receive only daily treatment with placebo for the duration of the study in order to maintain the blind. Treatment at each dose level are daily for 4 days, or well over 4 half-lives of nepicastat, which is 10 to 14 hours. On the 4$^{th}$ day of treatment at each dose level, participants receive cocaine 0 mg, 10 mg, 20 mg, and 40 mg in that order. Cocaine is administered at hourly intervals, providing sufficient time for both the cardiovascular and subjective effects to return to baseline. Cardiovascular indices are carefully monitored using continuous EKG and frequent blood pressure during all procedures involving the administration of cocaine, and stopping parameters are in place so that cocaine is not be administered if cardiovascular indices exceed preset limits. Previous studies have shown that 6 doses of 32 mg cocaine given at 14-minute intervals is safe, and extending the inter-dose interval to 1 hour may enhance safety further. Blood samples are collected for analysis of the pharmacokinetics of 10 mg cocaine administered on the $3^{rd}$ day of treatment with 0 mg nepicastat and again on the $3^{rd}$ day of treatment with 80 mg and 160 mg nepicastat. The effects of nepicastat on the pharmacokinetics of cocaine are studied. Based on existing information, no interaction is expected.

About 12 days are required for each participant to complete the study. The 16 participants may complete the study within one year.

In order to participate in the study, participants must:
1. Be English-speaking volunteers who are not seeking treatment at the time of the study;
2. Be between 18-55 years of age;
3. Meet DSM-IV TR criteria for cocaine dependence;
4. Have a self-reported history of using cocaine by the IV route and provide at least one cocaine-positive urine prior to admission;
5. Have vital signs as follows: resting pulse between 50 and 95 bpm, blood pressures between 85-150 mm Hg systolic and 45-96 mm Hg diastolic; this criterion must be met within 2 days of admission;
6. Have hematology and chemistry laboratory tests that are within normal (+/−10%) limits with the following exceptions: a) liver function tests (total bilirubin, ALT, AST, and alkaline phosphatase)≤3× the upper limit of normal, and b) kidney function tests (creatinine and BUN)≤2× the upper limit of normal;
7. Have a baseline EKG that demonstrates clinically normal sinus rhythm, clinically normal conduction, and no clinically significant arrhythmias;
8. Have a medical history and brief physical examination demonstrating no clinically significant contraindications for study participation, in the judgment of the admitting physician and the principal investigator.

Potential participants are excluded from participation in the study if any of the following apply:
1. Have any history or evidence suggestive of seizure disorder or brain injury;
2. Have any previous medically adverse reaction to cocaine, including loss of consciousness, chest pain, or epileptic seizure;
3. Have neurological or psychiatric disorders, such as:
   psychosis, bipolar illness or major depression as assessed by SCID;
   organic brain disease or dementia assessed by clinical interview;
   history of any psychiatric disorder which would require ongoing treatment or which would make study compliance difficult;
   history of suicide attempts within the past three months assessed by SCID and/or current suicidal ideation/plan as assessed by SCID;
4. Have evidence of clinically significant heart disease or hypertension, as determined by the PI, though participants may be taking antihypertensive medication;
5. Have a family history in first-degree relatives of early cardiovascular morbidity or mortality, as determined by the PI;
6. Have evidence of untreated or unstable medical illness including: neuroendocrine, autoimmune, renal, hepatic, or active infectious disease;
7. Have HIV and are currently symptomatic, have a diagnosis of AIDS, or are receiving antiretroviral medication;
8. Be pregnant or nursing. Other females must either be unable to conceive (i.e., surgically sterilized, sterile, or post-menopausal) or be using a reliable form of contraception (e.g., abstinence, birth control pills, intrauterine device, condoms, or spermicide). All females must provide negative pregnancy urine tests before study entry, upon hospital admission, and at the end of study participation;
9. Have asthma or currently use alpha or beta agonists, theophylline, or other sympathomimetics;
10. Have any other illness, condition, or use of psychotropic medications, which in the opinion of the PI and/or the admitting physician would preclude safe and/or successful completion of the study.

Criteria for Discontinuation Following Initiation
11. Positive urine drug screen or breath test indicating illicit use of cocaine, cocaine, alcohol, opiates, or other abused drugs not delivered as part of this protocol;
12. Inability to comply with study procedures;
13. Meet discontinuation criteria due to exaggerated response to cocaine, described below.

Stopping Criteria

Participants must continue to meet inclusion criteria in order to remain in the protocol. Cocaine administration is not initiated if there are clinically significant arrhythmias or if vital signs are outside of acceptable ranges: resting pulse <130 bpm and blood pressure below 165 mm Hg systolic and 100 mm Hg diastolic. These values are higher than those of the inclusion/exclusion criteria because transient increases in vital signs can occur in expectation of receiving cocaine. In addition, repeated doses of cocaine are not administered (and the study physician halts continued cocaine delivery) if there are behavioral manifestations of cocaine toxicity (agitation, psychosis, inability to cooperate with study procedures).

Stopping Criteria for Further Participation

Subject participation is terminated if any of the following events occur:
1. Systolic BP>180 mm Hg sustained for 5 minutes or more;
2. Diastolic BP>120 mm Hg sustained for 5 minutes or more;
3. Heart rate >(220−age×0.85) bpm sustained for 5 minutes or more.

Rationale for Subject Selection Criteria

Participants are required to have used cocaine by the IV route to avoid exposing participants to routes of administration that produce more intensive interoceptive effects. The age criteria were selected primarily to avoid enrolling participants with undiagnosed cardiovascular disease. Participants with active HIV disease are excluded to avoid potential exacerbation of their underlying disease; participants with asymptomatic HIV are included because this group is at high risk for cocaine dependence. Participants with asthma (or who take asthma medications) are excluded due to potential adverse interactions between beta agonist medications and cocaine.

Study Medications

Cocaine produces prototypical stimulant effects by inhibiting the uptake of DA, NE, and serotonin into presynaptic storage granules. Cocaine has a short elimination half-life, about 90 min. The principal clinical effects of cocaine are psychomotor activation and increases in sympathetic tone, evident as increases in heart rate and blood pressure.

Cocaine is administered at up to 40 mg in single doses and up to 200 mg in self-administration sessions consisting of 10 doses of 20 mg administered at 13 min intervals. These doses are modest compared to amounts that participants in these studies have reported using daily; typical daily dosing patterns are on average 250 mg to 500 mg or more.

Doses much higher than those proposed here have been associated with seizures and with severe cardiovascular toxicity and death. These potential toxicities are ameliorated by the use of relatively low doses, careful screening of potential volunteers, by careful monitoring of participants following administration of cocaine, and by the ready availability of medical intervention in the case of an adverse event.

Cocaine is administered IV, so availability is complete. Cocaine is metabolized primarily to benzoylecgonine by plasma esterases that are not known to be affected by nepicastat. Benzyoleconine and other minor metabolites are excreted renally.

Cocaine for IV use in humans is obtained from a NIDA contractor and a letter of authorization to allow us to reference NIDA's IND for cocaine is obtained and submitted to the FDA.

Ascending doses of nepicastat (0 mg, 80 mg, and 160 mg) are administered at 7 AM. Treatment at each dose level is continued for 4 days.

By starting at a lower dose and increasing the dose after completing the first series of study procedures, the risks of the combination of nepicastat and cocaine are be minimized. This approach also may reduce the risk for rash, which occurred in 7% to 20% of volunteers thus far. Rash incidence was associated with dose and treatment duration. Doses above 160 mg conferred a greater risk for rash.

No pharmacokinetic interactions are expected because nepicastat is not an enzyme inhibitor, though pharmacokinetic assessment of the 10 mg does of cocaine administered on the $3^{rd}$ day of treatment at each dose level of nepicastat can confirm this. Because nepicastat reduces the synthesis of NE, the rewarding effects of cocaine may be lower during treatment with nepicastat. Because nepicastat increases plasma and brain concentrations of DA, DA-mediated side effects such as paranoia may occur. These symptoms were not observed during the trials for CHF, but stimulants were not administered in those studies.

Following consent, participants are required to submit a cocaine-positive urine sample for documentation of ongoing drug use. Some participants (limited by the number of devices available) are also asked to wear a telemetry device during screening and throughout the study that records heart rate and movement. Data from this device can identify drug use episodes based on changes in these parameters.

To control nicotine exposure, smoking is prohibited within 2 hours of study procedures involving cocaine administration or cue exposure. Participants are required to refrain from illicit and prescription drug use for the duration of the study and this is confirmed with daily urine and breath alcohol level testing.

Experimental sessions are conducted at approximately the same time of day for a given participant. Cocaine is administered in an experimental room. Cocaine is administered using a syringe pump, which administers the correct dose of cocaine or saline placebo over 2 minutes. During and for 1 hour after drug administration sessions heart rate and blood pressure are monitored.

Participants undergo a targeted history and physical examination. Blood is drawn for standard laboratory examination, including CBC, electrolytes, LFT, and creatinine HIV screening is performed as a service to participants and those testing positive are counseled and referred for treatment.

The Actiheart MiniMitter is used to measure heart rate and movement prior to admission in some volunteers (the number is limited by the number of devices available). The MiniMitter attaches to the participants' skin using paste and non-invasively records EKG and movement for up to two weeks. The data can be downloaded to a PC for analysis later.

Participants must meet DSM-IV-TR criteria for cocaine and nicotine dependence, determined by the Mini International Neuropsychiatric Interview (MINI) and defined by inclusion/exclusion criteria. The MINI is a short, structured diagnostic interview developed in 1990 by psychiatrists and clinicians in the United States and Europe for DSM-IV TR and ICD-10 psychiatric disorders. The MINI is the structured psychiatric interview of choice for psychiatric evaluation and outcome tracking in clinical psychopharmacology trials and epidemiological studies, and is the most widely used psychiatric structured diagnostic interview instrument in the world. This instrument can be used to determine whether the subject met DSM-IV TR criteria for drug dependence and to rule out any major psychiatric disorders (e.g., affective disorders, schizophrenia).

The Addiction Severity Index-Lite Clinical Factors (ASI-Lite CF) version is administered by a trained research staff member during screening. The ASI-Lite is the interviewer's estimate of the severity of the participant's status in seven areas (medical, employment, drug use, alcohol use, legal, family/social, and psychological). The Lite version is a shorter version of the ASI that still retains all questions used to calculate the ASI composite scores. The family history section of the ASI, as the ASI-Lite version collects minimal family history information, are retained.

There is a third-generation Beck Depression Inventory (BDI), revised in 1996. The instrument retains its original 21-item questionnaire format that requires approximately 10 minutes to complete. The BDI-II has been validated against the BDI-IA and continues to be an excellent index of depression/distress. This indicator is used to monitor participants who become clinically depressed during the trial, making it also a measure for participants' safety.

Current attention deficit hyperactivity disorder (ADHD) symptoms are assessed weekly, using the ADHD-IV rating scale.

The apathy scale from the Neuropsychiatric Inventory are collected at baseline.

DNA is collected with buccal swabs applied to Whatman FTA cards. These cards allow safe and stable storage of biological samples for DNA extraction. The anticipated yield of genomic DNA is 50-100 μg, which is adequate for over 500 genotype assays using currently available methods.

Genotypes are determined using 5' Exonuclease-based (Taqman) genotyping assays. Assays are developed by Applied Biosystems (ABI; Assays by Design). Allele discrimination are performed using the ABI 3730 realtime PCR cycler.

Blood samples for analysis of the pharmacokinetics of cocaine are collected during treatment with 0 mg nepicastat (study day 1) and during treatment with 80 mg and 160 mg nepicastat (study days 4 and 8). Blood samples are collected at −15, 20, 30, 40, 50, 60, 90, 120, 180, 240, 300, 360, 420 and 480 minutes following dosing of 10 mg cocaine on the $3^{rd}$ day of treatment with each dose level of nepicastat. Note that other doses of cocaine (0-40 mg) are administered on the $4^{th}$ day of treatment with each dose level of nepicastat, so the pharmacokinetic assessment does not interfere with the other assessments. Blood is collected and plasma separated and frozen at −70° C. until analyzed. Cocaine and BE are assayed using liquid chromatography/tandem mass spectrometry (LC/MS/MS). The reference lab has a limit of quantification of 2.5 ng/ml for these assays. The pharmacokinetic analysis clarifies effects of nepicastat on the pharmacokinetics of cocaine.

DBH is stored in NE storage granules and is released along with NE. Plasma DBH thus gives a good index of enzymatic activity within the CNS. Blood is sampled daily at 10 AM (prior to cocaine/placebo dosing) and stored for subsequent analysis. DBH activity is measured by using the tyramine-octopamine method using a high performance liquid chromatographic-fluorometric system, as described previously. This allows examination of changes in DBH over time, providing an insight into the pharmacodynamics of nepicastat's inhibition of DBH. The BDI is administered repeatedly throughout the protocol to monitor changes in mood.

Subjective effects are measured using a computerized visual analogue scale (VAS) consisting of a continuous 10 cm line digitized for scoring purposes from 0 to 100. Participants are required to move the cursor from off the left-hand extreme and onto the line by depressing the left or right mouse buttons for left and right movements on the line. The VAS is designed to provide rapidly acquired ratings of cocaine euphoria, dysphoria and craving. These include ratings of "Any Drug Effect," "High," "Good Effects," "Stimulated," and "Bad Effects," "Feel Paranoid," "Feel Suspicious," and "Would Use Cocaine if Available," "Crave Cocaine," "Could Refuse Cocaine Now," and "Desire Cocaine." VAS measures are collected prior to cocaine administration and at 5, 10, 15, 20, 30, and 45 minutes following drug administration.

Fifteen minutes after cocaine administration participants are asked how much they would pay for that dose of drug, based on $50/gm (current cost if purchases from illicit sources). This anchor is provided to standardize responses given that the price of cocaine varies over time and place.

On Day 13, the last day of treatment with study medication, all patients participate in the "Experimental Sessions" where subjects make a series of choices between money and a double blinded infusion of placebo (saline) or 20 mg cocaine. In one of the sessions, only placebo (saline) is available. In the other session, only 20 mg cocaine is available. Participants choose to either self-administer placebo or accept money and 20 mg cocaine vs. money. This occurs in the morning (am) and in the afternoon (pm), with the order randomized and counterbalanced so that placebo or nepicastat is administered first to equal numbers of subjects.

Experimental (Choice) Session:

During each session subjects are asked to make a series of choices between an infusion corresponding to a color ("blue" or "green"), and money. The color corresponds to the dose (cocaine 0 mg or 20 mg) administered to the subject during the sample session. For each of the 2 choice sessions, participants make 10 choices for the infusion (cocaine 0 mg IV in one session and cocaine 20 mg in the other) or money. The participant makes a series of choices between ascending value money options ($0.05, $0.05, $0.05, $0.05, $1, $4, $7, $10, $13, and $16) or cocaine (0 mg or 20 mg/IV/infusion) using a patient-controlled analgesia (PCA) pump.

Infusion choices are performed by the participant using the PCA button, while choices for money are indicated verbally to the investigator. Infusions take place over 2-min followed by a 3-min time-out period. As such, selections are made at 5-min intervals.

Participants receive cocaine doses immediately after indicating their choice, providing vital signs remain within preset limits up to a maximum of 200 mg cocaine (10×20 mg). Money choices are given directly to the patient immediately after the choice, but this money must be spent prior to discharge.

The table shows the Experimental choice sessions with 16 total participants.

| | Choices | 8 participants | 8 participants |
|---|---|---|---|
| am | Choice 1 | 0 mg cocaine IV or $0.05 | 20 mg cocaine IV or $0.05 |
| am | Choice 2 | 0 mg cocaine IV or $0.05 | 20 mg cocaine IV or $0.05 |
| am | Choice 3 | 0 mg cocaine IV or $0.05 | 20 mg cocaine IV or $0.05 |
| am | Choice 4 | 0 mg cocaine IV or $0.05 | 20 mg cocaine IV or $0.05 |
| am | Choice 5 | 0 mg cocaine IV or $1.00 | 20 mg cocaine IV or $1.00 |
| am | Choice 6 | 0 mg cocaine IV or $4.00 | 20 mg cocaine IV or $4.00 |
| am | Choice 7 | 0 mg cocaine IV or $7.00 | 20 mg cocaine IV or $7.00 |
| am | Choice 8 | 0 mg cocaine IV or $10.00 | 20 mg cocaine IV or $10.00 |
| am | Choice 9 | 0 mg cocaine IV or $13.00 | 20 mg cocaine IV or $13.00 |
| am | Choice 10 | 0 mg cocaine IV or $16.00 | 20 mg cocaine IV or $16.00 |
| pm | Choice 1 | 20 mg cocaine IV or $0.05 | 0 mg cocaine IV or $0.05 |
| pm | Choice 2 | 20 mg cocaine IV or $0.05 | 0 mg cocaine IV or $0.05 |
| pm | Choice 3 | 20 mg cocaine IV or $0.05 | 0 mg cocaine IV or $0.05 |
| pm | Choice 4 | 20 mg cocaine IV or $0.05 | 0 mg cocaine IV or $0.05 |
| pm | Choice 5 | 20 mg cocaine IV or $1.00 | 0 mg cocaine IV or $1.00 |
| pm | Choice 6 | 20 mg cocaine IV or $4.00 | 0 mg cocaine IV or $4.00 |
| pm | Choice 7 | 20 mg cocaine IV or $7.00 | 0 mg cocaine IV or $7.00 |
| pm | Choice 8 | 20 mg cocaine IV or $10.00 | 0 mg cocaine IV or $10.00 |
| pm | Choice 9 | 20 mg cocaine IV or $13.00 | 0 mg cocaine IV or $13.00 |
| pm | Choice 10 | 20 mg cocaine IV or $16.00 | 0 mg cocaine IV or $16.00 |

A sample size of 12 in the nepicastat-treated group allows detection of medium to large effects, which is appropriate for an initial assessment. The plot (FIG. 1) shows the effect size achieved with sample sizes ranging from 5 to 15. Increasing the sample size above 12 would enhance analytical power to detect differences between the treatments but at increasing cost. The placebo-treated group is included only to maintain the blind and is not intended to serve as a comparison group.

The analysis focuses primarily on the effects of nepicastat in the nepicastat-treated group. The placebo-treated group is included primarily to maintain the blind. Side effects and adverse events (AEs) are tabulated and compared across treatment conditions using ANOVA or Chi-square. Subjective and cardiovascular effects produced by IV cocaine and placebo during treatment with nepicastat are compared to those produced during treatment with placebo using repeated measures (time being the repeated measure) analysis of variance (ANOVA), peak effect one-way ANOVA, and if indicated, area under the curve ANOVA.

Example 5

Bovine and human dopamine β-hydroxylase activity were assayed by measuring the conversion of tyramine to octopamine. Bovine adrenal dopamine β-hydroxylase was obtained from Sigma Chemicals (St Louis, Mo., USA) whereas human dopamine β-hydroxylase was purified from the culture medium of the neuroblastoma cell line SK-N-SH. The assay was performed at pH 5.2 and 32° C. in a medium containing 0.125 M NaAc, 10 mM fumarate, 0.5-2 μM $CuSO_4$, 0.1 mg·$ml^{-1}$ catalase, 0.1 mM tyramine and 4 mM ascorbate. In a typical assay, 0.5-1 milliunits of enzyme were added to the reaction mixture and, subsequently, a substrate mixture containing catalase, tyramine and ascorbate was added to initiate the reaction (final volume of 200 μl). Samples were incubated with or without the appropriate concentration of nepicastat or Compound B at 37° C. for 30 to 40 minutes. The reaction was quenched by the stop solution containing 25 mM EDTA and 240 μM 3-hydroxy-tyramine (internal standard). The samples were analyzed for octopamine by reverse phase high pressure liquid chromatography (HPLC) using ultraviolet-detection at 280 nM. The HPLC chromatography run was carried out at the flow rate of 1 ml·min$^{-1}$ using a LiChroCART 125-4 RP-18 column and isocratic elution with 10 mM acidic acid, 10 mM 1-heptane sulfonic acid, 12 mM tetrabutyl ammonium phosphate and 10% methanol. The remaining percent activity was calculated based on controls, corrected using internal standards and fitted to a non-linear four-parameter concentration-response curve.

Nepicastat (S-enantiomer) and Compound B (R-enantiomer) produced concentration-dependent inhibition of bovine and human dopamine β-hydroxylase activity. The calculated $IC_{50}$'s for nepicastat were 8.5±0.8 nM and 9.0±0.8 nM for the bovine and human enzyme, respectively. Compound B was slightly less potent ($IC_{50}$'s of 25.1±0.6 nM and 18.3±0.6 nM for the bovine and human enzyme, respectively) than nepicastat. Nepicastat was shown to be a potent inhibitor of human and bovine dopamine β-hydroxylase in vitro. The inhibitory effects of the compound were stereospecific since the S-enantiomer (nepicastat) was marginally, but significantly, more potent than the R-enantiomer (Compound B).

The activity of nepicastat at twelve selected enzymes and receptors was determined using established assays. A brief account of the principle underlying each of the enzymatic assays is given in FIG. 2. Binding data were analyzed by iterative curve-fitting to a four parameter logistic equation. Ki values were calculated from $IC_{50}$ values using the Cheng-Prusoff equation. Enzyme inhibitory activity was expressed as $IC_{50}$ (concentration required to produce 50% inhibition of enzyme activity).

Nepicastat had negligible affinity ($IC_{50}$s or K is >10 μM) for a range of other enzymes (tyrosine hydroxylase, acetyl CoA synthetase, acyl CoA-cholesterol acyl transferase, $Ca^{2+}$/calmodulin protein kinase II, cyclooxygenase-I, HMG-CoA reductase, neutral endopeptidase, nitric oxide synthase, phosphodiesterase III, phospholipase $A_2$, and protein kinase C) and neurotransmitter receptors ($\alpha_{1A}$, $\alpha_{1B}$, $\alpha_{2A}$, $\alpha_{2B}$, $\beta_1$ and $\beta_2$ adrenoceptors, $M_1$ muscarinic receptors, $D_1$ and $D_2$ dopamine receptors, μ opioid receptors, $5\text{-HT}_{1A}$, $5\text{-HT}_{2A}$, and $5\text{-HT}_{2C}$ serotonin receptors). Nepicastat displayed a high degree of selectivity for dopamine β-hydroxylase as the compound possessed negligible affinity for twelve other enzymes and thirteen neurotransmitter receptors.

In studies involving SHRs, the drugs, nepicastat ((S)-5-aminomethyl-1-(5,7-difluoro-1,2,3,4-tetrahydronaphth-2-yl)-1,3-dihydroimidazole-2-thione hydrochloride) and the corresponding R-enantiomer (Compound B), were dissolved in distilled water and dosed orally with a gavage needle. In the dog studies, the drugs were filled in capsules and dosed orally. All doses are expressed as free base equivalents.

Male SHRs (15-16 weeks old, Charles River, Wilmington, Mass., USA) were used in in vivo studies. On the day of the study, animals were weighed and randomly assigned to be dosed with either vehicle (control) or the appropriate dose of nepicastat (3, 10, 30 or 100 mg·kg$^{-1}$, po) or Compound B (30 mg·kg$^{-1}$, po) three consecutive times, twelve hours apart. At six hours after the third dose, the rats were anaesthetized with halothane, decapitated and tissues (cerebral cortex, mesenteric artery and left ventricle) were rapidly harvested, weighed, placed in iced perchloric acid (0.4 M), frozen in liquid nitrogen and stored at −70° C. until subsequent analysis. To quantify noradrenaline and dopamine concentrations, tissues were homogenized by brief sonication and centrifuged at 13,000 rpm for 30 minutes at 4° C. The supernatant, spiked with 3,4-dihydroxybenzylamine (internal standard), was assayed for noradrenaline and dopamine by HPLC using electrochemical detection.

Basal tissue catecholamine content (μg·g$^{-1}$ wet weight) in control animals were as follows: mesenteric artery (noradrenaline, 10.40±1.03; dopamine, 0.25±0.02), left ventricle (noradrenaline, 1.30±0.06; dopamine, 0.02±0.00) and cerebral cortex (noradrenaline, 0.76±0.03; dopamine, 0.14±0.01). Nepicastat produced dose-dependent reduction in noradrenaline content and enhancement of dopamine content and dopamine/noradrenaline ratio in the three tissues which were studied.

These changes attained statistical significance (p<0.05) at doses of ≥3 mg·kg$^{-1}$ in the mesenteric artery and left ventricle but only at doses of 30 and 100 mg·kg$^{-1}$ in the cerebral cortex. At the highest dose studied (100 mg·kg$^{-1}$, po), the decreases in noradrenaline were 47%, 35%, 42% and increases in dopamine were 820%, 800% and 86% in the mesenteric artery, left ventricle and cerebral cortex, respectively. When tested at 30 mg·kg$^{-1}$, po, nepicastat produced significantly greater changes in catecholamine content, as compared to the R-enantiomer (Compound B), in the mesenteric artery and left ventricle.

Male beagle dogs (10-16 kg, Marshall Farms USA Inc, North Rose, N.Y., USA) were also used in in vivo studies. On the day of the study, dogs were weighed and randomly assigned to be orally dosed with either empty capsules (control) or the appropriate dose of nepicastat (0.05, 0.5, 1.5 or 5 mg·kg$^{-1}$; po, b.i.d.) for 5 days. At six hours following the first dose on day-5, the dogs were euthanized with pentobarbital and the tissues (cerebral cortex, renal artery, left ventricle) were rapidly harvested. The tissues were subsequently processed and analyzed for noradrenaline and dopamine.

Data are expressed as mean±standard error of the mean (SEM). Tissue and plasma catecholamine data were analyzed using a non-parametric one-way analysis of variance (ANOVA) or two-way ANOVA, respectively, followed by pairwise comparison using Fisher LSD test. P<0.05 was considered statistically significant.

Basal tissue catecholamine content (μg·g$^{-1}$ wet weight) in control animals were as follows: renal artery (noradrenaline, 10.7±1.05; dopamine, 0.22±0.01), left ventricle (noradrenaline, 2.11±0.18; dopamine, 0.07±0.03) and cerebral cortex (noradrenaline, 0.26±0.02; dopamine, 0.03±0.00). When compared to control animals, nepicastat produced a dose-dependent reduction in noradrenaline content and enhancement of dopamine content and dopamine/noradrenaline ratio in the three tissues which were studied.

These changes attained statistical significance (p<0.05) at doses of ≥0.1 mg·kg$^{-1}$·day$^{-1}$ in the three tissues. At the highest dose studied (5 mg·kg$^{-1}$, b.i.d., po), the decreases in noradrenaline were 88%, 91% and 96% and increases in dopamine were 627%, 700% and 166% in the renal artery, left ventricle and cerebral cortex, respectively.

Male beagle dogs were randomized to be orally dosed with either empty capsules (control) or nepicastat (2 mg·kg$^{-1}$, po, b.i.d.) for 15 days. Daily venous blood samples were drawn, six hours after the first dose, for measurement of plasma concentrations of dopamine and noradrenaline. The samples were collected in tubes containing heparin and glutathione, centrifuged at −4° C. and the separated plasma was stored at −70° C. until analysis. The baseline concentrations of catecholamines in two groups of animals were not significantly different from each other: plasma noradrenaline and dopamine concentrations were 460.3±59.6 and 34.4±11.9 pg·ml$^{-1}$, respectively, in the control group and 401.9±25.5 and 41.1±8.8 pg·ml$^{-1}$, respectively, in the nepicastat-treated group. When compared to the control group, nepicastat (2 mg·kg$^{-1}$, b.i.d, po) produced significant decreases in plasma concentrations of noradrenaline and increases in plasma concentrations of dopamine and dopamine/noradrenaline ratio.

Inhibitory modulation of sympathetic nerve function, through pharmacological means, is an attractive therapeutic strategy for the management of congestive heart failure, inasmuch as elevated activity of this system has been implicated in the progressive worsening of the disease. The aim of this study was to pharmacologically characterize the effects of nepicastat, a compound which modulates noradrenaline synthesis in sympathetic nerves by inhibiting the enzyme dopamine β-hydroxylase.

Inhibition of dopamine β-hydroxylase in vivo would be expected to result in elevated levels of the substrate (dopamine) and diminished levels of the product (noradrenaline) in tissues which receive noradrenergic innervation. This expectation was borne out in experiments which investigated the effects of nepicastat on catecholamine levels in central and peripheral tissues in vivo. In both SHRs and beagle dogs, nepicastat produced dose-dependent reductions in noradrenaline content and increases in dopamine content in peripheral (mesenteric or renal artery, left ventricle) and central (cerebral cortex) tissues. In this respect, Compound B was less potent than nepicastat which is consistent with the lower $IC_{50}$ of the former enantiomer for the enzyme. Although dopamine/noradrenaline ratio was also elevated, there did not appear to be stoichiometric replacement of noradrenaline with dopamine. The most likely explanation for this finding is that tissue levels of dopamine may have been underestimated due to intraneuronal metabolism of dopamine.

The ability of nepicastat to alter catecholamine levels in the cerebral cortex suggests that the drug does penetrate the blood brain barrier. In dogs, the magnitude of the changes in catecholamines in the cerebral cortex appeared comparable to those in peripheral tissues. In SHRs, however, nepicastat, at low doses (≤10 mg·kg$^{-1}$), produced significant changes in noradrenaline and dopamine content in peripheral tissues without affecting catecholamines in the cerebral cortex. This suggests that, at least in SHRs, the drug does possess modest peripheral selectivity.

Plasma noradrenaline concentrations provide a useful measure of overall sympathetic nerve activity although this parameter may be influenced by alterations in neuronal uptake and metabolic clearance of the catecholamine. Baseline concentrations of noradrenaline in the plasma were surprisingly elevated in the dogs and is, perhaps, a reflection of the initial stress induced by the phlebotomy blood-sampling procedure. Nevertheless, compared to the control group, nepicastat produced significant decreases in plasma noradrenaline concentrations consistent with reduced transmitter synthesis and release although an indirect effect, secondary to facilitation of neuronal uptake or metabolic clearance, cannot be discounted. Since released noradrenaline represents a small fraction of the total neuronal noradrenaline stores, an inhibitor of noradrenaline biosynthesis would affect noradrenaline release only after existing stores of the catecholamine have been sufficiently depleted. Accordingly, the decreases in plasma noradrenaline concentrations did not attain statistical significance until 4 days of dosing with nepicastat suggesting gradual modulation of the sympathetic nervous system.

A growing body of evidence suggests that chronic activation of the sympathetic nervous system in congestive heart failure is a maladaptive response. This contention is supported by clinical trials which have shown a beneficial effect of carvedilol in congestive heart failure patients with respect to long-term morbidity and mortality. However, it should be noted that most patients do require some level of sympathetic drive to support cardiovascular homeostasis. Indeed, the therapeutic value of β-blockers, including carvedilol, may be limited by their propensity to cause hemodynamic deterioration especially during initiation of therapy. This unwanted effect, which results from abrupt withdrawal of sympathetic support, necessitates careful dose-titration. Inhibitors of dopamine β-hydroxylase, such as nepicastat, may be devoid of this undesirable effect for the following reasons. First, this class of drugs would attenuate, but not abolish, noradrenaline release and, second, they produce gradual modulation of the system thereby obviating the need for dose-titration. Another advantage of nepicastat over β-blockers is that it enhances dopamine levels which, via agonism of dopamine receptors, may have salutary effects on renal function such as renal vasodilation, diuresis and natriuresis.

Nepicastat is a potent, selective and orally active inhibitor of dopamine β-hydroxylase which may be of value in the treatment of cardiovascular disorders associated with over-activation of the sympathetic nervous system.

Example 6

The preparation of nepicastat was based upon the chiral reduction of tetralone 3 (available from the $AlCl_3$-catalyzed Friedel-Crafts reaction of 3,5-difluorophenylacetyl chloride with ethylene in $CH_2Cl_2$ at −65° C.) under the conditions described by Terashima (LAH, (−)-1R,2S—N-methylephedrine, 2-ethylaminopyridine) to give R-(+)-tetralol 4a (92-95% ee), that was converted to the R-(+)-mesylate, followed by reaction with sodium azide afforded a mixture (9:1) of azide and dihydronaphthalene 7. The azide was hydrogenated and the product treated with anhydrous HCl to give S-(−)-amine hydrochloride, converted by a Strecker reaction (formaldehyde bisulfite complex and KCN) to S-(−)-aminonitrile. Formation of the heterocycle was accomplished by sequential diformylation of aminonitrile followed by subsequent treatment with thiocyanic acid. Competing hydrolysis of the nitrile afforded comparable amounts of the primary amide. Reduction of nitrile to amine (93-96% ee) was accomplished using LAH in THF. The enantiomer (91.6% ee) was available by the same above described route using (+)-1S,2R—N-methylephedrine as a chiral auxiliary in the Terashima reduction of ketone. The absolute configuration of the chiral center was based upon literature precedence of the previously described S-(−)-2-tetralol.

Melting points were determined on a Uni-Melt Thomas Hoover Capillary Melting Point Apparatus or a Mettler FB 81HT cell with a Mettler FP90 processor and are uncorrected. Mass spectra were obtained with either a Finnigan MAT 8230 (for electron-impact or chemical ionization) or Finnigan MAT TSQ70 (for LSIMS) spectrometer. $^1$H NMR spectra were recorded on a Bruker ACF300, AM300, AMX300 or EM390 spectrometer and chemical shifts are given in ppm (δ) from tetramethylsilane as internal standard. IR spectra were recorded on a Nicolet SPC FT-IR spectrometer. UV spectra were recorded on a Varian Cary 3 UV- Visible spectrometer, Leeman Labs Inc. Optical rotations were measured in a Perkin-Elmer Model 141 polarimeter. Chiral HPLC measurements were performed on a Regis Chiral AGP column (4.6×100 mm) eluting with 2% acetonitrile-98% 20 mM $KH_2PO_4$ (pH 4.7) at 1 mL/min at 20° C.

5,7-Difluoro-2-tetralone. $SOCl_2$ (100 mL) was added in one portion to 3,5-difluorophenylacetic acid (100 g, 0.58 mol) and after stirring for 15 h, the volatiles were evaporated under reduced pressure. The resulting oily acid chloride was dissolved in $CH_2Cl_2$ (200 mL) and added dropwise to a mechanically stirred suspension of $AlCl_3$ (154 g, 1.16 mol) in $CH_2Cl_2$ (1.0 L). The stirred suspension was cooled to an internal temperature of −65° C. in a dry ice/acetone bath, and the acid chloride solution was added at such a rate in order to maintain an internal temperature <−60° C. After the addition was complete, ethylene gas was bubbled through the reaction mixture at a rapid rate for 10 min at −65° C. The reaction mixture was allowed to warm to 0° C. over 2 h with stirring, and was then cooled to −10° C. and treated with $H_2O$ (500 mL) initially dropwise, followed by rapid addition. The organic layer was separated, washed with brine (100 mL) and dried over $MgSO_4$. Evaporation under reduced pressure gave a dark oily residue which was distilled in vacuo on a Kugelrohr collecting material boiling between 90-110° C. (1.0 to 0.7 mm Hg). The distillate was redistilled at 100-105° C. (0.3 mm Hg) to give the product as a white solid, (73.6 g, 0.40 mol; 70%): mp 46° C.; IR (KBr) 1705 $cm^{-1}$; $^1H$ NMR ($CDCl_3$) δ 2.55 (t, J=7.5 Hz, 2H), 3.10 (t, J=7.5 Hz, 2H), 3.58 (s, 2H), 6.70 (m, 2H); MS m/z 182 ($M^+$). Anal. Calcd for $C_{10}H_8F_2O$: C, 65.93; H, 4.42. Found: C, 65.54; H, 4.42.

(R)-(+)-2-Hydroxy-5,7-difluoro-1,2,3,4-tetrahydronaphthalene. A solution of (−)-1R,2S—N-methylephedrine (81.3 g, 0.454 mol) in anhydrous $Et_2O$ (1.1 L) was added dropwise (45 min) to 1.0 M lithium aluminum hydride (416 mL, 0.416 mol) in $Et_2O$ at a rate sufficient to maintain a gentle reflux. After the addition was complete, the reaction mixture was heated at reflux for 1 h then allowed to cool to room temperature. A solution of 2-ethylaminopyridine (111 g, 0.98 mole) in anhydrous $Et_2O$ (100 mL) was added (45 min) at such a rate as to maintain a gentle reflux. The reaction mixture was heated at reflux for a further 1 h, during which time a light yellow-green suspension appeared. The mixture was cooled to an internal temperature of −65° C. using a dry ice-acetone bath and a solution of 5,7-difluoro-2-tetralone (23.0 g, 126 mmol) in $Et_2O$ (125 mL) was added dropwise at a rate maintaining the internal temperature below −60° C. After the addition was complete, the mixture was stirred at −65° C. to −68° C. for 3 h and quenched by the addition of MeOH (100 mL) maintaining the internal temperature below −60° C. The reaction was stirred for a further 10 min at −65° C. and allowed to warm to approximately −20° C. A solution of 3N HCl (2 L) was then added at a rate to limit the temperature to <35° C. After stirring at an increased rate to achieve total dissolution, the layers were separated and the ethereal layer was washed with brine (200 mL) and dried ($MgSO_4$). The ethereal solution was evaporated under reduced pressure and the residue dissolved in warm $Et_2O$ (20 mL) followed by the addition of hexane (200 mL). The seeded solution was cooled in an ice bath and maintained at 0° C. for 1 h whereupon the resulting deposited crystals were collected and dried in vacuo to give the alcohol (10.9 g, 47%): mp 85° C.; $[\alpha]^{25}_D$ +38.1° (c=1.83, $CHCl_3$); 93.4% ee by chiral HPLC: $^1H$ NMR ($CDCl_3$) δ 1.70 (br s, 1H), 1.76-1.88 (m, 2H), 1.99-2.06 (m, 2H), 2.63-3.08 (m, 3H), 4.15 (m, 1H), 6.60 (m, 2H). Anal. Calcd for $C_{10}H_{10}F_2O$: C, 65.21; H, 5.47. Found: C, 65.38: H, 5.42. The spectra for the (S)-enantiomer 4b are identical: mp 84-85° C.; $[\alpha]^{25}_D$ −37.8° (c=1.24, $CHCl_3$); 92.4% ee by chiral HPLC. Anal. Calcd for $C_{10}H_{10}F_2O$: C, 65.21; H, 5.47. Found: C, 65.47; H, 5.39.

(R)-(+)-2-M ethane sulfonyloxy-5,7-difluoro-1,2,3,4-tetrahydronaphthalene. A solution of R-(+)-5,7-difluoro-2-tetralol (59.0 g, 320 mmol) and $Et_3N$ (74.2 mL, 53.9 g, 530 mmol) in anhydrous $Et_2O$ (1.78 L) was cooled (−15° C.) using an ice-MeOH bath and treated under argon with stirring with MsCl (37.2 mL, 55.3 g, 480 mmol) over 5-10 min. After 5 h the reaction was complete (as determined by TLC) and water was added to dissolve the solids. A small amount of EtOAc was added to help complete dissolution of the solids. The organic phase was separated and washed sequentially with 1N HCl, aq. $NaHCO_3$, brine and dried over $MgSO_4$. Evaporation of the solvent gave an off-white solid (87.1 g, 332 mmol), used directly in the next step. Trituration of a small sample with i-$Pr_2O$ gave an analytical sample: mp 78.8-80.5° C.; $[\alpha]^{25}_D$ +16.8° (c=1.86, $CHCl_3$); $^1H$ NMR δ 2.13-2.28 (m, 2H), 2.78-2.96 (m, 2H), 3.07 (s, 3H), 3.09 (dd, J=17.1 Hz, 4.7, 1H), 3.20 (dd, J=17.2, 4.7 Hz, 1H), 5.20 (m, 1H), 6.67 (m, 2H). Anal. Calcd for $C_{11}H_{12}F_2O_3S$: C, 50.37; H, 4.61. Found: C, 50.41; H, 4.64. The spectra for the (S)-enantiomer 5b are identical: mp 79.9-80.9° C.; $[\alpha]^{25}_D$ −16.6° (c=2.23, $CHCl_3$). Anal. Calcd for $C_{11}H_{12}F_2O_3S$: C, 50.37; H, 4.61. Found: C, 50.41; H, 4.65.

(S)-(−)-2-Amino-5,7-difluoro-1,2,3,4-tetrahydronaphthalene hydrochloride. Sodium azide (40.0 g, 0.62 mol) was added to DMSO (1 L) with stirring until a clear solution was obtained. The mesylate (138 g, 0.53 mol) was added in one portion and the mixture heated at 50° C. for 16 h under a $N_2$ atmosphere. The reaction mixture was diluted with $H_2O$ (1.8 L) and extracted with pentane (4×250 mL) followed by sequentially washing the combined pentane extracts with $H_2O$ (2×100 mL), brine (100 mL) and drying over $MgSO_4$. Evaporation of the solvent under reduced pressure gave a volatile oil which was rapidly chromatographed on silica using pentane as the eluent to give dihydronaphthalene (8.50 g, 51.2 mmol) as a volatile oil. Further elution with pentane/$CH_2Cl_2$ (9:1) afforded the azide (101 g, 483 mmol) as a colorless oil: IR ($CHCl_3$) 2103 $cm^{-1}$; m/z 171 ($M^+$). The azide 6a was dissolved in EtOAc (1200 mL) and hydrogenated over 10% Pd/C (6 g) in a 2.5 L Parr bottle (60 psi) for 6 h. After each hour, the bottle was evacuated and recharged with hydrogen to remove evolved $N_2$. The resulting mixture was filtered through Celite, stirred with ethereal HCl (1N, 500 mL), and the fine precipitate filtered off and washed with EtOAc, and then anhydrous ether. (The filtration took about 4 h). The moist solid was transferred to a round-bottom flask, and the remaining solvent removed in vacuo to give a white solid (90.4 g, 412 mmol; 77.9%): mp>280° C.; $[\alpha]^{25}_D$ −60.2° (c=2.68, MeOH); $^1H$ NMR ($d_6$-DMSO) δ 1.79 (m, 1H), 2.33 (m, 1H), 2.63 (m, 1H), 2.83-2.92 (m. 2H), 3.14 (dd, J=16.7, 5.0 Hz, 1H), 3.46 (m, 1H), 6.93 (d, J=9.4 Hz, 1H), 7.00 (dt, J=9.4, 2.5 Hz, 1H). Anal. Calcd for $C_{10}H_{12}ClF_2N$: C, 54.68; H, 5.51; N, 6.37. Found: C, 54.31; H, 5.52; N, 6.44. The spectra for the (R)-enantiomer 8b are identical: mp>280° C.; $[\alpha]^{25}_D$ +58.5° (c=1.63, MeOH). Anal. Calcd for $C_{10}H_{12}ClF_2N$: C, 54.68; H, 5.51; N, 6.37. Found: C, 54.64; H, 5.51; N, 6.40.

(S)-(−)-(5,7-Difluoro-1,2,3,4-tetrahydronaphth-2-yl)(cyanomethyl)amine. The amine hydrochloride 8a (50.27 g, 229 mmol) was treated with a solution of NaOH (10.0 g. 250 mmol) in water (150 mL), followed by a few additional pellets of NaOH sufficient to obtain a solution. Further water (300 mL) was added and the mixture placed in a 50° C. bath and treated with formaldehyde sodium bisulfite complex (30.8 g, 230 mmol). After the mixture had been stirred for 30 min, KCN (15.0 g, 230 mmol) was added. The reaction mixture was stirred for a further 1 h at 80° C., cooled to room temperature, and extracted with EtOAc to give an oil (51.3 g) which solidified. TLC (5% MeOH—$CH_2Cl_2$) showed ca. 10-15% of starting amine remained. Chromatography on silica gave the nitrile product (39.4 g) and starting free amine (7.12 g), which quickly forms the carbonate in air. Recycling this amine gave an additional 5.35 g of product. Combined yield (44.8 g, 202 mmol; 87.5%): mp 73.1-76.5° C.; $[\alpha]^{25}_D$-58.0° (c=1.63, $CHCl_3$); $^1H$ NMR ($CDCl_3$) δ 1.50 (br s, 1H), 1.70 (m, 1H), 2.05 (m, 1H), 2.55-3.04 (m, 4H), 3.22 (m, 1H), 3.70 (s, 2H), 6.62 (m, 2H); MS m/z 222 ($M^+$). Anal. Calcd for $C_{12}H_{12}F_2N_2$: C, 64.85; H, 5.44; N, 12.60. Found: C, 65.07; H, 5.47; N, 12.44. The spectra for the (R)-enantiomer 9b are identical: mp 64.4-73.6° C.; $[\alpha]^{25}_D$ +52.3° (c=2.12, $CHCl_3$). Anal. Calcd for $C_{12}H_{12}F_2N_2$: C, 64.85; H, 5.44; N, 12.60. Found: C, 65.14; H, 5.54; N, 12.53.

(S)-(+)-1-(5,7-Difluoro-1,2,3,4-tetrahydronaphth-2-yl)-5-cyano-2,3-dihydro-2-thioxo-1H-imidazole. The nitrile (44.7 g, 201 mmol) in butyl formate (240 mL) was heated at reflux (120° C. bath) under $N_2$ for 19 h, and the solvent then removed under reduced pressure. Toluene was added and evaporated to remove last traces of solvent, and the residue was dried under high vacuum to give an oil (53.2 g). The resulting formamide and ethyl formate (48.7 mL, 44.7 g, 604 mmol) in anhydrous THF (935 mL) were cooled in ice/MeOH (-15° C.) and stirred while t-BuOK (1M in THF, 302 mL, 302 mmol) was added over 20 min. After the reaction had been stirred for 18 h, the solvent was evaporated, the residue dissolved in 1N HCl (990 mL) and ethanol (497 mL), and treated with KSCN (78.1 g, 804 mmol). The mixture was stirred for 135 min at 85° C. and then placed in an ice bath to give a precipitate. The filtered solid was loaded as a slurry in 10% MeOH/$CH_2Cl_2$ on to a silica (1 kg) column packed in hexane. Elution with 10% acetone/$CH_2Cl_2$ gave the product (18.05 g, 62.1 mmol; 30.8%): m.p. 240.7-249.2° C.; $[\forall]^{25}_D$ -69.1° (c=1.18, DMSO); $^1H$ NMR ($d_6$-DMSO) δ 2.18 (br m, 1H), 2.47 (m, 1H), 2.75 (m, 1H), 3.03-3.35 (m, 3H), 5.19 (m, 1H), 6.94 (d, J=9.3 Hz, 1H), 7.03 (dt, J=9.3, 2.4 Hz, 1H), 8.29 (s, 1H), 13.3 (br s, 1H); MS m/z 291 ($M^+$). Anal. Calcd for $C_{14}H_{11}F_2N_3S$: C, 57.72; H, 3.80; N, 14.42. Found: C, 57.82; H, 3.92; N, 14.37. (Further elution of the column with 1:1 MeOH/$CH_2Cl_2$ gave the primary amide 11a: mp 261.9-262.7° C.; $[\forall]^{25}_D$ -90.5° (c=0.398); IR (KBr) 1593, 1630 $cm^{-1}$; $^1H$ NMR ($d_6$-DMSO) δ 2.14 (m, 1H), 2.15-2.28 (m, 1H), 2.74-3.05 (m, 4H), 5.64 (m, 1H), 6.90 (d, J=9.2 Hz, 1H), 7.05 (dt. J=9.5, 2.4 Hz, 1H), 8.73 (s, 1H), 9.70 (br s, 1H), 13.7 (br s, 1H); MS m/z 309 ($M^+$). Anal. Calcd for $C_{14}H_{13}F_2N_3OS.0.25H_2O$: C, 53.57; H, 4.33; N, 13.39. Found: C, 53.32; H, 3.96: N, 13.24. The spectra for the (R)-enantiomer are identical: mp 243.1-244.7° C.; $[\forall]^{25}_D$+74.9° (c=2.14, DMSO). Anal. Calcd for $C_{14}H_{11}F_2N_3S$: C, 57.72; H, 3.80; N, 14.42. Found: C, 57.85; H, 3.85; N, 14.45.

(S)-1-(5,7-Difluoro-1,2,3,4-tetrahydronaphth-2-yl)-5-aminomethyl-2,3-dihydro-2-thioxo-1H-imidazole. The above nitrile (5.00 g, 17.2 mmol) in THF (75 mL) was stirred under argon in an ice bath until a homogeneous solution was obtained. A solution of LAH in THF (1 M, 34.3 mL, 34.3 mmol) was added dropwise over 10 min, then the solution was stirred for 30 min at 0° C. and allowed to come to room temperature for 1.5 h. The reaction was again cooled to 0° C. and treated with a saturated solution of sodium potassium tartrate until the mixture became freely stirrable. Further tartrate solution (30 mL) was added, followed by 10% MeOH/$CH_2Cl_2$ (200 mL) and the mixture stirred for 15 min and treated with water (100-150 mL). The organic layer was separated and the aqueous phase extracted with 10% MeOH/$CH_2Cl_2$ (2×125 mL). The combined extracts were washed, dried ($MgSO_4$), and evaporated. Chromatography of the residue (5.2 g) on silica eluting with 5% MeOH/$CH_2Cl_2$ gave the free amine (2.92 g, 9.89 mmol; 58%): mp 170° C.; $[\forall]^{25}_D$ -11.0° (c=1.59, DMSO). Anal. Calcd for $C_{14}H_{15}F_2N_3S.0.25H_2O$: C, 56.07; H, 5.21; N, 14.01. Found: C, 56.11; H, 5.10; N, 14.14.

(S)-1-(5,7-Difluoro-1,2,3,4-tetrahydronaphth-2-yl)-5-aminomethyl-2,3-dihydro-2-thioxo-1H-imidazole hydrochloride (nepicastat). The hydrochloride salt was prepared by the addition of ethereal HCl (1M, 20 mL, 20 mmol) to the free amine 2a (3.12 g, 10.6 mmol) which had been dissolved in MeOH (250 mL) by warming. The solvent was partially removed under reduced pressure and displaced by co-evaporation with EtOAc several times without evaporating to dryness. The resulting precipitate was treated with EtOAc (150 mL) and ether (150 mL), filtered off, washed with ether, and dried under nitrogen and then under high vacuum at 78° C. for 20 h to give the hydrochloride salt (3.87 g): mp 245° C. (dec); $[a]^{25}_D$+9.65° (c=1.70, DMSO); (93% ee by chiral HPLC); $^1H$ NMR (T=320° K, DMSO) δ 2.07 (m, 1H), 2.68-3.08 (m, 4H), 4.09 (m, 3H), 4.77 (m, 1H), 6.84 (m, 2H), 7.05 (s, 1H), 8.57 (br s, 3H), 12.4 (br s, 1H). Anal. Calcd for $C_{14}H_{16}ClF_2N_3S.0.5H_2O$: C, 49.33; H, 5.03; N, 12.33. Found: C, 49.44; H, 4.96; N, 12.18. The spectra for the (R)-enantiomer (R)-1-(5,7-Difluoro-1,2,3,4-tetrahydronaphth-2-yl)-5-aminomethyl-2,3-dihydro- are identical; mp 261-263° C.; $[\alpha]^{25}_D$ -10.8° (c=1.43, DMSO), 91.6% ee by chiral HPLC. Anal. Calcd for $C_{14}H_{16}ClF_2N_3S.0.35H_2O$: C, 49.73; H, 4.98; N, 12.42. Found: C, 49.80; H, 4.93; N, 12.39.

Nepicastat was demonstrated to be a competitive inhibitor of bovine ($IC_{50}$=8.5±0.8 nM) and human ($IC_{50}$=9.0±0.8 nM) DBH. The R-enantiomer (R)-1-(5,7-Difluoro-1,2,3,4-tetrahydronaphth-2-yl)-5-aminomethyl-2,3-dihydro- ($IC_{50}$s=25.1±0.6 nM; 18.3±0.6 nM) and SKF 102698 ($IC_{50}$s=67.0±4.2 nM; 85.0±3.7 nM) are less potent inhibitors of the bovine and human enzymes, respectively. DBH activity was assayed by measuring the conversion of tyramine to octopamine. Bovine DBH from adrenal glands was obtained from Sigma Chemical Co (St Louis, Mo.). Human secretory DBH was purified from the culture medium of the neuroblastoma cell line SK-N-SH. The assay was performed at pH 5.2 and 32° C. in 0.125 M NaOAc, 10 mM fumarate, 0.5-2 μM $CUSO_4$, 0.1 mg/mL catalase, 0.1 mM tyramine and 4 mM ascorbate. In a typical assay, 0.5-1 milliunits of enzyme were added to the reaction mixture and then a substrate mixture containing catalase, tyramine and ascorbate was added to initiate the reaction (final volume of 200 μL). Samples were incubated with or without the appropriate concentration of the inhibitor at 37° C. for 30-40 min. The reaction was quenched by the stop solution containing 25 mM EDTA and 240 μM 3-hydroxytyramine (internal standard). The samples were analyzed for octopamine by reverse phase HPLC using UV detection at 280 nM. The remaining percent activity was calculated based on controls (without inhibitor), corrected using internal standards and fitted to a non-linear 4-parameter concentration-response curve to obtain $IC_{50}$ values.

The activity of nepicastat at eleven different enzymes was determined using established assays. The affinity of nepicastat for thirteen selected receptors was determined by radioligand binding assays using standard filtration techniques and membrane preparations. Binding data were analyzed by iterative curve fitting to a four parameter logistic equation. $K_i$ values were calculated using the Cheng-Prusoff equation. FIG. 3 shows a table describing the interaction of nepicastat at DBH and a range of selected enzymes and receptors. Nepicastat showed weak affinity for a range of other enzymes and neurotransmitter receptors. These data suggest that nepicastat is a potent and highly selective inhibitor of DBH in vitro. Moreover, the S-enantiomer nepicastat is approximately 2-3 fold more potent than the R-enantiomer suggesting stereoselectivity.

Oral administration of nepicastat to spontaneously hypertensive rats (SHRs) and normal dogs produced potent and dose-dependent increases in tissue dopamine (DA)/norepinephrine (NE) ratios in peripheral arteries (renal or mesenteric), left ventricle and cerebral cortex. Chronic oral administration of nepicastat to normal dogs also produced sustained increases in the plasma DA/NE ratio. In conscious SHRs, acute oral administration of nepicastat produced dose-dependent and long-lasting (>4 h) antihypertensive effects and also attenuation of the pressor responses to pre-ganglionic sympathetic nerve stimulation. Serum $T_3$ and $T_4$ levels were unaffected by a dose (6.2 mg/kg, po, b.i.d. for 10 days) which elevated the dopamine/norepinephrine ratio in the mesenteric artery. On the basis of its ability to potently modulate the sympathetic drive to cardiovascular tissues, nepicastat has been clinical evaluated for the treatment of congestive heart failure.

Congestive heart failure (CHF) is a leading cause of mortality in the United States. CHF is characterized by marked activation of the sympathetic nervous system (SNS) and renin-angiotensin system (RAS). The simultaneous activation of these two neurohormonal systems has been increasingly implicated in the perpetuation and progression of CHF. Therapeutic interventions which block the effects of these neurohormonal systems are likely to favorably alter the natural history of CHF. Indeed, angiotensin-converting enzyme (ACE) inhibitors, which block formation of angiotensin II, have been shown to reduce morbidity and mortality in CHF patients. ACE inhibitors, however, have a limited indirect ability to attenuate the SNS. Inhibition of the SNS with β-adrenoceptor antagonists is a promising approach that is currently under clinical evaluation. An alternative strategy to directly modulate the SNS is inhibition of norepinephrine (NE) biosynthesis via inhibition of dopamine β-hydroxylase (DBH), the enzyme responsible for conversion of NE to dopamine (DA). Inhibition of DBH would be expected to reduce tissue levels of NE and elevate tissue levels of DA thereby increasing the tissue DA/NE ratio. This approach has potential advantages over β-adrenoceptor antagonists, such as reduced stimulation of α-adrenoceptors and elevated DA levels that can produce renal vasodilation, natriuresis and diminished aldosterone release. Previous DBH inhibitors, such as fusaric acid and SKF-102698, have drawbacks such as low potency and specificity, that have precluded their clinical development in heart failure.

Nepicastat was used in in vivo biochemical studies to study the effects in spontaneously hypertensive rats (SHRs) and normal beagle dogs. On the day of the study, the animals were weighed and randomly assigned to receive either placebo (vehicle) or the appropriate dose of nepicastat. Each rat was dosed orally three times, 12 h apart, beginning in the morning. At 6 h after the third dose, the rats were anesthetized with halothane, decapitated, and the tissues (cerebral cortex, mesenteric artery and left ventricle) were rapidly harvested, weighed, placed in iced 0.4 M perchloric acid, frozen in liquid nitrogen and stored at −70° C. until analysis. Tissue NE and DA concentrations were assayed by HPLC using electrochemical detection. Male beagle dogs (10-16 kg, Marshall Farms USA Inc, North Rose, N.Y.) were used in the study. On the day of the study, dogs were randomly assigned to receive either placebo (empty capsule) or the appropriate dose of nepicastat. Each dog was dosed twice a day for 4.5 days. 6 h after the first dose on day 5, the dogs were euthanized with pentobarbital and the tissues (cerebral cortex. renal artery, left ventricle) harvested, weighed, placed in iced 0.4 M perchloric acid, frozen in liquid nitrogen and stored at −70° C. until analysis. Tissue NE and DA concentrations were assayed by HPLC using electrochemical detection.

Oral administration of nepicastat produced dose-dependent increases in DA/NE ratios in the artery (mesenteric or renal), left ventricle and cerebral cortex in SHRs and dogs. At the highest dose tested (100 mg/kg in SHRs and 5 mg/kg in dogs) the maximal increases in DA/NE ratio were 14, 11 and 3.2 fold (in SHRs) and 95, 151 and 80 fold (in dogs) in the artery, left ventricle and cerebral cortex, respectively. When tested at 30 mg/kg in SHRs, SKF-102698 (1) increased the DA/NE ratio by 5.5-fold, 3.5-fold and 2.7-fold, whereas nepicastat, at the same dose, increased the ratio by 8.3, 7.5 and 1.5 fold in the mesenteric artery, left ventricle and cerebral cortex, respectively. Compound B at 30 mg/kg in SHRs, produced only 2.6, 3.5 and 1.1 fold increases in the DA/NE ratio in the mesenteric artery, left ventricle and cerebral cortex, respectively. These data suggest that nepicastat produces the expected biochemical effects in both SHRs and dogs but is more potent in the latter species. Furthermore, nepicastat is more potent than its Compound B and SKF-102698 (1) in SHRs.

The chronic effects of nepicastat (14.5 day treatment) on the plasma DA/NE ratio were investigated in normal dogs. Animals were randomized to receive, orally, either placebo (empty capsule) or nepicastat (2 mg/kg, b.i.d) for 14.5 days. Daily blood samples were drawn, 6 h after the first dose, for the measurement of plasma concentrations of DA and NE. The samples were collected in tubes containing heparin and glutathione, centrifuged at −4° C. and stored at −70° C. until analysis.

Oral administration of nepicastat (2 mg/kg; b.i.d) produced a significant increase in the DA/NE ratio that attained its peak effect at approximately 6-7 days, then plateaued to a new steady-state between 7-14 days.

The in vivo hemodynamic activity of nepicastat was further assessed in conscious, restrained SHRs, a model having high sympathetic drive to cardiovascular tissues. Hemodynamic study in SHRs. Male SHRs (15-16 week old) were used in the study. The animals were lightly anesthetized with ether and the left femoral artery and vein were catheterized for measurement of blood pressure and drug administration, respectively. The animals were placed in restrainers and allowed to recover for 30-40 min. After obtaining baseline measurements, the animals were treated, orally, with either vehicle or the appropriate dose of nepicastat and hemodynamic parameters were continuously recorded for 4 h. The animals were then anesthetized with pentobarbital, placed on a heating pad (37° C.) and ventilated with a Harvard rodent ventilator. After administration of atropine (1 mg/kg, iv) and tubocurarine (1 mg/kg, iv), the animals were pithed through the orbit of the eye with a stainless steel rod. The pithing rod was stimulated electrically with 1 ms pulses of 80V at different frequencies (0.15, 0.45, 1.5, 5, 15 Hz) to obtain frequency-pressor response curves.

Oral dosing of nepicastat resulted in a dose-dependent antihypertensive effect. The animals were placed in restrainers and allowed to recover for 30-40 minutes. After obtaining baseline measurements, the animals were treated, orally, with either vehicle or the appropriate dose of nepicastat and hemodynamic parameters were continuously recorded for 4 h. Nepicastat produced significant (p<0.05) lowering of mean arterial pressure at all doses and time points, except at 0.3 mg/kg (180, 210 and 240 min) and 1 mg/kg (30, 210 and 240 min).

A maximal decrease in mean blood pressure of 53±4 mmHg (33% reduction relative to vehicle control) was observed at the 10 mg/kg dose. The response was slow in onset, reaching its plateau in 3-4 h. The precise reason for the loss of anti-hypertensive efficacy at the highest dose (30 mg/kg) is unclear at present. Heart rate was not significantly affected except for a slight yet significant decrease at 10 and 30 mg/kg, (9.8 and 10.5%, respectively). Following this study, the rats were pithed and the effects of nepicastat on the pressor response to pre-ganglionic nerve stimulation (PNS) of the spinal cord were evaluated 5 h after dosing. The frequency-pressor response curve was shifted significantly (p<0.05) to the right in a dose-dependent manner (maximum shift of ~5 fold in the frequency-response curve). The heart rate response to PNS was not significantly affected. These data suggest that nepicastat inhibits the sympathetic drive to the vasculature and is the probable mechanism for its anti-hypertensive effect in SHRs.

Since the heterocyclic portion of nepicastat is structurally similar to methimazole, a known potent suppressor of mammalian thyroid function, the effects of nepicastat on thyroid function were evaluated at doses of 2.0 and 6.2 mg/kg, po, b.i.d in iodine-deficient Sprague-Dawley rats (n=9-12) for 10 days. Methimazole (1 mg/kg, po, b.i.d.), used as a positive control, caused a significant reduction in serum levels of $T_3$ (day 3, 31%, p<0.05; days 7 and 9, 42% and 44%, p<0.01) and $T_4$ (days 3 and 7, 46% and 58%, p<0.01) 4 h post-dose, whereas nepicastat showed no significant effects throughout the study (days 3, 7 and 9). Both doses of nepicastat significantly raised the DA/NE ratio in the mesenteric artery (p<0.01 relative to vehicle controls) but not in the cortex 4 h after the final dose on day 10.

The findings of this study suggest that nepicastat is a potent, selective and orally active inhibitor of DBH. The compound is also devoid of significant behavioral effects in animal models and these findings will be the subject of a future publication. As compound nepicastat effectively modulates the sympathetic drive to cardiovascular tissues, it has been tested for the treatment of CHF.

Example 7

Concentrations of dopamine and norepinephrine were determined in 942 samples of plasma collected from congestive heart failure (CHF) patients. The objectives of the study were:

1. to evaluate the effects of various doses of nepicastat on transmyocardial (arterial-coronary sinus) and coronary sinus catecholamine levels after four weeks, and to evaluate the safety and tolerability of nepicastat over 12 weeks.

2. to evaluate the effects of nepicastat on changes from baseline in:
    a) Plasma (venous) catecholamine levels after four weeks and 12 weeks
    b) Quality of life (QoL), CHF symptoms, Global Assessments, and NYHA class after four weeks and 12 weeks
    c) Hemodynamic parameters, including cardiac output, systemic vascular resistance, $MVO_2$, pulmonary artery pressures, and pulmonary artery wedge pressure after four weeks
    d) Hospitalizations and changes in medication dosages for the treatment of CHF over 12 weeks
    e) Blood pressure and heart rate at four and 12 weeks
    f) Six-Minute Walk Test after four weeks and 12 weeks
    g) Left ventricular ejection fraction, left ventricular end systolic, and left ventricular end diastolic volumes at 12 weeks.

Samples of blood were collected from patients from a peripheral vein, whilst they were supine, at 2 hours post-dose during weeks 4 and 12. Further samples from supine patients were collected on day 0 (i.e. the day prior to the start of dosing) at a time corresponding to 2 hours post-dose. In addition, a group of patients underwent right heart and coronary sinus catheterization during week 4 at 2 hours post-dose and on day 0 (i.e. the day prior to the start of dosing) at a time corresponding to 2 hours post-dose. Triplicate samples of blood were collected from the arterial vein and coronary sinus of these patients.

Concentrations of the free base of dopamine and norepinephrine were determined by a radioenzymatic method. The method involves the incubation of the plasma samples with catechol-O-methyl transferase and tritiated S-adenosyl methionine. On completion of the incubation, the O-methylated catecholamines are extracted from the plasma by liquid/liquid extraction and then separated by thin layer chromatography. The relevant bands for each catecholamine are marked and then scraped into scintillation vials for counting. The quantitation limit of the method is 1 pg of dopamine or norepinephrine per mL of plasma. The linear range is 1 to 333000 pg of dopamine or norepinephrine per mL of plasma using aliquots of 0.045 mL to 1 mL.

A pooled human plasma sample was used as the Quality Control sample (QC) and was analyzed in singlicate each day during routine use of the method to monitor the performance of the method.

Example 8

Preclinical in vitro and in vivo pharmacology studies were conducted with nepicastat. The in vitro studies assessed the ability of the compound to inhibit DBH activity, and its binding affinity at selected receptors. The in vivo studies are subdivided into four categories: 1) biochemical effects (i.e. the ability to decrease tissue norepinephrine levels and increase dopamine levels), 2) effects on thyroid function, 3) cardiovascular effects, and 4) behavioral effects.

Nepicastat was a potent inhibitor of both bovine and human DBH. The $IC_{50}$ for nepicastat on human DBH was 9 nM (CL 6960), significantly lower than that for the DBH inhibitor SKF-102698 (85 nM). The S enantiomer nepicastat was more potent than the R enantiomer (18 nM), denoted as Compound B.

The binding affinity for nepicastat was screened at selected receptors. Nepicastat showed a binding affinity of less than 5.0 for M1, D1 and D2, and $5HT_{1A,\ 2A}$ and $2_C$. The N-acetyl metabolite of nepicastat in rats and monkeys, showed a similar lack of binding affinity for these receptors. Thus nepicastat and its primary metabolite were not potent inhibitors for the receptors listed above.

The aortic contractile response in vitro to phenylephrine is impaired in spontaneously hypertensive rats (SHRs) relative to normotensive Wistar-Kyoto rats. Daily treatment with nepicastat (10 mg/kg, p.o.) in SHRs for 21 days restored phenylephrine responsiveness to values comparable to the Wistar-Kyoto rats.

Overall, nepicastat was an effective inhibitor of DBH in rats and dogs. Oral or intravenous administration resulted in a significant (p<0.05) decrease in tissue norepinephrine, an increase in dopamine, and an increase in the dopamine/ norepinephrine levels in the heart, mesenteric or renal artery, and the cerebral cortex in both species.

In studies with male spontaneously hypertensive rats (SHRs), nepicastat significantly decreased norepinephrine and increased dopamine and the dopamine/norepinephrine ratio in the mesenteric artery from 0.5 to 4 hours following oral or i.v. administration at 6.2 mg/kg. Significant changes in these parameters were also observed in the left ventricle of male Sprague-Dawley rats 6 hours after the second of two i.v. injections (15 mg/kg) given 12 hours apart. The 24 hour time course of tissue catecholamines was studied in male SHRs following oral administration of either 10 or 30 mg/kg, respectively. The increase in the dopamine/norepinephrine ratio was significant at 1 hour, and was long lasting (12 hours at 10 mg/kg, mesenteric artery, and 24 hours at 30 mg/kg, left ventricle). Significant changes in mesenteric artery dopamine and norepinephrine levels were observed following 10 days of dosing to male Sprague-Dawley rats at 2.0 and 6.2 mg/kg p.o. b.i.d., with no significant effects observed in the cerebral cortex. SHRs dosed at 1 or 10 mg/kg/d p.o. for either 7 or 25 days had significant increases in dopamine and the dopamine/norepinephrine ratio in the mesenteric artery and cerebral cortex. Taken together, nepicastat resulted in a significant decrease in norepinephrine and an elevation in dopamine and the dopamine/norepinephrine ratio in the mesenteric artery in rats with either acute or chronic (up to 25 days) dosing.

The effects of nepicastat in male SHRs and Sprague-Dawley rats were found to be dose responsive when assessed 6 hours following a single oral dose at 0.3, 1, 3, 10, 30, and 100 mg/kg. In SHRs there were significant changes in the dopamine/norepinephrine ratio in the mesenteric artery at doses of 0.3 mg/kg, in the left ventricle at 3.0 mg/kg, and in the cerebral cortex at 10 mg/kg. In Sprague-Dawley rats there were significant increases in the dopamine/norepinephrine ratio in the mesenteric artery at 3.0 mg/kg, in the left ventricle at 1.0 mg/kg, and in the cerebral cortex only at 100 mg/kg. In a second dose-response study in SHRs, three doses were administered 12 hours apart at either 3.0, 10, 30, or 100 mg/kg, and tissue was harvested six hours after the third dose. Nepicastat caused a significant dose dependent decrease in norepinephrine (10 mg/kg) and increase in dopamine (3.0 mg/kg) and the dopamine/norepinephrine ratio (3.0 mg/kg) in the left ventricle and mesenteric artery. The effects of nepicastat on dopamine and norepinephrine concentrations, and the dopamine/norepinephrine ratio in the cerebral cortex were significant only at 30 and 100 mg/kg. Similar significant dose-response effects in the left ventricle were seen in female Wistar rats dosed with nepicastat for 7 days via the drinking water (0.3, 0.6, and 1.0 mg/ml). In conclusion, nepicastat was less potent in inhibiting DBH in the cerebral cortex of rats (60-100 mg/kg/d) than in the left ventricle and mesenteric artery (1-6 mg/kg/d).

Nepicastat (the S enantiomer) was significantly more potent then the R enantiomer in the left ventricle and mesenteric artery in SHRs after three doses given 12 hours apart (30 mg/kg p.o.). nepicastat was significantly more potent than the DBH inhibitor SKF-102698 in decreasing norepinephrine and increasing dopamine and the dopamine/norepinephrine ratio in the left ventricle and mesenteric artery in SHRs after a single dose, or three doses at 30 mg/kg. The potency relationships in the left ventricle and mesenteric artery resulting from these in vivo studies strongly parallel those obtained from in vitro studies using purified DBH (see above). However, nepicastat had significantly less effects than SKF-102698 in decreasing norepinephrine levels and increasing dopamine levels in the cerebral cortex. Norepinephrine has been shown to stimulate the release of renin and increase plasma renin activity. It was therefore of interest to assess whether decreasing norepinephrine levels with nepicastat would result in a decrease in plasma renin activity. However, nepicastat (30 and 100 mg/kg/d p.o. for 5 days) did not alter plasma renin activity in male SHRs. Thus, nepicastat, when given at doses that lower tissue norepinephrine levels, does not alter plasma renin activity in SHRs.

Nepicastat caused a significant decrease in norepinephrine levels and an increase in the dopamine/norepinephrine ratio, but did not alter dopamine levels, in the mesenteric artery from male beagle dogs 5 hours after administration of 30 mg/kg intraduodenally. When nepicastat was given to male beagle dogs for 4.5 days (5, 15, and 30 mg/kg b.i.d., or 10, 30, and 60 mg/kg/d) there was a significant decrease in norepinephrine, and an increase in dopamine and the dopamine/norepinephrine ratio in the renal artery, renal cortex, and renal medulla, with a plateau in response beginning at 10 mg/kg/d and extending through 60 mg/kg/d. Similar results were observed in the left ventricle, except that there was no significant increase in dopamine. In the cerebral cortex, norepinephrine significantly decreased at 30 and 60 mg/kg/d, and dopamine and the dopamine/norepinephrine ratio significantly increased at all doses. In conclusion, nepicastat was a potent, orally active inhibitor of DBH in dogs at doses of at least 10 mg/kg/d.

Nepicastat has structural similarities to methimazole, a potent inhibitor of thyroid peroxidase in vivo. nepicastat at doses of 4 or 12.4 mg/kg/d, p.o. had no effect on serum levels of triiodothyramine or thyroxine in male Sprague-Dawley rats fed a low iodine diet and dosed for 10 days, while methimazole (2 mg/kg/d) significantly reduced serum levels of triiodothyramine or thyroxine. Thus, nepicastat, unlike methimazole, did not affect serum levels of triiodothyramine or thyroxine.

Nepicastat induced a significant antihypertensive effect for up to 4 hours in conscious, restrained SHRs (1.0-30 mg/kg, p.o.), and significantly reduced heart rate (10 and 30 mg/kg). The antihypertensive effects of nepicastat in conscious, restrained SHRs (10 mg/kg, p.o.) were not attenuated by pretreatment with the dopamine receptor (DA-1) antagonist SCH-23390. nepicastat (10 mg/kg) also reduced blood pressure 4 hours after dosing in conscious, restrained normotensive Wistar-Kyoto rats; however, the decrease in pressure was less (−13 mmHg) than with SHRs (−46 mmHg). To summarize together, nepicastat causes a decrease in blood pressure in both SHRs and normotensive rats, though the antihypertensive effect is more pronounced in SHRs. The antihypertensive effects in SHRs do not appear to be mediated via DA-1 receptors.

Nepicastat also significantly attenuated the hypertensive and tachycardic responses to preganglionic nerve stimulation in pithed SHRs 5 hours after dosing (3 mg/kg p.o.). Thus, nepicastat reduces the rise in blood pressure in response to sympathetic nerve stimulation.

Acute intravenous treatment of anesthetized SHRs with nepicastat (3.0 mg/kg, i.v.) decreased mean arterial pressure over a 3 hour period, but did not lower renal blood flow or alter urine production or urinary excretion of sodium or potassium. The calculated renal vascular resistance was decreased following dosing. An attempt was made using the DA-1 antagonist SCH-23390 to assess if the renal vasodilator effects of nepicastat were mediated by DA-1 receptors. However this compound reduced blood pressure when given alone, thus making the results uninterpretable. Overall, nepicastat did not impair renal function in anesthetized SHRs, and did not decrease renal blood flow despite causing a decrease in arterial blood pressure.

Daily treatment with nepicastat (1 and 10 mg/kg, p.o.) in SHRs for 21 days did not alter heart rate, or systolic blood pressure as measured by the tail cuff method. However, nepicastat (10 mg/kg, p.o.) induced a significant antihypertensive effect when the rats were restrained and their blood pressure measured directly via an arterial cannulae.

Nepicastat significantly lowered blood pressure in SHRs instrumented with radio-telemetry blood pressure transducers at doses of 30 and 100 mg/kg/d for 30 days, but produced no significant effects were observed at 3 and 10 mg/kg/d. The effect at 30 and 100 mg/kg/d persisted over a 24-hour period after a single dose, and there was no loss of effect over 30 days. Heart rate was not increased, and motor activity was unaffected. A combination of a dose of the angiotensin converting enzyme inhibitor enalapril (1 mg/kg, p.o.) that failed to lower blood pressure with nepicastat (30 mg/kg) caused a potentiation of the antihypertensive effects of nepicastat over 30 days of dosing, and resulted in a significant reduction in left ventricular mass. A reduction in left ventricular mass did not occur with enalapril alone. Thus, 30 days of treatment of SHRs with nepicastat at 30 and 100 mg/kg/d resulted in a decrease in blood pressure and, when combined with enalapril, additional blood pressure decreases along with a reduction in left ventricular mass.

The blood pressure lowering effect of nepicastat in normotensive Wistar rats instrumented with radio-telemetry blood pressure transducers was less than the effect observer in SHRs at doses of 30 and 100 mg/kg/d for 7 days. At 30 mg/kg/d the peak decrease in blood pressure was −10 mmHg, compared to −20 in SHRs. At 100 mg/kg/d the peak decrease in blood pressure was −17 mmHg, compared to −42 in SHRs. Thus, nepicastat had a greater blood pressure lowering effect in SHRs than in normotensive rats.

Studies in normal anesthetized dogs showed no cardiovascular effects of nepicastat following acute intravenous dosing (1-10 mg/kg i.v.) with no changes in arterial blood pressure, left ventricular pressures (including peak dp/dt), heart rate, cardiac output or renal blood flow for up to five hours after dosing. A similar lack of effect was observed in chronically instrumented, conscious dogs studied for 12 hours after a single dose (3-30 mg/kg i.v.).

Nepicastat (30 mg/kg intraduodenally) did not significantly inhibit either the decrease in renal blood flow in response to direct renal nerve stimulation, or the increase in arterial blood pressure in response to carotid artery occlusion up to 5 hours after dosing in anesthetized male beagle dogs. However, nepicastat caused a significant decrease in norepinephrine levels and an increase in the dopamine/norepinephrine ratio, but not dopamine levels, in the mesenteric artery 5 hours after dosing. Thus, although tissue norepinephrine levels were significantly reduced, there was no significant inhibition of sympathetically-evoked functional responses.

When nepicastat was given to male beagle dogs for 4.5 days at 10 mg/kg/d there was no statistically significant decrease in the degree of blood pressure and heart rate increases in response to carotid artery occlusion in anesthetized animals. Nepicastat treatment significantly reduced the increase in heart rate in response to an i.v. tyramine challenge, but produced only slight and non-significant inhibition of blood pressure increases. Thus, chronic dosing with nepicastat at a dose that has been shown to result in a maximal decrease in tissue norepinephrine levels, does not have a major inhibitory effect on sympathetically-evoked functional responses.

Nepicastat caused no significant effects on gross motor behavior in mice following acute dosing at 1.0-30 mg/kg, p.o., and it did not effect locomotor activity in mice (10-100 mg/kg i.p.). Acute administration to rats did not effect locomotor activity or acoustic startle reactivity (3-100 mg/kg i.p.).

No behavioral effects were observed in rats following 10 days of dosing at 10, 30, and 100 mg/kg/d, p.o. Rectal temperature was also unaffected. Motor activity and auditory startle reflex were significantly reduced by treatment with the DBH inhibitor SKF-102698 (100 mg/kg/d, p.o.), and by the centrally acting a-adrenergic agonist clonidine (20 mg/kg, b.i.d., p.o.). Motor activity was also unaffected over 30 days of dosing in SHRs (3-100 mg/kg/d, p.o.). Thus, nepicastat did not cause detectable changes in central nervous system mediated behavioral effects in rats.

Nepicastat is a potent competitive inhibitor of human DBH in vitro, and in rats and dogs in vivo. In rats, oral treatment with nepicastat resulted in significant evidence for DBH inhibition in the heart and mesenteric artery at a dose 6 mg/kg/d. In contrast to another DBH inhibitor, SKF-102698, nepicastat showed some selectivity to the left ventricle and mesenteric artery relative to the cerebral cortex. No behavioral effects were observed with nepicastat in rats. In dogs, a plateau effect for DBH inhibition occurred at 10 mg/kg/d in the heart, renal artery and kidney. Nepicastat significantly reduced the hypertensive response to sympathetic nerve stimulation in rats (3 mg/kg p.o.), and it significantly lowered blood pressure throughout the day when dosed once daily (30 mg/kg/d p.o.) for 30 days in SHRs. In conclusion, nepicastat is a potent DBH inhibitor that modulates the action of the sympathetic nervous system.

Example 9

The studies described here were designed to evaluate the pharmacokinetics of higher oral doses of nepicastat, to compare the pharmacokinetics in male and female rats, and to determine penetration of nepicastat into the CNS by quantitating levels of nepicastat in brain.

Male rats (Crl: CD BR Vaf+) weighing 180-220 g were fasted overnight before dosing and until 4 hr after dosing. Doses were formulated in water containing 2% 1-hydroxypropyl methylcellulose (50 centipoises viscosity), 1% benzyl alcohol, and 0.6% Tween 80 (all obtained from Sigma Chemical Company). Concentration of drug in the dose solutions was 5, 15, and 50 mg/ml for the 10, 30, and 100 mg/kg doses, respectively, and was verified by liquid chromatography (LC). The 5 mg/ml dose was a clear solution and the higher concentrations were a translucent suspension. Dose volumes were 2.0 ml/kg. At various times after dosing, samples of blood were obtained by cardiac puncture with heparinized syringes, and plasma was prepared by centrifugation. Brains of rats were surgically excised, and all samples were frozen at −20° C. until analysis.

Aliquots of plasma (0.05 or 0.5 ml) were mixed with internal standard (50 µl of methanol containing 5 µg/ml a monofluoro analog of nepicastat, and 5 mg/ml dithiothreitol). Samples were mixed with 200 mM sodium phosphate buffer, pH 7.0, (0.5 ml) and extracted with 3 ml of ethyl acetate/hexane (1/1, v/v). The organic phase containing analytes was back extracted with 250 µl of 250 mM acetic acid and 100 µl aliquots of the aqueous phase were assayed by LC. The LC system used a Keystone Hypersil BDS 15 cm $C_8$ column at ambient temperature. Mobile phase A was 12.5 mM potassium phosphate, pH 3.0, with 5 mM dodecanesulfonic acid and mobile phase B was acetonitrile. Solvent composition was 40% B and was pumped at a flow rate of 1 ml/min. Detection was by UV absorption at 261 nm. Concentrations of analytes were determined from a standard curve generated from the analysis of plasma from untreated rats fortified with known concentrations of analyte. Plasma concentration data are expressed as µg (free base) per ml.

Brains were rinsed briefly with saline, blotted on a paper towel, then weighed (1.5-2.0 g). Internal standard was added (50 µl of methanol containing 20 µg/ml a monofluoro analog of nepicastat), and brains were homogenized in 5 ml of 200 mM sodium phosphate, pH 7.0, containing 0.5 mg/ml dithiothreitol. Aliquots of homogenate (2 ml) were extracted with 10 ml of ethyl acetate/hexane (1/1, v/v). The organic phase was gently back extracted with 150 µg of 250 mM acetic acid.

Following addition of 100 µl of methanol to the aqueous phase (to disperse any emulsion), 100 µl aliquots were assayed by LC as described for plasma. Level in brain are expressed as µg (free base) per g of brain tissue.

Pharmacokinetic parameters were calculated from mean plasma concentrations. Plasma half-life ($T_{1/2}$) was calculated as $0.693/\beta$, where $\beta$ is the elimination rate constant determined by linear regression of the log plasma concentration vs. time data within the terminal linear portion of the data. Areas under the plasma concentration vs. time curve (AUC) from zero to the time of the last quantifiable plasma concentrations were calculated by the trapezoidal rule. AUC from zero to infinity ($AUC_{total}$ 1 was calculated as:

$AUC_{total} = AUC(0-C_{last}) + C_{last}/\beta$ where $C_{last}$ is the last quantifiable plasma concentration.

Concentrations of nepicastat in plasma of male rats given 10, 30, or 100 mg/kg single oral doses were obtained. Concentrations of nepicastat in plasma increased with increasing dose, and the relationship between $AUC_{total}$ and dose was linear. The elimination half-life appeared to increase slightly at higher doses (1.70, 2.09, and 3.88 hr following the 10, 30, and 100 mg/kg oral doses to male rats, respectively). Following a 30 mg/kg oral dose of nepicastat to female rats, the plasma $AUC_{total}$ of nepicastat was 77% higher in female rats than in male rats given an equivalent dose of nepicastat. Levels of nepicastat in brain (expressed as µg/g) were initially lower than those in plasma (expressed as µg/ml). From 2 hr following dosing onward, however, concentrations of nepicastat in brain exceeded those in plasma.

Plasma levels of nepicastat in male rats increased linearly with increasing doses between 10 and 100 mg/kg, based on values of $AUC_{total}$.

Plasma levels of nepicastat were higher in female rats than in male rats following a 30 mg/kg oral dose.

Following administration of a 10 mg/kg oral dose of nepicastat to male rats, levels of nepicastat in brain were initially lower than those in plasma, but from 2 hr onward, levels of nepicastat in brain were greater than in plasma.

Example 10

The purpose of this study was to determine the 24 hours time course of the effects of nepicastat (10 mg/kg) on dopamine and norepinephrine levels in the mesenteric artery following a single oral dose in spontaneously hypertensive rats. Catecholamine levels were measured at 1, 2, 4, 6, 8, 12, 16, and 24 hours after a single oral administration of either nepicastat (10 mg/kg) or vehicle ($dH_2O$; 10 ml/kg).

Sixteen-17 week old, male spontaneous hypertensive rats (SHRs) weighing 300-400 grams were allowed food and water ad libitum. Animals were weighed and randomly assigned, the afternoon before the study, to one of the following treatment groups (n=9 per group): a single oral administration of nepicastat at 10 mg/kg or a single oral administration of vehicle (10 ml/kg) to be sacrificed at 1, 2, 4, 6, 8, 12, 16, or 24 hours.

Nepicastat was synthesized as the hydrochloride salt and nepicastat was dissolved in vehicle ($dH_2O$) to yield an oral dose that could be administered in repeated volumes of 10 ml/kg. All doses of nepicastat were administered as free base equivalents and prepared the morning of administration.

Animals were dosed every minute the morning of sacrifice. At 1, 2, 4, 6, 8, 12, 16 and 24 hours following administration, 9 treated animals and 9 vehicle animals were anesthetized with halothane, decapitated, and the left ventricle and mesenteric artery were rapidly harvested and weighed. The mesenteric artery was put in 0.5 ml of 0.4M perchloric acid in a centrifuge tube and the left ventricle put into an empty cryotube. Both tissues were immediately frozen in liquid nitrogen and stored at $-70°$ C. Mesenteric artery catecholamine levels were determined using HPLC with electrochemical detection. At the time of decapitation, plasma samples were taken by draining blood from the carcass into a tube containing heparin, and centrifuging at 4° C.

Each treatment group was compared to vehicle at each time point. A two way analysis of variance (ANOVA) with effects TRT, HARVEST and their interaction was performed. A one way ANOVA with factor TRT was performed for each harvest time. Pairwise analyses between treated and vehicle animals, at each time point, were carried out using Fisher's LSD strategy to control the experiment-wise error rate. Norepinephrine values were significantly ($p<0.05$) lower than vehicle only at the 4 hr time point. Levels were marginally ($0.05<p<0.1$) lower at the 6 hour time point. Dopamine levels were significantly ($p<0.05$) higher than those of vehicle at the 2 and 6 hr harvest times. The dopamine/norepinephrine ratio was significantly ($p<0.05$) greater than those of vehicle treated animals at the 1, 2, 4, 6 and 12 hour time points.

In general, nepicastat had few statistically significant effects on mesenteric artery norepinephrine or dopamine levels following a single oral administration at 10 mg/kg in spontaneously hypertensive rats at 1, 2, 4, 6, 8, 12, 16 or 24 hours following dosing. However, a consistent increase in the dopamine/norepinephrine ratios were observed across most of the first 12 hours of treatment. At the 16 and 24 harvest time no changes in any of the three parameters were observed.

Example 11

The purpose of this study was to determine the effects of intravenous administration of nepicastat (hereafter referred to as nepicastat) on the levels of dopamine and norepinephrine in the left ventricle in Sprague-Dawley rats. Animals received two intravenous (iv) administrations, 12 hours apart, of either vehicle (75% propylene glycol+25% DMSO; 1.0 ml/kg) or 15 mg/kg of nepicastat. Tissue norepinephrine and dopamine levels were measured six hours after the last compound administration.

Sixteen to 17 week old male Sprague-Dawley rats, weighing 300-400 grams, were allowed food and water ad libitum.

Animals were weighed and randomly assigned, the afternoon before the study, to one of the following treatment groups (n=10 per group): vehicle (1.0 ml/kg) or nepicastat at 15 mg/kg.

Nepicastat was synthesized and was dissolved in the appropriate amount of vehicle (75% propylene glycol+25% DMSO) to obtain a dosing volume of 1.0 ml/kg. Nepicastat was administered as the free base equivalent and prepared the afternoon prior to the first administration.

Each rat was dosed iv in the tail vein the afternoon before harvest. The dosing was repeated 12 hours later the following morning. Six hours after the final administration rats were anesthetized with halothane, decapitated, and the left ventricle was rapidly harvested and weighed. The ventricle was placed in 1.0 ml iced 0.4 M perchloric acid. Tissues were immediately frozen in liquid nitrogen and stored at −70° C. Tissue dopamine and norepinephrine concentrations were assayed by high performance liquid chromatography using electrochemical detection.

A one-way analysis of variance (ANOVA) with a main effect for treatment was performed for norepinephrine. A Kruskal-Wallis was performed for dopamine and their ratio primarily due to heterogeneous variances among treatment groups. Subsequent pairwise comparisons between nepicastat treated rats and vehicle were performed using Fisher's LSD test. A Bonferroni adjustment was performed on all p-values to ensure an overall experiment-wise type 1 error rate of 5%.

Nepicastat administered at 15 mg/kg significantly ($p<0.01$) decreased norepinephrine levels by 51%, and significantly ($p<0.01$) increased dopamine levels by 472%, and significantly ($p<0.01$) increased the dopamine/norepinephrine ratio by 1117%, compared to vehicle treated animals.

In conclusion, intravenous administration of nepicastat resulted in significant inhibition of DBH in the left ventricle of Sprague-Dawley rats.

Example 12

This study assessed the effectiveness of nepicastat in altering the levels of dopamine and norepinephrine in the cortex, left ventricle, and mesenteric artery of male spontaneously hypertensive rats (SHRs). Animals were given three doses, 12 hours apart at 3, 10, 30 or 100 mg/kg p.o.

This study also compared the efficacy of the S enantiomer (nepicastat) with the R enantiomer (Compound B) following three doses (30 mg/kg). This study also compared the effects of nepicastat with SKF-102698, a DBH inhibitor previously shown to be orally active in rats.

Compounds were prepared and administered as the free base equivalent. Nepicastat was dissolved in the appropriate amount of vehicle (dH$_2$O for nepicastat and PEG 400:dH$_2$O, 50:50 vol:vol for SKF-102698. Doses of 3, 10, 30, and 100 mg/kg of nepicastat, and 30 mg/kg SKF-102698 were prepared in 10.0 ml/kg dosing volumes.

Fifteen to sixteen week old male spontaneously hypertensive rats (SHRs) (Charles River Labs) were allowed food and water ad libitum. Animals were weighed and randomly assigned to one of the following treatment groups: 1) distilled water vehicle (dH$_2$O), or nepicastat at 3, 10, 30, and 100 mg/kg, 2) Compound B at 30 mg/kg in distilled water, or 3) PEG 400:dH$_2$O vehicle or SKF-102698 at 30 mg/kg. Each rat was dosed orally (p.o., using a gavage needle) three times 12 hours apart, beginning in the morning. At six hours after the third dose rats were anesthetized with halothane, decapitated, and the cortex, mesenteric artery, and left ventricle were rapidly harvested, weighed, placed in iced 0.4 M perchioric acid, frozen in liquid nitrogen, and stored at −70° C. Tissue dopamine and norepinephrine concentrations were assayed by high performance liquid chromatography and electrochemical detection.

Four series of statistical analyses were performed. The first series compared the rats treated with various doses of nepicastat, and Compound B at 30 mg/kg to the vehicle control animals. A nonparametric one-way analysis of variance (ANOVA) with factor Dose and blocking factor Day was performed for each tissue and strain separately. Overall results are reported. Pairwise analysis between treated and controls at each dose were carried out using Dunnett's test to control the experiment-wise error rate. The second statistical test compared SKF-102698 to the PEG-dH$_2$O vehicle treated group using a nonparametric t-test. The third statistical test compared Compound B to nepicastat at doses of 30 mg/kg using a nonparametric t-test. A fourth statistical analysis compared nepicastat to SKF-102698 at doses of 30 mg/kg. Since two different vehicles were used, a linear contrast was developed which calculates the difference of differences as follows:

$$\text{Change} = (30 \text{ mg/kg} - \text{Vehicle})_{NEPICASTAT} - (30 \text{ mg/kg} - \text{Vehicle})_{SKF-102698}$$

This new variable was tested for equality to zero by the SAS procedure General Linear Models.

The dopamine concentration in the cerebral cortex was significantly ($p<0.05$) greater, the norepinephrine concentration was significantly ($p<0.05$) lower), and the dopamine/norepinephrine ratios significantly ($p<0.05$) greater than vehicle at doses of 30 and 100 mg/kg of nepicastat.

Dopamine concentration in the left ventricle was significantly ($p<0.05$) greater than vehicle at doses of 3, 10, 30 and 100 mg/kg. Norepinephrine concentration was significantly ($p<0.05$) lower than vehicle at doses of 10, 30 and 100 mg/kg. The dopamine/norepinephrine ratio in the left ventricle was significantly ($p<0.05$) greater than vehicle at doses of 3, 10, 30, and 100 mg/kg of nepicastat.

Dopamine concentration in the mesenteric artery of SHRs was significantly ($p<0.05$) greater than vehicle at doses of 3, 10, 30 and 100 mg/kg. Norepinephrine concentration was not significantly less ($p>0.05$) than vehicle at 10, 30, and 100 mg/kg. The dopamine/norepinephrine ratios in the mesenteric artery were significantly ($p<0.05$) greater than vehicle at all doses of nepicastat.

In the cerebral cortex, relative to treatment with vehicle, Compound B resulted in significant increase in both dopamine and norepinephrine ($p<0.01$), and had no effect on the dopamine/norepinephrine ratio. Norepinephrine levels were significantly lower with nepicastat compared to Compound B ($p<0.01$).

In the left ventricle, relative to treatment with vehicle, Compound B resulted in a significant increase in dopamine and the dopamine/norepinephrine ratio ($p<0.01$), but did not significantly lower norepinephrine levels. Nepicastat was significantly more effective ($p<0.01$) than Compound B at lowering norepinephrine levels, and increasing dopamine and the dopamine/norepinephrine ratio.

In the mesenteric artery, relative to treatment with vehicle, Compound B resulted in a significant increase in dopamine and the dopamine/norepinephrine ratio ($p<0.01$), but did not significantly lower norepinephrine levels. Nepicastat was significantly more effective ($p<0.01$) than Compound B at lowering norepinephrine levels, and increasing dopamine and the dopamine/norepinephrine ratio.

Comparing nepicastat with SKF-102698 at 30 mg/kg in the cerebral cortex, dopamine concentration in the cortex was significantly greater (p<0.01) than vehicle for SKF-102698 at a dose of 30 mg/kg. The increase above vehicle was greater for SKF-102698 than for nepicastat (p<0.01). Norepinephrine concentration was significantly lower than vehicle for SKF-102698, and the decrease was greater for SKF-102698 than for nepicastat (p<0.01). The dopamine/norepinephrine ratios in the cortex were significantly (p<0.01) greater than vehicle for SKF-102698, and the increase above vehicle was greater for SKF-102698 than for nepicastat (p<0.01).

The dopamine concentration in the left ventricle was significantly greater (p<0.01) than vehicle for SK-F102698, and the increase above vehicle was greater for nepicastat than for SKF-102698 (p<0.01). Norepinephrine concentration was not different from vehicle with SKF-102698 treatment, however treatment with nepicastat significantly lowered norepinephrine relative to vehicle more than SKF-102698 (p<0.01). The dopamine/norepinephrine ratios in the left ventricle were significantly (p<0.05) greater than vehicle for SKF-102698, and the increase above vehicle was greater for nepicastat than for SKF-102698 (p<0.05).

The dopamine concentration in the mesenteric artery was significantly greater than vehicle for SKF-102698, and the increase above vehicle was greater for NEPICASTAT than for SKF-102698. Norepinephrine concentration was significantly lower than vehicle with SKF-102698 treatment, and treatment with nepicastat significantly lowered norepinephrine relative to vehicle more than SKF-102698. The dopamine/norepinephrine ratios in the left ventricle were significantly greater than vehicle than for SKF-102698, and the increase above vehicle was greater for nepicastat than for SKF-102698.

In conclusion, the data show that nepicastat is a potent inhibitor of DBH in vivo in the mesenteric artery, left ventricle, and cerebral cortex of SHRs six hours after the third of three oral doses administered 12 hours apart. The S enantiomer, nepicastat was more potent than the R enantiomer (Compound B) in all three tissues at 30 mg/kg. Furthermore, nepicastat was more effective than SKF-102698 in the mesenteric artery and left ventricle, but less effective in the cerebral cortex, following three doses at 30 mg/kg administered over 24 hours.

Example 13

Nepicastat was prepared and administered as the free base equivalent. Nepicastat and methimazole were dissolved in vehicle (66.7% propylene glycol:33.3% dH2O) to yield dosing solutions of appropriate concentrations so that all doses could be administered in a 1.0 ml/kg volume.

Male Sprague-Dawley rats, weighing 180-200 grams, were fed an iodine deficient diet (Purina, 5891C, Lot 1478, 0.066±0.042 mg iodine/kg sample) ad libitum 14 days prior to treatment. Animals were weighed and randomly assigned to one of the following treatment groups (n=12 per group): nepicastat at 2.0 mg/kg, nepicastat at 6.2 mg/kg, Methimazole at 1 mg/kg, or vehicle at 1 ml/kg. Each group of rats was dosed orally in the evening and the following morning, approximately 12 hours apart, for 10 consecutive days.

At four hours after the second dose, on day 10, rats were anesthetized with halothane, decapitated, and the cortex, striatum, and mesenteric artery were harvested and weighed. Tissue samples were not harvested from the methimazole groups as they only served as positive controls for determination of thyroid function. The mesenteric artery, cortex, and striatum were immediately placed in 0.4 M iced perchloric acid and analyzed for norepinephrine and dopamine levels the same day using HPLC.

Orbital blood samples were taken at day −3, 0, 3, 7, and 9 (day 0 was the first day of dosing). Serum samples were analyzed for $T_3$ and $T_4$ levels using a radioimmunoassay.

To statistically evaluate changes in $T_3$ and $T_4$ levels, a change from baseline was calculated from the day −3 time point. A non-parametric two-way within subject analysis of variance (ANOVA) was conducted. Also a one-way ANOVA was performed to detect if a significant difference from control occurred. Pairwise analyses between controls and each treatment group were carried out using Fisher's LSD strategy to control the experiment-wise error rate. For statistical analysis of catecholamine levels, a one-way ANOVA with factor DOSE was performed. Pairwise analyses between treated and controls at each dose were carried out using Fisher's LSD strategy to control the experiment-wise error rate.

Norepinephrine levels in the nepicastat treated animals were not significantly (p>0.05) different in the cortex compared to vehicle control at doses of 2.0 and 6.2 mg/kg. Norepinephrine levels in the mesenteric artery were significantly (p<0.05) lower at the 2.0 and 6.2 mg/kg dose groups, and norepinephrine levels in the striatum were marginally (p<0.10) lower in both the 2.0 and 6.2 mg/kg dose groups, compared to vehicle control.

Dopamine levels in all three tissues were not significantly (p>0.05) different from vehicle control at either the 2.0 or 6.2 mg/kg dose group of nepicastat.

The dopamine/norepinephrine ratio of the cortex and striatum at 2.0 and 6.2 mg/kg nepicastat were not significantly (p>0.05) different from vehicle control, while the ratio of the mesenteric artery at both 2.0 and 6.2 mg/kg nepicastat were significantly (p<0.05) higher than vehicle control.

Neither 2.0 or 6.2 mg/kg nepicastat affected thyroid function by altering free $T_3$ or total $T_4$ levels in the rat serum. A dose of 1.0 mg/kg of Methimazole, the positive control, significantly (p<0.05) lowered $T_3$ levels on all treatment days and $T_4$ levels at day 3 and 7, compared to vehicle control. $T_4$ levels of the methimazole treated animals were only marginally (p<0.10) lower on day nine.

Nepicastat (2.0 or 6.2 mg/kg) did not cause any significant (p>0.05) changes in dopamine or the norepinephrine levels, or dopamine/norepinephrine ratio when compared to vehicle. In the striatum, a marginally significant (p<0.10) decrease in norepinephrine level was observed in the 6.2 mg/kg dose group, but no other significant changes were observed. In the mesenteric artery, both 2.0 and 6.2 mg/kg of nepicastat produced significantly (p<0.05) lower norepinephrine levels and significantly (p<0.05) higher dopamine/norepinephrine ratios, compared to vehicle, with no significant changes observed in dopamine levels. Thus nepicastat appears to be an effective inhibitor of dopamine β-hydroxylase in vivo, with greater effect in the mesenteric artery than the cerebral cortex or striatum following 10 days of dosing in Sprague-Dawley rats.

Example 14

This study was performed to determine the dopamine and norepinephrine concentrations in kidney medulla and kidney cortex from dogs dosed with nepicastat. Adult male beagle dogs were randomly assigned to four groups of 8 dogs per group and dosed by oral administration with nepicastat. Nepicastat was delivered in doses of 5, 15 and 30 mg/kg placed in single capsules. Vehicle was an empty capsule. Each dog received 2 doses daily, morning and afternoon (8-10 hours apart) for four days. On the fifth day, each dog received a single dose in the morning and the dogs were euthanized six hours after the last dose. Samples of kidney medulla and kidney cortex were rapidly harvested, weighed, placed in cold 0.4 M perchloric acid, frozen in liquid nitrogen and stored at −70° C.

To quantitate concentrations of norepinephrine (NE) and dopamine (D), each tissue was homogenized by brief sonication in 0.4 M perchloric acid. After sonication, the homogenates were centrifuged at 13,000 rpm in a microfuge for 30 minutes at 4° C. An aliquot of each supernatant was removed and spiked with 3,4-dihydroxybenzylamine (DHBA) as internal standard. The extract from each sample was subjected to HPLC separation using electrochemical detection. The method has a quantitation limit of 2.0 ng/mL and a linear range of 2.0 ng/mL to 400 ng/mL for each analyte.

Each analyte determination was normalized to the weight of the tissue sample and expressed as μg of analyte per gram of tissue. The concentrations of dopamine, norepinephrine and the ratio of dopamine concentration to norepinephrine concentration (D/NE) were obtained for each dog. In addition, the calculated means and standard deviations for each analyte and D/NE ratio were provided for each treatment group.

Example 15

Male Beagle dogs (Marshall farms, North Rose, N.Y.) weighing between 9-16 kg were used in the study. The animals were allowed water ad libitum and given food once daily at ~10.00 AM. Animals were randomly assigned to one of the following treatment groups (n=8/group): placebo (empty capsule), or nepicastat at 2 mg/kg b.i.d (4 mg/kg/day). Each animal received 2 doses daily, morning and afternoon (8-10 hours apart). Daily blood samples (10 ml) were drawn 6 h after the AM dose for measurement of plasma levels of nepicastat and catecholamines. The blood was collected in tubes containing heparin and glutathione and centrifuged at −4° C. within 1 h of collection. The plasma was separated and divided into two samples, one for the measurement of plasma catecholamines and the other for analysis of nepicastat.

Tissue samples were also taken from the dogs at the end of the study in case it was deemed necessary to analyze tissue catecholamines at a later point. On day 15, 6 hours after the AM dose, a final blood sample (10 ml) was taken. Dogs were anesthetized with sodium pentobarbital (40 mg/kg, iv), placed on a necropsy table and euthanized with a second injection of pentobarbital (80 mg/kg,iv). A rapid bilateral transthoracotomy and abdominal incision was performed. Biopsies were taken from the renal artery and left ventricle. The skull was opened to expose the frontal lobe of the cerebral cortex and a biopsy was taken. Tissue samples were weighed, placed on iced 0.4 M perchloric acid, frozen in liquid nitrogen and stored at −70° C. until analyzed.

Plasma norepinephrine (NE), dopamine (DA) and epinephrine (EPI) were analyzed by HPLC using electrochemical detection. Plasma concentration of nepicastat was determined by HPLC using electrochemical detection.

The Box-Cox transformations indicated that the logarithm was an appropriate variance stabilizing transformation; hence all analyses were performed on the log-values. The BQL (below quantitation limit) in the DA concentration of dog 1 at day 10 was set to 0; 1n (0) was set to missing. The analysis was performed using a mixed model (using PROC MIXED) with the day and treatment categorical variables being fixed and the dog within treatment being a random factor. For the fixed effects, the interaction between the day and the treatment was included, since the difference between the drug and placebo groups varies from day to day. Contrasts were calculated using the CONTRAST statement, which correctly takes into account the error terms for each particular contrast. In particular, the contrasts comparing the treatment group to the drug group uses the dog mean square for its error term, while the comparisons used to establish steady state are all within dog comparisons, and require the error mean square.

The time period of steady state was calculated using the Helmert transformation (cf. SAS PROC GLM manual). These transformations compare each treatment mean with the average of the treatment means of the time points following. The steady state period is defined to start at the first time point following the maximum time at which the Helmert contrast is statistically significant. However, since this method can fail to detect a smoothly changing process, as appears might be the case here, the slope of the analyte concentration during the steady state period also was calculated. The slope during the steady state period was calculated for each dog individually, yielding one slope per animal. Univariate statistics on the slopes were then calculated, with Normal theory confidence intervals built on the mean slope, and the hypothesis of slope equaling zero was tested, and its Normal theory p-value was calculated. This slope analysis was used as the basis for determining whether the steady state period was a period of changing concentration.

When compared to the placebo group, nepicastat (2 mg/kg, b i d) produced significant decreases in plasma NE (2.1 fold) and EPI (1.91 fold) and significant increases in plasma DA (7.5 fold) and DA/NE ratio (13.6 fold).

The peak decreases in plasma NE and EPI were observed at day 6 and day 8, respectively, whereas the peak increases in plasma DA and DA/NE ratio were observed at day 7 and day 6, respectively. The effects on plasma NE, DA and EPI attained steady-state at approximately 4, 8 and 6 days post-dose, respectively. The changes in plasma DA and DA/NE ratio were significantly different from placebo on all days post-dose. The changes in plasma NE were significantly different from placebo on days 4-9 and days 11-13 post dose. The changes in plasma EPI were significantly different from placebo on days 7-9 and day 12 post-dose.

Administration of nepicastat (2 mg/kg, bid) produced significant plasma levels of the drug on all days. The peak levels were observed at 2 days post-dose. No significant levels of the N-acetyl metabolite of nepicastat were detected on any of the days.

Chronic (14.5 days) administration of nepicastat (2 mg/kg, bid, po) produced significant decreases in plasma NE and EPI and significant increases in plasma DA and DA/NE ratio. These changes reflect inhibition of the sympathoadrenal system via inhibition of the enzyme dopamine β-hydroxylase.

Example 16

Nepicastat was weighed and put into capsules (size 13—Torpac; East Hanover, N.J.) to yield doses of 5, 15, and 30 mg/kg per capsule (given b.i.d. to yield doses of 10, 30 and 60 mg/kg/day). The initial dog weight was used to determine the dose for each animal. Dogs receiving 0 mg/kg/day received empty capsules (placebo). All doses of nepicastat were administered as free base equivalents.

Thirty-two male beagle dogs, weighing 10-12 kg, were randomly assigned to one of the following 4 treatment groups (n=8 per group): nepicastat at 0 mg/kg/day (placebo), 10 mg/kg/day (5 mg/kg b.i.d.), 30 mg/kg (15 mg/kg b.i.d.), or 60 mg/kg/day (30 mg/kg b.i.d.). Dog numbers 1-16 were assigned as dose group A and dog numbers 17-32 as dose group B. The terminal surgery for tissue harvest was performed over 2 days with 16 animals studied per day. Two or 3 days before the first compound administration each dog was weighed and skin regions overlying both cephalic, saphenous and jugular veins were shaved. Dosing consisted of oral administration of one capsule with the second given 8-10 hr later. Dogs were dosed as scheduled on days 1-3. On day 4, prior to the AM dose, 3 ml of blood were obtained from a jugular vein for determination of baseline plasma compound levels. The dog was then administered the AM dose, and at 1, 2, 4 and 8 hr following the dose additional 3 ml blood samples were collected for determination of plasma compound levels. Blood samples were put into tubes containing heparin, centrifuged at 4° C. and stored at −20° C. until analysis. The PM dose was then administered as scheduled. The AM dose was administered as scheduled on the days of surgery. Approximately 6 hr after the AM dose, a final 3 ml blood sample was taken from the jugular vein for determination of plasma compound levels. The dog was then anesthetized with pentobarbital Na (~40 mg/kg), given i.v. in a cephalic or saphenous vein, and delivered to the necropsy room where an additional dose of pentobarbital Na was given (~80 mg/kg, iv). The left ventricle, renal artery, kidney, renal medulla, renal cortex and cerebral cortex were then rapidly harvested, weighed, put into 2 ml iced 0.4M perchloric acid, frozen in liquid nitrogen and stored at −70° C. until analysis for catecholamines by HPLC using electrochemical detection. All tissue samples were divided into 2 portions, the second of which were immediately frozen in liquid nitrogen and stored at −70° C. for determination of tissue compound levels. A third transmural sample taken from the left ventricle was immediately frozen in liquid nitrogen and stored at −70° C. for use in receptor binding studies.

Ventricles were homogenized in 50 mM Tris-HCl, 5 mM $Na_2EDTA$ buffer (pH 7.4 at 4° C.) using a Polytron P-10 tissue disrupter (setting 10, 2×15 second bursts). Homogenates were centrifuged at 500×g for 10 minutes and the supernatants stored on ice. The pellets were washed by resuspension and centrifugation at 500×g and the supernatants combined. The combined supernatants were centrifuged at 48,000×g for 20 minutes. The pellets were washed by resuspension and centrifugation once in homogenizing buffer and twice in 50 mM Tris-HCl, 0.5 mM EDTA buffer (pH 7.4 at 4° C.). Membranes were stored at −70° C. until required. Saturation experiments were conducted using [$^3$H] CGP-12177 in buffer containing 50 mM Tris-HCl, 0.5 mM EDTA (pH 7.4 at 32° C.). Non-specific binding was defined by 10 µM isoproterenol. Total bound, non-specific bound and total count tubes were set up for eight concentrations of [$^3$H] CGP-12177 ranging from 0.016 nM to 2 nM. Samples were incubated at 32° C. for 60 minutes. Samples were filtered over 0.1% PEI pre-treated GF/B glass fiber filtermats using a Brandel cell harvester. Samples wee washed with room temperature water three times for 3 seconds. Aquasol scintillation fluid was added to each vial and radioactivity determined by liquid scintillation counting. Saturation binding isotherms were analyzed after first converting total ligand concentrations to free ligand concentrations (total−bound=free). Individual saturation isotherms were completed for each tissue. Membranes were assayed for protein using the Bio-Rad protein binding method and using gamma globulin as the standard. Receptor densities were expressed, per mg protein, as mean for each treatment group. Tissue catecholamine levels were analyzed by comparing nepicastat-treated groups with the placebo (control) treated groups. A nonparametric one-way analysis-of-variance (ANOVA) with factor DOSE was performed for each tissue and each catecholamine measure separately. Pairwise analyses between treated and controls at each dose were carried out using Dunnett's test to control the experiment-wise error rate. Student-Neuman-Kuels and Fisher's LSD tests were performed as validation. Analysis of tissue and plasma compound levels were performed in 2 ways. First, individual t-tests were run to compare each dose level to a factored level of its partner dose for each parameter. For example, three times the level of compound present at 10 mg/kg in a particular tissue or plasma should be comparable to the compound level observed in the 30 mg/kg group. Additionally, a linear orthogonal contrast was calculated for all three doses within the context of a one-way ANOVA. A paired t-test was used to determine any differences in binding between the vehicle treated group and the 10 mg/kg/day nepicastat group.

Dogs were orally administered 0, 5, 15, or 30 mg/kg nepicastat capsules b.i.d. to yield doses of 10, 30, and 60 mg/kg/day for 4.5 days and tissue was harvested 6 hr after the final administration. In the renal artery, nepicastat administered at doses of 10, 30 and 60 mg/kg/day significantly (p<0.01) decreased norepinephrine levels by 86%, 81% and 85%, respectively. Dopamine levels were significantly (p<0.01) increased at doses of 10, 30 and 60 mg/kg/day by 180%, 273% and 268%, respectively. Doses of 10, 30 and 60 mg/kg/day nepicastat significantly (p<0.01) increased the dopamine/norepinephrine ratio by 1711%, 1767% and 1944%, respectively, compared to placebo. Following administration of 10 and 60 mg/kg/day nepicastat, dopamine levels were significantly (p<0.01) increased 632% and 411%, respectively in the cerebral cortex. The dopamine/norepinephrine ratio was significantly (p<0.01) increased 531% after 10 mg/kg/day nepicastat and 612% following administration of 60 mg/kg/day nepicastat. Norepinephrine levels were not significantly (p>0.01) affected at these 2 doses. At 30 mg/kg/day, norepinephrine was significantly (p<0.01) reduced by 63% and the ratio significantly (p<0.01) elevated by 86%, while dopamine levels marginally (0.05<p<0.10) increased 174%, compared to placebo. Following administration of 10, 30 and 60 mg/kg/day nepicastat, norepinephrine levels were significantly (p<0.01) decreased by 85%, 58% and 79%, respectively in the left ventricle. The dopamine/norepinephrine ratio significantly (p<0.01) increased 852%, 279% and 607%, respectively, compared to placebo animals. No significant changes were observed in dopamine levels at doses of 10, 30, and 60 mg/kg/day nepicastat.

In the renal cortex, compared to placebo, norepinephrine levels were significantly decreased (p<0.01) by 86%, 66% and 85%, respectively, following doses of 10, 30 and 60 mg/kg/day nepicastat. Dopamine levels were significantly (p<0.01) increased 156%, 502% and 208%, respectively, at these doses. The dopamine/norepinephrine ratio significantly (p<0.01) increased by 1653%, 1440% and 1693%, respectively, at doses of 10, 30, and 60 mg/kg/day. In the renal medulla, the dopamine/norepinephrine ratios were significantly (p<0.01) increased by 555%, 636% and 677%, respectively, at doses of 10, 30 and 60 mg/kg/day nepicastat, compared to placebo. Dopamine levels were significantly (p<0.01) increased 522% at 30 mg/kg/day and marginally (0.05<p<0.10) increased by 150% and 156%, respectively, at 10 and 60 mg/kg/day. Norepinephrine levels were significantly (p<0.01) decreased 72% following administration of 10 mg/kg/day nepicastat, compared to placebo, and marginally (0.05<p<0.10) decreased by 69% following 60 mg/kg/day.

Statistical analysis indicated that the concentration of nepicastat in plasma obtained on Day 4 and tissue and plasma obtained on Day 5 was dose-proportional between each dose level and factored levels of its partner dose. Therefore, dose points were determined to be linear, with the following exceptions (a significant result would suggest the data are not linear):

Kidney medulla: 3×10<30 (p<0.05)
Kidney medulla: 6×10<60 (p=0.077)
Plasma (day 4): 2×30>60 (p=0.076)

On Day 5, levels of nepicastat in all tissues examined were higher than those in plasma.

The results demonstrated no difference between left ventricular samples from the 10 mg/kg/day nepicastat treated group and vehicle treated group.

Example 17

Nepicastat was evaluated for its activity at a range of enzymes including tyrosine hydroxylase, NO synthase, phosphodiesterase III, phospholipase $A_2$, neutral endopeptidase, $Ca^{2+}$/calmodulin protein kinase II, acetyl CoA synthetase, acyl CoA-cholesterol acyl transferase, HMG-CoA reductase, protein kinase (non-selective) and cyclooxygenase-I. As shown in FIG. 4, nepicastat had an $IC_{50}$ of >10 μM at all the 12 enzymes studied, and therefore it is a highly selective (>1000-fold) inhibitor of dopamine-β-hydroxylase.

Example 18

Bovine DBH from adrenal glands was obtained from Sigma Chemicals (St. Louis, Mo.). Human secretory DBH was purified from the culture medium of the neuroblastoma cell line SK-N-SH and was used to obtain the inhibition data. A lentil lectin-sepharose column containing 25 ml gel was prepared and equilibrated with 50 mM $KH_2PO_4$, pH 6.5, 0.5 M NaCl. The column was eluted with 35 ml of 10% methyl a, D-mannopyranoside in 50 mM $KH_2PO_4$, pH 6.5, 0.5 M NaCl at 0.5 ml/min. Fraction containing most enzymatic activities were pooled and concentrated with an Amicon stirred cell using a YM30 membrane. Methyl a, D-mannopyranoside was removed by buffer exchange with in 50 mM $KH_2PO_4$, pH 6.5, 0.1M NaCl. The concentrated enzyme solution was aliquoted and stored at −25° C.

An HPLC assay was used to measure DBH activity using tyramine and ascorbate as substrates. The method is based on the separation and quantitation of tyramine and octopamine by reverse phase HPLC chromatography (Feilchenfeld, N. B., Richter, H. & Waddell, W. H. (1982). Anal. Biochem: A time-resolved assay of dopamine (3-hydroxylase activity utilizing high-pressure liquid chromatography. 122: 124-128.). The assay was performed at pH 5.2 and 37° C. in 0.125 M NaAc, 10 mM fumarate, 0.5~2.0 μM $CuSO_4$, 0.1 mg/ml catalase (6,500 u, Boeringer Mannheim, Indianapolis, Ind.), 0.1 mM tyramine, and 4 mM ascorbate. In a typical assay, 0.5-1.0 milli-units of enzyme were added to the reaction mixture and then a substrate mixture containing catalase, tyramine and ascorbate was added to initiate the reaction (final volume 200 μl). Samples were incubated at 37° C. for 30~40 minutes. The reactions were quenched by the stop solution containing 25 mM EDTA and 240 μM 3-hydroxytyramine (internal standard). The samples (150 μl) were loaded to a Gilson autosampler and analyzed by HPLC using UV detection at 280 nm. PC-1000 software (Thermo Separations products, Fremont, Calif.) was used for integration and data analysis. The HPLC run was carried out at the flow rate of 1 ml/min using a LiChroCART 125-4 RP-18 column and isocratic elution with 10 mM acidic acid, 10 mM 1-heptanesulfonic acid, 12 mM tetrabutylammonium phosphate, and 10% methanol. The remaining percent activity was calculated based on the control without inhibitor, corrected using internal standards and fitted to a nonlinear 4 parameter dose response curve to obtain the $IC_{50}$ values.

Purification of [$^{14}$C]-Tyramine. [$^{14}$C]Tyramine hydrochloride was purified by a C18 light load column (two columns combined into one) that was washed with 2 ml of MeOH, 2 ml of 50 mM $KH_2PO_4$, pH 2.3, 30% acetonitrile, and then 4 ml of 50 mM $KH_2PO_4$, pH 2.3. A vacuum manifold (Speed Mate 30, from Applied Separations) was used to wash and elute the column by vacuum. After loading of [$^{14}$C]tyramine, the column was washed with 6 ml of 50 mM $KH_2PO_4$, pH 2.3 and eluted with 2 ml of 50 mM $KH_2PO_4$ containing 30% acetonitrile. The eluate was lyophilized to remove acetonitrile, resuspended in $H_2O$, and stored at −20° C.

Enzyme Assay by Radioactive Method. Enzymatic activity was assayed using [$^{14}$C]tyramine as substrate and a C18 column to separate the product. The assay was performed in 200 ml volume containing 100 mM NaAc, pH 5.2, 10 mM fumaric acid, 0.5 μM $CuSO_4$, 4 mM ascorbic acid, 0.1 mg/ml catalase and various concentrations of tyramine. The total counts of each reaction was ~150,000 cpm. Bovine DBH (0.18 ng for each reaction) was mixed with tyramine and inhibitor in the reaction buffer at 37° C. The reaction was initiated by the addition of ascorbate/catalase mixture and was incubated at 37° C. for 30 minutes. The reaction was stopped by the addition of 100 ml of 25 mM EDTA, 50 mM $KH_2PO_4$, pH 2.3. Entire mixture was loaded to a C18 light load column (two combined into one) that was prewashed with MeOH and equilibrated with 50 mM $KH_2PO_4$, pH 2.3. Elution into scintillation vials was carried out with 1 ml of $KH_2PO_4$, pH 2.3 buffer twice, followed by 2 ml of the same buffer. ReadySafe scintillation fluid (16 ml) was added to the scintillation vials and the samples were counted for $^{14}$C radioactivity.

Nepicastat concentrations of 0, 1, 2, 4, 8 nM were used to study inhibition kinetics at the following tyramine concentrations: 0.5, 1, 2, 3, 4 mM. The $^{14}$C counts were identical in each reaction which was carried out as described above. A blank control without the enzyme was used to obtain the background. The data were corrected for background, converted to activity in nmol/min, and plotted (1/V vs 1/S). Km' was calculated from the slopes and Y intercepts and linear regression was used to obtain Ki value.

The $IC_{50}$ values for SKF-102698, nepicastat and Compound B against human and bovine DBH were obtained using the HPLC assay at the substrate concentrations of 0.1 mM tyramine, 4 mM ascorbate at pH 5.2 and 37° C. All three compounds caused a dose-dependent inhibition of DBH activity on both bovine and human enzyme.

The $IC_{50}$ values calculated for nepicastat, Compound B and SKF-102698 showed that the S enantiomer (nepicastat) was more potent than the R enantiomer (Compound B by 3-fold against bovine DBH and 2-fold) against the human enzyme. Nepicastat was more potent than SKF-102698 by 8-fold against bovine enzyme, and 9-fold against human DBH.

A Km of 0.6 mM was determined from the Lineweaver-Burk plot. Nepicastat (1-8 nM) caused a major shift in Km, as would be predicted for a competitive inhibitor. The inhibition of bovine DBH by nepicastat appears to be competitive with tyramine. A Ki of 4.7±0.4 nM was calculated by linear regression.

Nepicastat was a potent inhibitor of both human and bovine DBH. It was 8-9-fold more potent than SKF-102698. nepicastat (the S enantiomer) is 2-3 fold more potent than Compound B (the R enantiomer). The inhibition of bovine DBH by nepicastat appeared to be competitive with tyramine, with a Ki of 4.7±0.4 nM.

Example 19

The affinity of nepicastat was determined in the bindings assays outlined using standard radioligand filtration binding methods were used.

Competition binding data were analyzed by iterative curve fitting to a four parameter logistic equation. Hill coefficients and $IC_{50}$ were obtained directly. pKi (−log of Ki) of competing ligands were calculated from $IC_{50}$ values using the Cheng-Prusoff equation.

Nepicastat had moderate affinity for alpha$_1$ receptors (pKi of 6.9-6.7). The affinity at all other receptors examined was relatively low (pKi<6.2).

Example 20

At the time of dosing, a 60-mg/ml nepicastat formulation was prepared by mixing vehicle with nepicastat powder, followed by shaking. The 6- and 20-mg/ml Nepicastat formulations were prepared by diluting the 60-mg/ml formulation with vehicle. The reconstituted nepicastat formulations retained potency for the duration of use. The aqueous vehicle and nepicastat formulations contained hydroxypropylmethylcellulose, benzyl alcohol, and polysorbate 80.

Dose selection was based on an acute toxicity study in which mice were administered single oral doses of 250, 1000, or 2500 mg/kg of nepicastat. Clinical signs of toxicity and death occurred at 1000 and 2500 mg/kg.

A single oral dose of vehicle or nepicastat formulation was administered by gavage to each mouse using a rodent intubator. The oral route was selected because it is a proposed clinical route of administration. Dose volumes were calculated on the basis of individual body weights recorded before dosing (body weight data are not tabulated in this report). Food and water were withheld from the mice 2.5 to 3.5 hours before dosing, instead of 1.5 hours as specified in the protocol. This deviation did not affect the integrity of the study.

Clinical observations were recorded before dosing. Beginning 60 minutes after dosing, mice in each treatment group were evaluated in groups of up to 3 over an interval of approximately 10 minutes each for clinical observations and protocol-specified behavioral tests. One mouse in the 30-mg/kg group and 1 mouse in the 100-mg/kg group died after dosing and they were removed from the study. Surviving mice were euthanatized and removed from the study at the end of the observation/testing period.

Mice in groups of 6 males each were administered single oral doses of 0 (vehicle), 30, 100, or 300 mg/kg of nepicastat by gavage. Clinical observations and behavioral tests were initiated 60 minutes after administration of the test formulation. At the end of the observation period, all surviving mice were euthanatized and removed from the study.

Lower body temperatures were present in the 30-, 100-, and 300-mg/kg groups compared with the vehicle-control group. No treatment-related clinical or gross behavior changes were present. Rectal body temperature data are and observation and behavioral test data were obtained. No treatment-related clinical or gross behavioral changes were present. Abnormal social grouping (listed as other reaction) occurred among mice in the 100-mg/kg group, but not the 300-mg/kg group; this finding was considered incidental. Clinical/behavioral changes in 1 mouse in the 100-mg/kg group included inactivity, abnormal gait and posture, decreased induced activity, abnormal passivity, and soft/continuous vocalization; these changes were not attributed to nepicastat. One mouse each in the 30- and 100-mg/kg group died after dosing; the deaths were considered incidental and the mice were removed from the study.

Example 21

The purpose of this study was to determine if the DBH inhibitors SKF-102698 and nepicastat produced changes in locomotor activity or acoustic startle reactivity. Changes in these behaviors may therefore reflect activity of these compounds in the central nervous system.

Adult male Sprague Dawley rats (250-350 g on study day) were obtained from Charles Rivers Labs. Rats were housed under a normal light/dark cycle with lights on between 0900 Hrs. and 2100 Hrs. Animals were housed in pairs in standard metal wire cages, and food and water were allowed ad libitum.

The locomotor activity boxes consisted of a Plexiglas box measuring 18"×18" by 12" high. Surrounding the Plexiglas® boxes were Omnitech Digiscan Monitors (model # RXXCM 16) which consisted of a one inch ban of photobeams and photosensors numbering 32 per box. The number of photobeam breaks were analyzed by an Omnitech Digiscan Analyzer (model # DCM-8). The animals were tested in an enclosed room with a white noise generator running to mask extraneous noise.

Acoustic startle reactivity tests were conducted in eight SR-Lab (San Diego Instruments, San Diego, Calif.) automated test stations. The rats were placed individually in a Plexiglas® cylinder (10 cm diameter) which is housed in a ventilated sound-attenuating enclosure. Acoustic noise bursts (a broad band noise with a rise time and fall time of 1 msec) was presented via a speaker mounted 30 cm above the animal. A piezoelectric accelerometer transforms the subject's movement into an arbitrary voltage on a scale of 0 to 4095.

Prior to drug administration, each of seventy-two rats was placed in the startle apparatus, and after a 5 minute adaptation period they were presented with an acoustic noise burst every 20 seconds for 15 minutes (45 startles total). The average startle was calculated for each rat by taking the mean of startle number 11 through 45 (the first ten startles will be disregarded). Sixty-four of these rats were then placed in one of eight treatment groups such that each group had similar mean startle values. The eight treatment groups were as follows: SKF-102698 (100 mg/kg) and its vehicle (50% water/50% polyethylene glycol), clonidine (40 µg/kg), nepicastat (3, 10, 30 and 100 mg/kg), and their vehicle, $dH_2O$. Previous work has shown that this matching procedure to be the most appropriate for startle since there is significant variability in startle response between rats, but a high degree of consistency within rats from one day to the next.

Each day after this testing procedure, eight rats (one rat from each of the eight treatment groups) was injected with their assigned drug treatment and immediately placed individually in a motor activity box. The rats motor activity was monitored for four hours. Next, the rats were placed in a transfer cage for fifteen minutes. At the beginning of this fifteen minutes the rat that has been assigned the clonidine treatment will receive another injection of 40 µg/kg. Next, the rats were placed in the startle apparatus, and after a five minute acclimation period they were presented with a 90 dB noise burst every minute for four hours.

To evaluate motor activity, horizontal activity (number of photobeams broken), number of movements, and rest time were measured. Each parameter was analyzed separately. At each time interval (or called sample), a two-way analysis of variance (ANOVA) was performed using the ranked data (nonparametric technique) to test for the treatment effect blocked by day. Pairwise comparisons for treated groups to the vehicle control were also performed using Dunnett's t-test.

To evaluate startle reactivity, for the 200 milliseconds immediately succeeding each startle the average force exerted by each startled rat over the entire 200 milliseconds, and the maximum force, were measured. The mean maximum and average voltages (MAXMEAN and AVGMEAN) were computed for each treatment (TREAT) at each trial (TRIALN), and then these values were plotted against trial number for each treatment. The plots are attached to the report. Trials 1-60 were set to time=1, trials 61-120 to time=2, trials 121-180 to time=3 and trials 181-240 to time=4. The mean maximum and average startle responses was computed within each time and for each treatment. The means were then used in the statistical analysis. The startle responses were analyzed using analysis of covariance. Treatment comparisons within time were of interest to the investigators, but not time effects within treatments. Therefore, the startle responses were analyzed by time. The model included terms for the day the rat was tested (date), baseline startle response, and treatment. Date was a blocking factor and baseline startle response was a covariate. There were three separate models for each of the objectives stated above. The varying doses of nepicastat were compared to vehicle using Dunnett's procedure in order to control for multiple comparisons.

When the four nepicastat-treated groups were compared to the vehicle-treated controls, there were no overall no pairwise significant differences at any time examined in any of the 3 parameters.

When compared to the vehicle-treated controls, the clonidine-treated group had significantly more horizontal activities at 2 and 2.5 hours, significantly more movements at 2 hours, and significantly less rest time at 2 hours (all p<0.05). Note that the clonidine-treated group had significantly more rest time than the vehicle-treated controls at 1 hour (p<0.05).

When compared to the vehicle-treated controls, the SKF-102698-treated group had significantly less horizontal activities and significantly less movements at 2.5 hours (both p<0.05). Note that the SKF-102698-treated group had significantly more movements than the vehicle-treated controls at 1.5 and 4 hours (both p<0.05). No significant differences between SKF-102698 and vehicle were detected at any time examined in the rest time.

In general, the horizontal activity and number of movements decreased for the first 2 hours and stayed low for the last 2 hours. Similarly, the rest time increased for the first 2 hours and remained elevated for the last 2 hours.

Nepicastat had no significant effects on the locomotor activity in rats. Animals treated with 3, 10, 30 or 100 mg/kg of nepicastat were not significantly different from the vehicle-treated controls at any time examined in the horizontal activity, no. of movements or rest time.

In startle response, the overall treatment effects for nepicastat and vehicle were not significant (p>0.05) at any time for either response. The overall treatment effect for average startle response at time 2 was marginally significant (p=0.0703), and Dunnett's test revealed that nepicastat 30 mg/kg had a significantly higher average startle response than the vehicle group (p<0.05). Baseline average startle response was statistically significant at times 3 and 4 for both responses (p≤0.05), and marginally significant at times 1 and 2 for maximum startle response, and at time 2 for average startle response (p≤0.10). SKF-102698 (100 mg/kg) was not statistically significantly different from vehicle at any time for either startle response measurement.

Clonidine had statistically significantly lower maximum and average startle responses than vehicle at time 1 (p<0.01) and at time 2 for average startle only (p=0.0352). The maximum startle response at time 2 and the average startle response at time 3 for the clonidine group were marginally significantly lower than the water group.

Nepicastat administered at 3, 10, 30, or 100 mg/kg does not appear to effect the maximum or average startle response in rats at any time when compared to vehicle. SKF-102698 behaved similarly to vehicle (PEG) for both startle responses at all times. Clonidine successfully lowered both maximum and average startle response during earlier times, and behaved similarly to vehicle during later times.

Example 22

The effects of chronic dosing of nepicastat in rats were examined. Between three and thirteen days prior to the first dosing day the rats were placed inside the startle apparatus and after a five minute acclimation period they were presented with a 118 dB noise burst on average once a minute (a variable inter-trial interval ranging between 30 and 90 seconds will be used) for 20 minutes. The startle responses were measured and a mean for the last twenty startle response was calculated for each rat. The rats were randomly placed in one of the eight treatment groups (nepicastat, 5, 15 or 50 mg/kg, bid; SKF-102698, 50 mg/kg, bid; clonidine, 20 µg/kg, bid: d-amphetamine, 2 mg/kg, bid; dH$_2$O or cyclodextrin (SKF-102698's vehicle). Rats were dosed by oral gavage with a 10 ml/kg dosing volume. The rats were dosed in the morning and in the evening every day for ten day. The time in between morning and evening dosing will be between 6 and 10 hours. Previous work has shown that this matching procedure to be the most appropriate for acoustic startle reactivity since there is significant variability in startle response between rats, but a high degree of consistency within rats from one day to the next.

Since it was impossible to test all 96 rats (8 treatment groups, n=12) on the same day, the dosing schedule was staggered such that only 8 rats were run every day. These 12 groups of eight rats each consisted of one rat from each of the eight treatment groups so that the treatment groups were balanced across days. Furthermore, all treatment groups were balanced across the eight motor activity chambers, however, treatment groups could not be balanced across the startle chambers.

The following behavioral tests were administered during and after chronic dosing; body core temperature, motor activity, acoustic startle reactivity, and pre-pulse inhibition of acoustic startle.

The animals were tested in an enclosed room with a white noise generator running Motor activity tests were conducted immediately after the body core temperature reading taken on dosing day ten (about 3 hours and 35 minutes after the morning daily dose of nepicastat, and SKF-102698, and 20 minutes prior to the daily administration of clonidine and d-amphetamine on dosing day ten). Motor activity tests were run for one hour. A diagnostic program was run on each of the motor activity chambers prior to each test session to assure that the photo beams and light sensors were operating properly. Motor activity has been shown to be sensitive to changes in central dopamine levels (Dietze and Kuschinsky, 1994) which makes this behavioral test a potential sensitive assay to the effects of DBH inhibitors in-vivo. D-amphetamine was used as the positive control for this assay.

Rat body core temperatures were obtained by inserting the rectal probe 2 cm into the colon of each rat. Each rat's body core temperature was measured three times and the average of the three reading was calculated. Body core temperature readings were obtained immediately prior to the ten day chronic dosing schedule (to obtain a baseline), and three and half hour after the morning daily dose of nepicastat, and SKF-102698, and 15 minutes prior to the daily administration of clonidine and d-amphetamine, on dosing days one, five and ten. Body core temperature has been shown to be sensitive to both dopamine and norepinephrine levels, which makes this behavioral test a potential sensitive assay to the effects of DBH inhibitors in-vivo. Both clonidine (an alpha$_2$ agonist), and d-amphetamine (a dopamine releaser) were used as the positive controls for this assay.

Acoustic startle reactivity (a series of muscle contractions elicited by an intense burst of noise with a rapid onset), and pre-pulse inhibition (sensorimotor gating measured by analyzing any decrease in startle reactivity which occurs when a startling stimulus is immediately preceded by a non startling stimulus) were both measured in eight SR-Lab (San Diego Instruments, San Diego, Calif.) test stations. The rats were placed individually in a Plexiglas cylinder (10 cm diameter) which was housed in a ventilated sound-attenuating enclosure. Acoustic noise bursts (a broad band noise with a rise time and fall time of 1 msec) were presented via a speaker mounted 30 cm above the animal. Also, these speakers produced a 68 dB level of background noise throughout all test sessions. A piezoelectric accelerometer attached below the plexiglass cylinder transduced the subject's movement into a voltage which was then rectified and digitized (on a scale from 0 to 4095) by a PC computer equipped with SR-Lab software and interface assembly. A decibel meter was used to calibrate the speakers in each of the eight test station to ±1% of the mean. Additionally, a SR-Lab calibrating instrument was used to calibrate each of the eight startle detection apparatuses to ±2% of the mean. Startle reactivity and pre-pulse inhibition tests were run concurrently immediately alter the motor activity test (about 4 hours and 40 minutes after the morning daily injection of nepicastat, and SKF-102698, and 10 minutes after a supplemental administration of clonidine and d-amphetamine on dosing day ten). The startle reactivity and pre-pulse inhibition tests consisted of placing each rat individually into a SR-Lab test station and after a five minute acclimation period the rats were presented with one of three different types of noise bursts (and startle reaction measured) on average once a minute (a variable inter-trial interval ranging between 30 and 90 seconds was used) for an hour (60 total noise bursts and startle reactions). The three different types of noise bursts consisted of a loud noise burst (118 dB), and a relatively quite noise burst (77 dB), the quite burst preceding the loud noise bursts by 100 msec (pre-pulse inhibition trial). These trials were presented in pseudo-random order. Pre-pulse inhibition has been shown to be sensitive to changes in mesolimbic dopamine levels. Furthermore, acoustic startle reactivity has also been shown to be sensitive to changes in dopamine and norepinephrine levels which makes these behavioral test a potential sensitive assay to the effects of DBH inhibitors in vivo. Clonidine and d-amphetamine served as the positive control for the acoustic startle reactivity and pre-pulse inhibition of acoustic startle tests.

The schedule of daily behavioral tests was as follows. At t=0, DBH inhibitor is injected. At 3.5 hours, the core body temperature is measured. At 3 hr. 35 minutes, motor activity is assessed. At 4 hr. 40 minutes, startle reactivity and pre-pulse inhibition are assessed.

Three temperature readings were taken from each subject per time of testing. The avenge of these three readings was then calculated.

Each rats spontaneous locomotion was obtained by calculating the total number of photobeams that the subject broke during the testing session.

The subject's reaction was measured during each trial for the 40 msec window after the stimulus was presented. Each startle reaction was calculated by taking the avenge of 40 readings (one per millisecond) starting immediately after each noise burst. Acoustic startle reactivity was calculated by determining the mean response for each subjects startle elicited by the 118 dB acoustic burst. Pre-pulse inhibition values were calculated by subtracting the mean startle response elicited by the 77 dB pulse-118 dB pulse paired trial (pre-pulse inhibition trial described above) from the 118 dB alone trial and then dividing this value by the 118 db alone trial for each rat, i.e. ([118 dB trial value−pre-pulse inhibition trial value]÷118 db trial value).

An overall one-way ANOVA with a main effect for treatment was performed at each time on the change from baseline for each animal. Subsequent t-tests were performed for each comparison of interest.

Spontaneous motor activity was measured for each animal every 15 min for 1 hour. Each time block (every 15 min) was analyzed separately. Kruskal-Wallis test (nonparametric technique) was performed to test for the difference between treatment groups. If the overall significant difference is not detected, Bonferroni's adjustment for multiple comparisons is then made.

The mean average voltage (AVGMEAN) and mean percent prepulse inhibition (RATIO) were computed for each treatment (TREAT) and trial type (TRIALT) at each trial (TRIALN). Pre-pulse inhibition values were calculated by subtracting the mean startle response elicited by the 77 dB pulse-118 dB pulse paired trial (pre-pulse inhibition trial described above) from the 118 dB alone trial and then dividing this value by the 118 db alone trial for each rat, i.e. ([118 dB trial value−pre-pulse inhibition trial value]÷118 db trial value).

These values were plotted against trial number for each treatment and trial type, and these plots are attached to the report. Note that the y-axis on the plots varies. The trials 1-15 correspond to time 1, 16-30 time 2, 31-45 time 3, and 46-60 time 4. Plots displaying the mean percent prepulse inhibition and the mean average startle of animals over TIME for each treatment are attached also.

The average startle response and the percent prepulse inhibition were analyzed using Analysis of Variance. The model included terms for treatment, animals nested within treatment, time and treatment by time interaction. Treatment effects were tested using the error term for animals nested within treatment. Overall treatment effects and treatment effects by time were studied. The method of Fisher's Least Significant Differences was used to adjust for multiple comparisons. If the overall treatment or treatment by time effects were not significant (p-value>0.05) then a Bonferroni adjustment was made. If the overall treatment effects were nonsignificant, then the adjustment was applied to the specific pairwise comparisons. Further, if the specific pairwise treatment effect was not significant (p-value>0.05), then the adjustment was also applied to the treatment effects within time. If both the overall treatment and treatment by time effects were not significant (p-value>0.05) then a Bonferroni adjustment was made for the individual comparisons within time and averaging over time.

The change from pre-dose in body weights was calculated for each animal for the analysis. A repeated measures two-way ANOVA was used to test for the overall effects of treatment, time and treatment by time interaction. One-way ANOVAS were then performed to test the treatment effect at each day.

The positive controls (d-amphetamine and clonidine) significantly increasing body core temperature on day one of the chronic dosing, but no other compound had any significant effect on body core temperature at any time.

The d-amphetamine group had significantly higher locomotor activity than the vehicle control at all times examined. The clonidine group, however, was not significantly different from the vehicle controls at any time examined. The SKF-102698 50 mg/kg b.i.d. group had significantly lower locomotor activity than its vehicle control at the first 45 minutes (i.e. samples 1-3), but not significant after 45 minutes.

There was no overall significant treatment effect for nepicastat at any time examined. Pairwise comparisons revealed that none of the nepicastat-treated groups were significantly different from the vehicle controls at any time examined. Also, there was no significant difference between the two vehicle controls (dH$_2$O and SKF's vehicle) at any time examined.

None of the treatment groups produced any significant change in pre-pulse inhibition. The overall time effect was statistically significant for the SKF-102698 group and the cyclodextrin group (p=0.0001). The treatment by time interaction was statistically significant for cyclodextrin versus dH$_2$O (p=0.0283), but no others. Treatment effects were not significant for any comparisons of interest. However, the SKF group had marginally higher percent prepulse inhibition compared to the cyclodextrin group (p=0.0782).

During times 1 and 2, the clonidine group had just significantly higher percent prepulse inhibition than the vehicle control and were not significantly different from vehicle during times 3 and 4. Neither d-amphetamine nor SKF-102698 was significantly different from their own vehicle at any time. None of the nepicastat dose groups were significantly different from dH$_2$O at any time.

Only the SKF-102698 treatment group produced a significant change in acoustic startle reactivity. The overall time effect was statistically significant for all comparisons of interest (all p=0.0001). The treatment by time interaction was statistically significant for the comparisons of amphetamine versus dH$_2$O, clonidine versus dH$_2$O and cyclodextrin versus dH$_2$O (all p<0.05), but no others. Treatment effects were significant for SKF-102698 50 mg/kg b.i.d. versus cyclodextrin (p=0.0007) and for nepicastat 50 mg/kg b.i.d. versus SKF-102698 50 mg/kg b.i.d. (p=0.0047), but no others. The SKF-102698 50 mg/kg b.i.d. group had significantly lower startle response compared to cyclodextrin, and also had significantly lower startle response as compared to the nepicastat 50 mg/kg b.i.d. group.

The SKF-102698 (50 mg/kg b.i.d.) group had significantly lower startle response than the cyclodextrin group at all times. During times 1 and 3, the nepicastat (50 mg/kg b.i.d.) group had significantly higher startle response than the SKF-102698 (50 mg/kg b.i.d.) group. No other significant differences were detected.

There was no overall or pairwise significant differences in body weight between groups at the pre-dose baseline.

The d-amphetamine group had a significantly smaller change in body weight from pre-dose than the vehicle controls (p<0.01). When analyzed within each day, the vehicle controls had a significantly greater increase from pre-dose in body weight than the amphetamine group at treatment days 4-10. The clonidine group, however, was not significantly different from the vehicle controls at any time examined. The SKF-102698 (50 mg/kg b.i.d.) group showed a significantly smaller increase (p<0.01) in body weight from pre-dose baseline than its vehicle control (SKF-vehicle). When analyzed within each day, the SKF-vehicle controls had a significantly greater increase from pre-dose in body weight than the SKF-102698 group at treatment days 2-10, except days 3 and 6. Importantly, there was no difference in changes in body weight between the SKF-vehicle and the vehicle control groups on any day.

There was no overall significant treatment effect on body weight for any dose of nepicastat at any time examined. Pairwise comparisons revealed that none of the nepicastat-treated groups were significantly different from the vehicle controls at any time examined. Interestingly, there was a significant (p<0.05) overall difference between the SKF-102698 (50 mg/kg b.i.d.) group and the nepicastat (50 mg/kg b.i.d.) group with respect to changes in body weight. When analyzed within each day, the SKF-102698 (50 mg/kg b.i.d.) group had significantly lower body weights than the nepicastat (50 mg/kg b.i.d.) group at days 7-9.

Example 23

1-methyl-4-phenyl-1,2,3,6-tetrahydropyridine (MPTP) was purchased from RBI, Inc, (Natick, Mass.). For administration, MPTP was suspended in water at a concentration of 2 mg/ml (free base) and was injected subcutaneously in a volume (ml) equal to the weight (kg) of each animal. For example, a 950 gram animal received an injection of 0.95 ml of MPTP at 2 mg/ml resulting in 2.0 mg/kg final per injection.

Monkeys were maintained on a 13 h/11 h light-dark cycle, with food and water available ad libitum. All procedures used in this study followed NIH guidelines and were approved by the Institutional Animal Care and Use Committee (IACUC). Animals were individually housed and allowed a minimum of one month to acclimate to the colony prior to commencing behavioral studies.

Six squirrel monkeys, three non-lesioned and three lesioned (received 2 mg/kg MPTP 3 months prior), were used to study the optimal route of administration of nepicastat. Three different approaches were examined including (i) insertion into treats, (ii) oral syringe, and (ii) oral gavage. Insertion of nepicastat solution (5 mg/ml) into marshmallows was tested in 3 non-lesioned monkeys and proved to be a poor route of drug administration due to failure of animals to ingest treats probably due to adverse taste. Oral syringe injection of nepicastat (0.5, 2, and 5 mg/kg) into the mouth of three non-lesioned and three lesioned monkeys was also not an acceptable route since animals tended to spit out the solution at the highest drug concentration. Oral gavage administration was carried out in 3 MPTP-lesioned monkeys at the highest dose (5 mg/kg) and was well accepted.

Six squirrel monkeys, three non-lesioned and three lesioned (received 2 mg/kg MPTP 3 months prior), were used to study safety and tolerability of nepicastat. Animals received nepicastat at a concentration of 0.5, 2.0, or 5.0 mg/kg twice daily, (10 am and 2 pm), for 5 days with a two-day washout between the different dose levels. Nepicastat was administered via oral syringe at the 0.5, 2.0 and 5.0 mg/kg doses and as oral gavage at the 5.0 mg/kg dose. Drug was well tolerated at the two lower doses. One non-lesioned monkey receiving 5.0 mg/kg had light beige colored loose stools on the final two days of administration that resolved upon one day withdrawal of drug.

Twenty four squirrel monkeys, fourteen females and ten males were used in a Parkinsonian model. The twenty-four animals were randomly assigned to one of four treatment groups, with 6 animals per group. The groups consisted of the following: Group A (6 animals) received placebo (water) treatment; Group B (5 animals) received drug nepicastat at 1 mg/kg/day (0.5 mg/kg twice daily); Group C (6 animals) received 4 mg/kg/day (2 mg/kg twice daily); and Group D (6 animals) received 10 mg/kg/day (5 mg/kg twice daily). In Group B, one animal died acutely following MPTP-lesioning, and was not replaced.

Prior to lesioning, animals were subjected to quantitative assessment of spontaneous motor activity using an infrared activity monitor (IRAM) cage. All recording sessions were 60 minutes in length and were carried out for 10 sessions over a period of 2 weeks. The behavior of animals was also assessed by 1 to 3 clinical raters using a parkinsonian clinical rating scale (CRS) once per day (12 noon to 1 pm) for 3 to 5 consecutive days. Normal animals did not typically score greater than 3 on the CRS. Both the activity monitoring (IRAM) and clinical rating assessments established the mean base-line activity of each animal.

Animals were lesioned by the administration of MPTP at a concentration of 2.0 mg/kg (free-base) via subcutaneous injection to achieve a parkinsonian state. A post-MPTP lesioning behavioral assessment was carried out 2 to 4 weeks after the last MPTP-lesioning. Locomotor activity was monitored by IRAM in 60-minute sessions for 3 to 5 days. Clinical behavior (CAS) was assessed by one to three individuals rating over a period of 3 to 5 days.

In some cases, animals required additional doses of MPTP (2 mg/kg) to obtain a sufficient degree of lesioning to display parkinsonian symptoms, defined as an average total clinical rating score greater than 3. All animals received a final post-MPTP behavioral assessment (IRAM and CRS), within three weeks of starting the efficacy study. This final post-MPTP evaluation was used to establish a baseline clinical parkinsonian state and used as a pretreatment value for statistical analysis.

Animals were tested for response to L-Dopa and the efficacy of drug nepicastat. Testing was carried out 4 to 12 weeks after the last MPTP dose. L-Dopa was administered at a concentration of either 2.5, 5, or 7.5 mg/kg by oral gavage twice daily (at 10 am and 2 pm) for 7 consecutive days. Behavior was determined by IRAM and CRS. Clinical rating was carried out 60 to 90 minutes following the 10 am morning dose on the last 4 days of treatment. Raters (one to three individuals) were blinded to the different treatment groups. IRAM assessment were preformed for 90 minutes immediately following drug administration at 2 pm on the last 2 to 5 days of drug treatment. There was a minimum 2 day washout period between each treatment dose.

Nepicastat or water (as placebo) was administered for 12 days following a minimum 2 day washout after L-Dopa dosing. Drug was administered twice daily at 10 am and 2 pm by oral gavage. Behavior was rated by IRAM and CRS. The CRS was conducted in the morning, 60 to 90 minutes after the 10 am dose of nepicastat on the last 5 days of drug treatment. Raters (one to three individuals) were blinded to the different treatment groups. IRAM assessments were preformed for 90 minutes immediately following drug administration at 2 pm on the last 5 days of drug treatment.

For statistical analysis, locomotor activity and clinical rating scores were monitored. The average locomotor activity was calculated pre- and post-MPTP-lesioning for each animal. The pre-MPTP-lesioning baseline was determined by averaging ten 1-hour monitoring sessions. The post-MPTP (pre-treatment) behavioral assessment was obtained within three weeks of commencing the efficacy study. The post-MPTP-lesioning locomotor activity was determined by averaging three to five 1-hour monitoring sessions (IRAMS). Activity monitoring was reported as "movements/10 minutes". A higher score was considered a faster animal. The Wilcoxon sign rank test was used to compare pre- and post-MPTP-lesioning activity for each group of animals (groups A through D).

IRAM Locomotor activity was monitored every 10 minutes for a minimum of 90 minutes following each drug level. A higher rating is considered a faster (less parkinsonian) animal.

Statistical analysis consisted of descriptive statistics and graphing the mean of each 10 minutes data blocks of placebo and experimental drug at 1, 4, and 10 mg/kg. The graph was then examined to detect any trends. Further statistical analysis was not performed since no difference was determined from graphical analysis.

Statistical analysis comparing post-MPTP lesioning (pretreatment) to 2.5, 5.0, and 7.5 mg/kg L-Dopa and nepicastat (1, 4, 10 mg/kg/day or placebo) was not performed due to insufficient IRAM data collection. Only 60 minutes sessions were collected at Post-MPTP, versus 90 minutes for nepicastat.

In the clinical rating score measurements, no pre-MPTP-lesioned animal scored greater than three on the CRS. A post-MPTP clinical rating score was determined within three weeks of commencing the efficacy study by averaging the total CRS of 1 to 3 individual raters from data over 3 to 5 consecutive days.

Eight parkinsonian features were rated in each animal and the total score was derived from the sum of these eight features. For each animal, a single clinical rating score was obtained for each drug dose by averaging the clinical rating scores of all raters (one to three) conducted over the consecutive multiple dosing (with the same dose) days. This average CRS was used for statistical analysis. A lower score was considered a less parkinsonian behavioral state.

Statistical analysis consisted of: (1) comparisons between the average CRS of placebo to nepicastat at 1, 4, and 10 mg/kg/day using the Kruskal-Wallis (non-parametric analysis of variance). This comparison was repeated using the average CRS for each experimental drug concentration corrected by the final post-MPTP ratings for each animal. The corrected clinical scores are clinical scores of experimental drug at each concentration as a ratio of post-MPTP clinical scores. (2) Pairwise comparisons between the average CRS post-MPTP lesioning (pre-treatment) to 2.5, 5.0, and 7.5 mg/kg L-Dopa and placebo treatment using Friedman's analysis (non-parametric analysis of variance, repeated measures). The same analysis was performed for nepicastat at concentrations of 1, 4, and 10 mg/kg. Dunnett's post hoc analysis for non-parametric data was performed when needed.

IRAM (activity monitoring) and CRS (clinical rating scale) were used to assess the degree of MPTP-lesioning in each squirrel monkey.

There was no significant difference between pre-lesioned and post-lesioned IRAM groups due to the high degree of variability of movements per 10 minutes per animal for Group A: Placebo Treatment. Wilcoxon signed rank test: W=19, N=6, P<0.06 Accept Null Hypothesis. The average CRS for group A was 8.9, range 4.8 to 15.4. All animals showed substantial increase in the clinical rating scores after MPTP-lesioning. Normal animals (non-lesioned) typically have scores less than 3.

There was no significant difference between pre-lesioned and post-lesioned IRAM groups due to the high degree of variability of movements per 10 minutes per animal for Group B: 1 mg/kg/day Treatment. Wilcoxon signed rank test: W=9, N=5, p<0.06 Accept Null Hypothesis Clinical Rating Score (CRS). The average CRS for group B was 10.32, range 4.3 to 16.1. All animals showed substantial increase in the clinical rating scores after MPTP-lesioning. Normal animals (non-lesioned) typically have scores less than 3.

There was no significant difference between pre-lesioned and post-lesioned IRAM groups due to the high degree of variability of movements per 10 minutes per animal for Group C: 4 mg/kg/day Treatment. Wilcoxon signed rank test: W=17, N=6, P>0.06 Accept Null Hypothesis The average CRS for group C was 8.97, range 6.5 to 17.3. All animals showed substantial increase in the clinical rating scores after MPTP-lesioning. Normal animals (non-lesioned) typically have scores less than 3.

There was no significant difference between pre-lesioned and post-lesioned IRAM groups due to the high degree of variability of movements per 10 minutes per animal for Group D: 10 mg/kg/day treatment. Wilcoxon signed rank test: W=21, N=6, P>0.06 Accept Null Hypothesis. All animals showed substantial increase in the clinical rating scores after MPTP-lesioning. The average CRS for group C was 8.02, range 4.0 to 15.6. Normal animals (non-lesioned) typically have scores less than 3.

Overall there was no significant difference in the locomotor activity as measured by IRAM between base-line (pre-MPTP-lesioning) and post-MPTP-lesioning within groups due to the high degree of variability of the RAM results for each animal. The CRS results showed a difference between pre-MPTP and post-MPTP-lesioning states. Pre-MPTP-lesioned animals scored no greater than 3 in the CRS. Post-MPTP-lesioned animals all scored greater than 3. All groups (A through D) had an average CRS ranging from 8 to 10 out of a total possible CRS score of 24.

There were no detectable differences between placebo treatment and three different concentrations of nepicastat (1, 4, 10 mg/kg/day) in the MPTP-lesioned squirrel monkey. Both 4 and 10 mg/kg/day of nepicastat and placebo showed a significant improvement over the post-MPTP (pre-treatment) state. All groups of animals showed significant improvement with both 5 mg/kg and 7.6 mg/kg L-Dopa when compared to post-MPTP (pre-treatment), with the exception of Group C for the 7.5 mg/kg dose and Group B for the 5 mg/kg/dose. No groups of animals demonstrated significant improvement at 2.5 mg/kg L-Dopa when compared to post-MPTP.

A comparison of treatment groups and L-DOPA, Friedman test results, descriptive statistics, and Dunnett's test post hoc analysis was done, and a comparison between the activity monitoring of placebo treatment to all other concentrations of nepicastat at time points 10 to 90 minutes post-dosing. Ten-minute intervals were plotted for each drug dose level. There was no difference of drug (nepicastat) treatment at the 4 and 10 mg/kg/day dose level when compared to placebo. At 1 mg/kg/day animals were slower than placebo treatment. Based on a non-pairwise comparative analysis of 4 different treatment groups (1,4, and 10 mg/kg of nepicastat and placebo), nepicastat produced no significant effect in parkinsonian symptoms compared to placebo (water treatment) in the MPTP-lesioned non-human primate model of PD. Based on a pairwise comparative analysis of animals, (animals of the same group examined pre and post treatment), nepicastat at 4 and 10 mg/kg/day concentrations showed a significant effect in parkinsonian symptoms compared to post-MPTP lesioning, (pre-treatment evaluation). Placebo had a borderline significant effect. Using the same pairwise comparison, 5 and 7.5 mg/kg of L-Dopa demonstrated a significant effect when compared to the post-MPTP lesioned state in all groups with the exception of Group B (no effect at 5 mg/kg L-Dopa) and Group C (no effect at 7.5 mg/kg L-Dopa) animals. However, 2.5 mg/kg of L-Dopa demonstrated no significant effect.

A pharmacokinetic study was carried out to determine the plasma concentration of nepicastat in the squirrel monkey. This study was carried out concurrently with the safety and tolerability study. Three MPTP-lesioned squirrel monkeys (#353, 358 and 374) were used. One milliliter of blood (drawn from the femoral vein of each animal) was collected for analysis. Nepicastat was administered at concentrations of 1, 4, and 10 mg/kg for 5 days with a 2-day washout between each drug concentration. Blood was collected for analysis 1 hour prior to the first dose to establish baseline and at 6 hours after this first drug dose of each of the different drug levels.

A second pharmacokinetic study was carried out to determine the steady-state plasma level of nepicastat. This study was carried out concomitantly with the efficacy study where animals were tested on each of three different drug concentrations for 12 days. One milliliter of blood was drawn from the femoral vein 6 hours after the first dose on day 1, then 6 hours after the first dose on day 7, and finally 6 hours after the first dose on day 12. Baseline plasma levels were determined on samples collected the week prior to drug dosing.

This study also demonstrated that, a pairwise analysis, which reduces animal to animal variability by comparing the same animal pre- and post-treatment, is better suited for detecting a significant drug effect than a non-pairwise study design when a small number of animals is used.

Example 24

Male, spontaneous hypertensive rats (280-345 g; Charles River Labs, Kingston, N.Y.) were fasted overnight then anesthetized with ether. A femoral artery and femoral vein were cannulated with PE50 tubing for recording of blood pressure and administration of compounds, respectively.

Animals were then placed in MAYO restrainers and their feet loosely taped to the restrainer. Heparinized saline (50 units sodium heparin/ml) was used to maintain patency of each cannula throughout the experiment. The following parameters were continuously recorded using Modular Instruments MI$^2$ BioReport™ software installed on an IBM personal computer: mean arterial pressure (MAP), heart rate (HR), and the change from baseline for each parameter at specified time points in the experiment.

All compounds were dissolved on the day of use. Nepicastat was dissolved in deionized water (vehicle) to a free base concentration of 1 mg/ml. Oral dosing volume for nepicastat or vehicle was 10 ml/kg. SCH-23390 was dissolved in saline (vehicle) to a free base concentration of 0.2 mg/ml. Nepicastat or saline were administered intravenously as a bolus in a volume of 1.0 ml/kg followed by 0.2 ml flush of isotonic saline.

Following surgical preparation, each animal was allowed a minimum one hour recovery period. Animals were randomly assigned to four treatment groups: vehicle (iv)/vehicle (po); vehicle (iv)/nepicastat (po); SCH-23390 (iv)/vehicle (po); or SCH-23390 (iv)/nepicastat (po). Once animals were stabilized (minimum one hour), baseline blood pressure and heart rate was determined by taking an average of each parameter over a 15 min period of time. Once baseline blood pressure and heart rate were established, animals were dosed intravenously with either SCH-23390 (200 µg/kg) or vehicle (saline, 1 ml/kg). Fifteen minutes later, animals were orally dosed with either nepicastat (10 mg/kg) or vehicle (deionized water, 10 ml/kg).

Recorded parameters were measured 15 min prior to intravenous dosing to establish baseline blood pressure and heart rate. Recorded parameters were then measured at 5, 10, and 15 min following intravenous administration of SCH-23390 or vehicle. Following oral administration of nepicastat or vehicle, recorded parameters were measured at 15, 30, 60, 90, 120, 150, 180, 210, and 240 min.

At the end of the experiment, each animal was anesthetized with halothane and euthanized via decapitation. The cortex, left ventricle (apex), and mesenteric artery were dissected out, weighed, and fixed in 0.4 M perchloric acid. Tissues were then frozen in liquid nitrogen and stored at −70° C. Biochemical analysis are performed on these tissues at a later date to determine catecholamine levels including dopamine and norepinephrine levels. Blood pressure and heart rate were analyzed separately. The change from baseline for blood pressure and heart rate were analyzed by an analysis of variance (ANOVA) with effects for treatment, time, and their interaction. This analysis was performed both for the post-iv time period and for the post-oral time period. Further analyses were performed at each time by an ANOVA with a main effect for time. Pairwise comparisons were performed following each ANOVA by Fisher's LSD strategy with a Bonferroni correction when the overall treatment effect was not significant.

An additional analysis was performed to compare the baseline means of each treatment group by an ANOVA with a main effect for treatment and subsequent pairwise comparisons. Comparisons of SCH-23390 (iv)/Vehicle (po) vs. Vehicle (iv)/Vehicle (po), Vehicle (iv)/nepicastat (po) vs. Vehicle (iv)/Vehicle (po), and SCH-23390 (iv)/nepicastat (po) vs. Vehicle (iv)/nepicastat (po) were made.

There were no significant differences in baseline heart rate or mean arterial pressure between treatment groups.

Intravenous treatment with SCH-23390 resulted in a significant decrease ($p<0.05$) in heart rate during the post-oral period at 120 min and 240 min compared to vehicle control. Nepicastat did not decrease the heart rate as much as observed in vehicle treated animals. This was statistically significant ($p<0.05$) at 150 and 180 min post dose. The large variability in heart rate observed over the course of this experiment should be noted.

Intravenous administration of SCH-23390 produced a small (5±1 mmHg) yet significant decrease ($p<0.05$) in mean arterial pressure compared to animals that received vehicle during the min post-iv period. Oral treatment with nepicastat caused a significant decrease ($p<0.05$) in mean arterial pressure by 30 min post dose which continued for the duration of the experiment. Pretreatment with SCH-23390 did not significantly attenuate the antihypertensive effects observed with nepicastat administration alone.

Example 25

Male Crl:COBS(WI)BR rats of 15 weeks old were used. Twenty-four rats were chronically implanted with telemetry implants (TA11PA-C40, Data Sciences, Inc., St. Paul, Minn.) for measurement of arterial blood pressure, heart rate and motor activity. The rat was anesthetized with pentobarbital sodium (60 mg/kg, ip) and its abdomen shaved. Under aseptic conditions, an incision was made on midline. The abdominal aorta was exposed, and cannulated with the catheter of a telemetry transmitter unit. After the transmitter was sutured to the abdominal musculature, the skin was closed. Each rat was allowed to recover for at least 2 weeks before being subjected to drug administration. Three days prior to the start of the experiment, the rats were randomly divided into 4 treatment groups: Vehicle (p.o.), Hydralazine (10 mg/kg, p.o.), nepicastat (30 mg/kg, p.o.), nepicastat (100 mg/kg, p.o.).

Systolic blood pressure (SBP), diastolic blood pressure (DBP), mean blood pressure (MBP), heart rate (HR), and motor activity (MA) were monitored. Both nepicastat and hydralazine were prepared in water with traces of Tween 80. All doses were given orally to the rat in 10 ml/kg and were expressed as free base equivalents.

A computerized data collection system was used to continuously collect data on SBP, DBP, MBP, HR, and MA. Data on each rat were collected every 5 min. for 10 sec. These were then averaged hourly and standard errors of the mean (SEM) calculated. All values were expressed as means±SEM. Statistical significance was defined as a p level of less than 0.05. Data on MBP, HR and MA were analyzed separately. Each analysis was done on 26 time points measured each day. A two-way ANOVA with main effects for treatment and time and their interaction was used. If an overall treatment effect or a significant interaction was detected, a series of one-way ANOVA at each time point would be performed. The pairwise comparisons at each time point were performed using Dunn's procedure. If no overall treatment effect was detected, then the pairwise difference from control would be performed by adjusting the critical value using a Bonferroni adjustment.

After the pre-dose values for these parameters were established, respective groups of rats received a 7 day daily treatment of vehicle, nepicastat or hydralazine.

Oral administration of nepicastat at 30 mg/kg (all doses expressed hereafter are po) tended to slowly lower blood pressure but did not induce a consistent hypotensive effect on day 1. As the effect progressed, a peak hypotensive effect of −10 mmHg was observed on day 2 at hour 13. Similar degrees of antihypertensive effects were induced throughout the study. At 100 mg/kg, the compound induced a peak antihypertensive response of −11 mmHg 22 hr after dosing on day 1 (p<0.01). MBP continued to decrease and reached its nadir of approximately −17 mmHg on day 3 (p<0.01). The MBP remained low throughout the study.

Hydralazine at 10 mg/kg caused an immediate hypotensive effect which subsided in 10 hr, and a maximal decrease of −24 mmHg (p<0.01) in MBP was observed within 1 hr after dosing on day 1. Similar transient hypotensive effects were observed throughout the study.

Nepicastat at 30 and 100 mg/kg, did not consistently affect HR on day 1. On day 2, however, Nepicastat at 100 mg/kg caused a bradycardic response of −100 b/mm 3 hours after dosing. Significant but less pronounced bradycardic responses were observed on days 3-7. In comparison, hydralazine at 10 mg/kg induced varying degrees of tachycardia throughout the study.

Throughout the study, none of the drug treatments showed a consistent effect on MA.

Body weights were recorded daily. For body weight, a two-way ANOVA with respect to the changes from pre-dose was used to analyze overall effects for treatment, day, and treatment by day interaction. Then a one-way ANOVA was performed for each day, and pairwise comparisons for the drug-treated groups to the vehicle controls were made using Dunn's procedure and Fisher's LSD strategy to adjust for multiple comparisons. Compared to that treated with vehicle, none of the drug treatments had any effect on body weights (p<0.05). Although treatment with nepicastat at 100 mg/kg tended to decrease body weight on day 3, it was not statistically significant.

Example 26

Nepicastat reduces the conversion of dopamine to norepinephrine. Basic tests for nepicastat activity measure the levels of plasma or urinary dopamine or the ratio of dopamine to norepinephrine. Nepicastat treatment can increase plasma or urinary levels of dopamine or increase the dopamine/norepinephrine ratio in plasma or urine.

Shown in FIG. 5, are the levels in urinary dopamine levels in normal volunteers after 24 hour treatment with nepicastat.

Using the repeated-measures analysis of variance model, a significant increase in the mean supine plasma dopamine/norepinephrine ration was detected in subjects receiving 200 mg of nepicastat when compared to those receiving placebo (p<0.05). Urinary dopamine levels increased after 10 days of dosing with both 40 mg and 200 mg of nepicastat.

Example 27

In patients with chronic heart failure (CHF), daily doses of 40, 80, and 120 mg of nepicastat administered for 10 days were generally well tolerated. The dose at which the frequency of significant adverse events increased was 160 mg.

Four of 8 patients treated with 160 mg for 8 days or longer developed a rash. Two of the rashes were accompanied by pruritus. One patient also had shortness of breath with the rash.

One patient treated with the 80 mg dose was withdrawn from the study because of symptomatic orthostatic hypotension. Concomitant medications included hydralazine and three diuretics. Occasional cases of orthostatic hypotension were reported in patients on all doses, including placebo. Symptomatic orthostatic hypotension was reported in 6 of the 8 patients who received 160 mg In an ongoing study in patients with CHF, there have been 2 deaths: one death was due to worsening CHF (patient was receiving 80 mg qd) and one was sudden death in a patient who was receiving placebo.

One serious adverse event reported as possibly being related to drug was an increasing creatinine level, which required hospitalization. Medically significant events not considered related to study drug include: worsening CHF in 2 patients (one of whom subsequently had an acute MI and cardiac arrest), unstable angina in 1 patient, atypical chest pain in 1 patient, and an adrenal mass in 1 patient who had a history of breast cancer.

In studies of congestive heart failure patients, changes in plasma dopamine levels, norepinephrine levels, and dopamine/norepinephrine ratios after treatment with nepicastat in a 10 day study were determined. Nepicastat treatment increased dopamine/norepinephrine levels in the 10 day study.

In studies of congestive heart failure patients, plasma dopamine levels, norepinephrine levels, and dopamine/norepinephrine ratios and changes of the levels and the ratios after treatment with nepicastat in a 30 day study were determined. As Nepicastat treatment increased dopamine/norepinephrine levels in the 30 day study.

Example 28

Dopamine/norepinephrine ratios in the brain of rodents treated with nepicastat were determined. Dopamine/norepinephrine ratios increased in the brains of rodents treated with nepicastat or disulfuram.

It will be readily apparent to one of ordinary skill in the relevant arts that other suitable modifications and adaptations to the methods and applications described herein are suitable and may be made without departing from the scope of the invention or any embodiments thereof. While the invention has been described in connection with certain embodiments, it is intended to cover such alternatives, modifications, and equivalents as may be included within the spirit and scope of the invention as defined by the following claims.

Example 29

The delayed-matching-to-position (DMTP) test is used to examine the potential effects of drugs on short-term or working memory in rats.

Prior to the commencement of testing nepicastat in the delayed matching to position study, pilot studies were performed with the aims of assessing the behavioural/physiological effects of both acute and repeated administration of the highest proposed dose of nepicastat (100 mg/kg p.o.) and establishing the maximum tolerated oral dose of physostigmine administered repeatedly.

In pilot studies, nepicastat (30 and 100 mg/kg p.o.) or vehicle was administered acutely to male Sprague-Dawley rats (n=8) within the same weight range as the trained animals (400-480 g). The animals were observed by an observer blind to the treatment status of each animal at 1, 3 and 24 h following drug or vehicle administration. Similarly, in a separate study, physostigmine (1, 3, 10 or 30 mg/kg p.o.) or vehicle were administered acutely to groups of 8 rats. Observations were made at 1, 3 and 24 hr after drug or vehicle administration.

In pilot studies of repeated administration, nepicastat (100 mg/kg p.o.) or vehicle was administered twice daily (06:00 and 18:00 h) for 10 days (once on day 11) to groups of 8 rats. The weights of the animals were monitored throughout the study and, on day 5, the animals were observed 'blind' by an independent observer in order to assess any overt behavioural/physiological effects following repeated administration. In a separate study, groups of 8 rats received vehicle or physostigmine (0.3, 1, 3 or 10 mg/kg p.o.) using the same dosing schedule. The weights of the animals were monitored throughout the study.

Nepicastat (30 or 100 mg/kg p.o. acutely) did not induce any overt behavioural/physiological changes. Similarly, there were no overt effects of repeated administration of nepicastat at a dose of 100 mg/kg p.o. However, in the latter study the drug-treated animals displayed a mean loss in body weight of 28 g after 11 days whereas controls had a mean increase in body weight of 1 g. Drug treated animals also became more irritable than controls when handled during the 11 day study.

Acute administration of physostigmine at doses of 3 mg/kg or higher induced overt behavioural effects (chewing mouth movements and salivation). Signs of toxicity were observed at 30 mg/kg p.o. (cyanosis, tremor, head jerks, ataxia). Repeated administration of 3 and 10 mg/kg p.o. physostigmine was toxic (3 of 8 animals were found dead on day 2 in the 10 mg/kg group, and 2 of 8 animals convulsed on day 5 in the 3 mg/kg group). There were no effects of repeated administration of 0.3 or 1 mg/kg physostigmine.

As a result of these studies the highest dose of nepicastat for the DMTP study was reduced to 30 mg/kg p.o. and a dose of 1 mg/kg p.o. of physostigmine was chosen for repeated administration.

In the present DMTP study, rats were trained to remember the position of a lever across a scheduled delay of either 0, 8, 16 or 32 s in order to earn food reward. Following training, the effects of repeated administration of nepicastat (1, 3, 10 and 30 mg/kg p.o. b.i.d.) or physostigmine (1.0 mg/kg p.o., b.i.d.) were examined across 10 successive days of testing in the DMTP task. On the eleventh day of the experiment, the animals that were treated with nepicastat and physostigmine were co-administered scopolamine Hbr (0.1 mg/kg, s.c., 30 mm pretreatment time). The dose of scopolamine was selected on the basis of data from a pilot DMTP study in which 0.1 mg/kg of scopolamine was found to induce a significant impairment in choice accuracy. In addition to the animals treated with either nepicastat or physostigmine, one group of animals which had previously been treated with vehicle, was treated with scopolamine. Another group of rats received only vehicle treatment throughout the experiment. The purpose of the final scopolamine test was to determine whether chronic administration of nepicastat or physostigmine would reverse a scopolamine induced impairment in choice accuracy in the DMTP task.

The dependent measures in the present study included percentage of correct choices, the latency to make choice responses and the number of trials which the animals were able to complete during the 70 min test sessions. Changes in the former measure may indicate changes in memory and/or attentional function whereas changes in the latter two measures may be indicative of other non-cognitive effects of the drugs.

Fifty-six male Sprague Dawley rats, weighing between 200-290 g at the beginning of training, were used. They were housed in groups of four per cage and were each fed approximately 12-15 g of food per rat per day. This amount of food maintained the rats at approximately 85% of their free-feeding weight. Any animals which began to drop below this weight were given additional food. Water was freely available. The animals were maintained on a 12:12 hour light/dark cycle with the light period beginning at 6 a.m.

Twelve Campden Instruments operant chambers with two retractable levers and a centrally located food magazine were used for behavioural testing. A flap, which could be pushed back by the rat to enable it to obtain food pellets, was positioned in front of the food magazine. The boxes were modified so that partitions could be fitted either side of the food magazine. The partitions were clear Perspex, reaching from the grid floor to the ceiling of the chamber and extending 105 mm into the central area. The operant boxes were contained in sound and light attenuating shells. Paul Fray Control System Interlaces and an Acorn A5000 computer programmed with Arachnid software was used to control the operant equipment.

With the house light on throughout the session, rats were initially trained to retrieve Noyes 45 mg Formula 'A' food pellets from behind the magazine flap. Rats were then trained to press both the left and right levers to obtain food reward. Either the left or right lever was randomly presented during a 30 mm session. A response to the inserted lever resulted in the retraction of the lever, delivery of a food pellet and illumination of the magazine light. The magazine light remained on until the pellet was retrieved.

Matching to position training began next. This and all subsequent training was conducted with the partitions fitted into the operant boxes. The sessions were initially 50 minutes long. Rats were placed in the operant box and the session began when the houselight was illuminated. Following a 30 s intertrial interval (ITI), one of the two levers (the sample lever) was inserted into the chamber. The lever remained inserted into the chamber until a lever-press response occurred. A response to the lever resulted in retraction of the lever and the illumination of the magazine light (but not pellet delivery). As soon as the magazine flap was pressed the magazine light was extinguished and both levers were inserted. A response to the sample lever (i.e., the same lever as was previously presented) resulted in retraction of both levers, delivery of a food pellet and the illumination of the magazine light. The magazine light remained on until the flap was pressed. A response to the incorrect lever (the opposite lever to that presented as the sample lever) did not produce a food pellet and initiated a 10 s time-out (TO) period during which the houselight was extinguished. A 30 s ITI was initiated before the commencement of a new trial. The lever inserted as the sample lever was semi-randomly determined such that the right and lefthand levers were presented as the sample lever 8 times in a block of 16 trials.

A correction procedure was used throughout this and all subsequent training. The lever to be inserted (left or right) as the sample lever was randomly determined by the computer on non-correction trials (i.e., the first trial of the session and trials that immediately followed a trial on which a correct choice occurred). Each time an incorrect response occurred, the lever that was not chosen (i.e., the 'correct' lever) was presented as the sample on the subsequent 'correction' trial. These correction trials prevented position habits (i.e., always responding on either the left or right lever and achieving 50% correct). The number of correction trials was recorded, but only the data collected on the non-correction trials were used to evaluate the percentage of correct choices.

Following 24 sessions, the animals were performing the matching to position task with a high degree of accuracy. On Session 25 a variable delay interval was interposed between the depression of the sample lever and presentation of the levers on the choice trial. After a response to the sample lever, the choice levers were inserted following the first flap press occurring after either a 0 s (immediate), 4, 8 or 16 s delay. The order of the four types of trials (0, 4, 8 or 16 s delay) was semi-randomly determined with the constraint that in a 16 trial block, each delay occurred 4 times; twice on a left trial and twice on a right trial. A limited hold was used such that if the rat did not make a choice response within 30 s of the end of the scheduled delay period, the trial was terminated and the intertrial interval began. Such a trial was counted as incomplete and did not contribute to the data analysis. The same trial was reinstated following the end of the ITI. From Session 25 onward the time-out period following incorrect choices was omitted and the session length was increased to 70 minutes.

Following 26 sessions with the 0-16 s delay (Session 25-50) the intertrial-interval was decreased to 10 s and, over the next 8 sessions (Session 51-58), a delay of up to 64 s was used. Due to poor performance at the 64 s delay, however, this delay was not used in any further sessions. On Session 59, delays of 0, 8, 16 and 32 s were used. These delays were used in all subsequent sessions. Only 51 of the 56 rats completed more than 24 trials (correction plus non-correction) during Session 59. These rats were selected and semi-randomly assigned to the following 7 groups such that the groups were matched on performance (percent correct, response latency and number of trials completed): Vehicle/Vehicle (n=7), Vehicle/Scopolamine (n=), nepicastat 1.0 mg/kg/Scopolamine (n=7), nepicastat 3.0 mg/kg/Scopolamine (n=7), nepicastat 10.0 mg/kg/Scopolamine (n=7), nepicastat 30 mg/kg/Scopolamine, and Phys/Scopolamine (n=8).

At 6:00 am and 6:00 pm of the consecutive days during which Sessions 60-69 were run, the rats received oral administration of either vehicle, physostigmine (Phys) or nepicastat (1, 3, 10 or 30 mg/kg). Due to the high degree of choice accuracy displayed by the vehicle treated animals during sessions 68 and 69, the 0, 8, 16 and 32 s delay was also used during the final test session (Session 70) in which all but the Vehicle/Vehicle treated group received 0.1 mg/kg of scopolamine HBr administered s.c. 30 minutes prior to testing. The animals in the Vehicle/Vehicle group received a s.c. injection of saline 30 minutes prior to the final test session. Thus, the drug treatments administered to the seven groups during the 11 consecutive days of the present experiment were:

| Group | Session 60-69 (0, 8, 16, and 32 s delay) | Session 70 (0, 4, 8, and 32 s delay) |
| --- | --- | --- |
| 1 | Vehicle | Vehicle/Vehicle |
| 2 | Vehicle | Vehicle/Scopolamine |
| 3 | nepicastat 1.0 mg/kg | nepicastat 1.0 mg/kg/Scopolamine |
| 4 | nepicastat 3.0 mg/kg | nepicastat 3.0 mg/kg/Scopolamine |
| 5 | nepicastat 10 mg/kg | nepicastat 10 mg/kg/Scopolamine |
| 6 | nepicastat 30 mg/kg | nepicastat 30 mg/kg/Scopolamine |
| 7 | Physostigmine | Physostigmine/Scopolamine |

The data collected and analyzed in the present DMTP study include 1) the percentage of correct responses; 2) the latency between performance of a response to the sample lever and the performance of the choice response and 3) the total number of correction and non-correction trials completed. The former two dependent measures were collected for the non-correction trials only.

In order to increase the power and sensitivity of the statistical analyses, during the first 10 drug treatment sessions (Session 60-69) the data were collapsed into two-session blocks (Block 1-5), although figures for the data collected on Day 1-Day 10 of the study are included. Also, because the animals in the Vehicle/Vehicle and the Vehicle/Scopolamine groups received the same treatment for the first 10 days of testing, the animals in these two groups were combined for the purpose of statistical analysis during Blocks 1-5.

Two-way analysis of variance (ANOVA) with drug treatment as the between-subjects factor and delay (0, 8, 16 or 32 s) as the within-subjects factor was used to analyze percentage of correct choices and response latency. These analyses were conducted separately for each block of data. Significant interactions were followed by a one-way ANOVA which was conducted at each delay. A significant main effect from a one-way ANOVA was followed by a two-tailed Dunnett's t-test. One-way ANOVA followed by a post hoc Dunnett's test, when appropriate, was used to analyze the mean number of trials completed.

All the statistical tests were conducted on a Macintosh computer using SuperAnova software. Alpha was set to 0.05 throughout. Animals which were unable to complete trials at each of the four delay periods were excluded from analyses of percentage of correct choices and response latency. The number of animals that were included in the analysis of percentage of correct choices and latency to respond for each of the 5 blocks of drug testing and on the scopolamine (scop) test day were recorded. To assess the overall effects of the drugs on ability to perform the delayed matching to sample task, all animals were included in the analysis of number of trials completed.

Physostigmine sulphate (1.0 mg/kg, supplied by RBI) and nepicastat (1, 3, 10 and 30 mg/kg, supplied by Roche) were administered p.o. twice daily starting at 6:00 am and 6:00 pm. Scopolamine HBr (0.1 mg/kg, supplied by Sigma) was administered s.c. 30 minutes prior to the last test session. Physostigmine and nepicastat were dissolved or suspended in distilled water and injected in a volume of 2.5 ml/kg. Scopolamine HBr was dissolved in saline and injected in a volume of 1.0 ml/kg. All drug doses are expressed as base weight.

During the first block of testing, the drugs had no significant effects on percentage of correct choices or the latency to perform a choice response in the DMTP task. Drug treatment also failed to affect the number of trials completed, $F(5,45)=0.319$, $p=0.899$.

In block 2, nepicastat and physostigmine had no significant effects on any of the dependent measures during this block of the test. Although the effect was not statistically significant, $F(5,45)=1.717$, $p=0.150$, there was a trend towards a decrease in the number of trials completed. This apparent effect was slightly more marked in the groups treated with either 3 or 30 mg/kg of nepicastat, and in the group treated with physostigmine. In fact, during this block of training only 4 out of 7 of the animals treated with 30.0 mg/kg of nepicastat were able to complete trials at all of the four delays.

During block 3 of testing the animals treated with physostigmine displayed a delay-independent impairment in choice accuracy. ANOVA on percentage of correct choices revealed a significant main effect of drug treatment, but the drug treatment X delay interaction failed to reach statistical significance. A post hoc Dunnett's test on the main effect of drug treatment revealed that only the physostigmine treated group significantly differed from the vehicle treated group. Drug treatment did not significantly affect response latency or number of trials completed, $F(5,45)=0.701$, $p=0.625$, during this block of testing.

The effects of drug treatment on percentage of correct choices approached, but failed to reach statistical significance in block 4 ($p=0.056$). Drug treatment did, however, significantly impair response latency with the ANOVA revealing a significant drug treatment X delay interaction. Subsequent one-way ANOVAs conducted at the 0, 8, 16 and 32 s delays found a statistically significant group effect at only the 32 s delay; $F(5,40)=2.115$, $p=0.084$; $F(5,40)=1.403$, $p=0.244$; $F(5,40)=2.259$, $p=0.067$; $F(5,40)=3.325$, $p=0.013$, for the 0, 8, 16 and 32 s delays, respectively. A post hoc Dunnett's test at the 32 s delay found that only the group treated with 10.0 mg/kg of nepicastat had a longer latency to perform the choice response than did the vehicle treated group. Drug treatment did not significantly affect the number of trials completed during Block 4 of the test, $F(5,45)=1.533$, $p=0.199$.

During block 5 of testing nepicastat induced a marked dose- and delay-dependent impairment in choice accuracy. Two-way ANOVA revealed a significant drug treatment X delay interaction and subsequent one-way ANOVAs at the 0, 8, 16 and 32 s delays found a significant group difference in percentage of correct choices at only the 32 s delay, $F(5,39)=0.327$, $p=0.894$; $F(5,39)=0.825$, $p=0.539$; $F(5,39)=1.188$, $p=0.333$; $F(5,39)=3.018$, $p=0.021$, for the 0, 8, 16 and 32 s delays, respectively. A post hoc Dunnett's test conducted at the 32 s delay found that both the 10 and the 30 mg/kg nepicastat treated groups showed impairments in percentage of correct choices relative to the vehicle treated animals.

Nepicastat and physostigmine did not significantly affect response latency or number of trials completed, $F(5,45)=1.692$, $p=0.156$, during Block 5 of the test.

Many of the animals did not perform the delayed matching to sample test after administration of scopolamine HBr. Only 1 rat treated with 10.0 mg/kg of nepicastat plus scopolamine, and only 2 rats treated with 30.0 mg/kg of nepicastat plus scopolamine were able to complete trials at each of the four delays. In fact n<4 occurred in all the groups except for the Vehicle/Vehicle and the Vehicle/Scopolamine in which seven and four rats, respectively, completed trials at each of the four delays.

The number of trials completed by the animals in all of the scopolamine treated groups was significantly reduced, $F(6,16)=8.801$, $p=0.001$.

Due to the small number of subjects in the scopolamine treated groups, the choice accuracy and the response latency data were not subjected to ANOVA. In addition, the mean percentage of correct choices collapsed across the four delays. A t-test comparing the choice accuracy in the Vehicle/Scopolamine group to the Vehicle/Vehicle group found that scopolamine significantly impaired percentage of correct choices, $t_{(9)}=4.15$, $p=0.003$. With fewer than 4 subjects in the other groups, further statistical analyses were not conducted. It is interesting to note, however, that the two animals in the group given 30.0 mg/kg of nepicastat plus scopolamine performed well compared to the group treated with scopolamine alone: both of the animals treated with 30.0 mg/kg of nepicastat plus scopolamine made more correct choices than any of the animals in the Vehicle/Scopolamine treated group or any of the animals in the other scopolamine treated groups.

Nepicastat when administered alone does not appear to induce memory enhancing effects in the DMTP test. It is notable that the delay induced memory impairment observed in the vehicle treated control animals appeared to dissipate across the five blocks of testing. However, by the fifth block of testing the vehicle treated control animals were still showing a delay-dependent memory impairment with 100% choice accuracy at the 0 s delay and 80% choice accuracy at the 32 s delay. Thus, a ceiling effect in the performance of the vehicle treated animals at the 32 s delay was not observed.

Notably, by the fifth block of training nepicastat may have selective memory disrupting effects. Physostigmine did not improve performance on any of the treatment days and actually produced a delay-independent impairment in choice accuracy during Block 3 of testing (Days 5 & 6). The results from a scopolamine challenge test on day 11 in which the animals were co-administered scopolamine HBr (0.1 mg/kg) and nepicastat or physostigmine could not be analyzed due to the small number of subjects in the nepicastat and physostigmine treated groups that were able to perform the DMTP task. However, two rats receiving 30.0 mg/kg of nepicastat and scopolamine that were able to perform the DMTP task displayed a higher choice accuracy than any of the other scopolamine treated animals. It is possible that nepicastat is capable of reversing some of the cognitive disruption induced by scopolamine, an effect that may be masked by other "non-cognitive" actions of the compound.

Nepicastat induced significant dose- and delay-dependent impairments in choice accuracy. The animals treated with 10.0 mg/kg of nepicastat showed absolutely no impairments in choice accuracy at the 0, 8 and 16 s delays. In contrast, at the 32 s delay, the animals in the 10.0 mg/kg nepicastat group were impaired relative to the vehicle treated group. The group treated with the highest dose of 30.0 mg/kg of nepicastat showed no impairments in choice accuracy at the 0 s delay, a tendency to impaired choice accuracy at the 8 and 16 s delays and a significant impairment in choice accuracy relative to the vehicle treated groups at the 32 s delay. The delay-dependent nature of these drug-induced impairments in choice accuracy suggests that the compound may be acting directly on short-term or working memory. The animals are sufficiently motivated and able to accurately perform the DMTP task at the shorter delays and show impairments only when the retention interval is long. Few compounds that have been tested in this model have shown this profile. Many compounds which have been claimed to impair memory typically induce impairments in choice accuracy which is observed at all delays (e.g., MK-801, scopolamine). Nepicastat had a small effect on latency to complete trials which was apparent on the fourth block of training, during which the animals treated with 10.0 mg/kg of nepicastat took longer to completed the 32 s delay trials than the vehicle treated animals. This effect was not dose-dependent and was not observed in the group treated with 30.0 mg/kg. There was also a trend for the animals treated with nepicastat to complete fewer trials than the vehicle treated animals: trends for reductions in number of trials completed were observed during the last two blocks of training. Due to the variability in the data, however, these trends did not reach statistical significance. This variability in the data was unexpected. It appears likely that the initial stress induced by the chronic oral dosing regime may have disrupted the performance of these food-deprived animals, particularly during the first few blocks of the experiment. All of the groups showed reductions in the number of trials completed between the first and second block of training. The animals recovered from this initial decline and showed more consistent performance across the next three blocks of training.

We found that some of the animals in this study began to lose weight, in some cases in excess of 5% of total body weight. Animals which were showing weight loss were separated and given additional food at the end of their daily training session. This extra feeding may have contributed to the variability in number of trials completed. Although systematic recordings were not made, casual observation suggested that more animals in the mg/kg group than in the other groups had to be given additional food. This observation is consistent with the results of a pilot study in which daily administration of 100 mg/kg p.o. of nepicastat induced a marked loss of body weight.

Physostigmine did not improve performance of the rats in the DMTP test. In fact, the animals treated with physostigmine showed a significant impairment in percentage of correct choices during Block 3 of training. In contrast to the effects obtained with nepicastat, the impairment in choice accuracy induced by physostigmine was delay-independent: the interaction term from the analysis of variance did not approach statistical significance. Thus, the effects of physostigmine on response accuracy are likely to be secondary to behaviorally toxic effects of the drug when it is administered at this dose. The animals appeared to develop tolerance to these effects over the last two blocks of training during which the impairments in choice accuracy induced by physostigmine no longer reached statistical significance.

Finally, physostigmine did not appear to reverse the effects of scopolamine during the scopolamine test. It is possible that a different dose of physostigmine may have been effective against scopolamine. We have not previously attempted to reverse scopolamine with physostigmine using the present dosing regime and therefore have no historical data to compare with the present results. This lack of effect of physostigmine may be due to the fact that, compared with acute administration, a lower dose of physostigmine had to be employed for chronic administration. The animals would not have tolerated repeated administration of a higher dose of physostigmine (see results of the pilot study) which may be required to reverse the effects of scopolamine. In addition, nepicastat did not appear to reverse the effects of scopolamine although it is interesting that the two animals treated with 30.0 mg/kg of nepicastat that were able to perform during the scopolamine test showed higher choice accuracy than any of the animals in any of the other scopolamine treated groups. Further research would be needed to determine unequivocally whether acute or chronic treatment with nepicastat can reverse the effects of scopolamine in this test.

Nepicastat appears to have specific memory-disrupting effects which are apparent after 8 days of dosing. Physostigmine did not improve performance on any of the treatment days and actually produced a delay-independent impairment in choice accuracy during Block 3 of testing (Days 5 & 6). The results from a scopolamine challenge test on day 11 in which the animals were co-administered scopolamine HBr (0.1 mg/kg) and nepicastat or physostigmine could not be analyzed due to the small number of subjects in the nepicastat and physostigmine treated groups that were able to perform the DMTP task. However, two rats receiving 30.0 mg/kg of nepicastat and scopolamine that were able to perform the DMTP task displayed a higher choice accuracy than any of the other scopolamine treated animals. It is possible that nepicastat is capable of reversing some of the cognitive disruption induced by scopolamine, an effect that may be masked by other "non-cognitive" actions of the compound. On the final block of training, nepicastat induced dose- and delay-dependent impairments in choice accuracy. This is an unexpected finding given that many other memory disrupting drugs, such as scopolamine and MK-801, induce delay-independent impairments in choice accuracy that are probably due to impairments in attention and/or motor/motivational factors. In contrast, it is unlikely, that changes in attention or motor/motivation performance could account for the present results with nepicastat. If this drug is selective for a novel receptor or pharmacological mechanism, these results suggest an important role for this substrate in working memory.

Example 30

Recently we have demonstrated that nepicastat, a selective dopamine β-hydroxylase inhibitor, exhibited an effective antihypertensive activity in acute studies in SHRs. The antihypertensive effects of nepicastat were examined chronically in the same strain of rats. Furthermore, we also explored the possible potentiation effects of the co-administration of the compound with the angiotensin converting enzyme inhibitor enalapril. Effects of the treatments on the cardiac hypertrophy in SHRs were also examined.

Male SHRs/NCr1 BR rats (22-28 weeks old at the onset of dosing), and weight matched WKY/NCrI BR rats were used. Four series of experiments were conducted sequentially:

| Series I | |
|---|---|
| Vehicle | |
| Enalapril | 10 mg/kg |
| nepicastat | 3 mg/kg |
| nepicastat | 10 mg/kg |
| Series II | |
| Vehicle | |
| Enalapril | 10 mg/kg |
| nepicastat | 30 mg/kg |
| nepicastat | 100 mg/kg |
| Series III | |
| Vehicle | |
| Enalapril | 1 mg/kg |
| nepicastat | 30 mg/kg |
| nepicastat | 30 mg/kg + enalapril 1 mg/kg |
| Series IV | |
| Enalapril | 1 mg/kg (E1) |
| nepicastat | 15 mg/kg + E1 |
| nepicastat | 30 mg/kg + E1 |
| nepicastat | 60 mg/kg + E1 |

In each series, 24 SHRs were chronically implanted with telemetry implants for measurement of arterial blood pressure, heart rate and motor activity. The rat was anesthetized with pentobarbital sodium (60 mg/kg, i.p.) and its abdomen shaved. Under aseptic conditions, an incision was made on midline. The abdominal aorta was exposed, and cannulated with the catheter of a telemetry transmitter unit. After the transmitter was sutured to the abdominal musculature, the skin was closed. Each rat was allowed to recover for at least 2 weeks before being subjected to drug administration. The rats were housed individually in a quiet room with reversed light/dark cycle (08:00-20:00, lights off.)

Three days prior to the start of the experiment, the rats were randomly divided into 4 groups and their systolic blood pressure (SBP), diastolic blood pressure (DBP), mean blood pressure (MBP), heart rate (HR), and motor activity (MA) were monitored. After the predose values for these parameters were established, respective groups of rats received a 30 day daily treatment of nepicastat and/or enalapril (see below).

Twenty-four hrs after the last treatment, the rats were sacrificed and the left ventricles were collected, weighted (wet weight), and lyophilized for at least 24 hr to obtain dry weights.

At the start of each experiment, the number of rats in each group undergoing telemetry monitoring was always 6. In Series I, however, 7 Wistar Kyoto (WKY) rats were similarly housed and dosed with vehicle (water), while in Series III and IV an additional 2 rats in each group were similarly treated (to increase the numbers of animals for statistical analysis on effects on the hypertrophy of SHRs). No telemetry instrumentation or monitoring was conducted on these rats.

Both nepicastat and enalapril were prepared in water. All doses were given orally to the rat in 10 ml/kg and were expressed as free base equivalents. Enalapril (Vasotec®) was obtained commercially from a local pharmacy.

A computerized data collection system was used to continuously collect data on SBP, DBP, MBP, HR, and MA. Data on each rat were collected every 5 min. for 10 sec. These were then averaged hourly and standard errors of the mean (SEM) calculated. At the end of the treatment, left ventricular mass (dry and wet weights) were obtained. Body weights were recorded daily.

All values were expressed as means±SEM. Statistical significance was defined as a p level of less than 0.05.

Data on MBP, HR and MA were analyzed separately. Each analysis was done on 26 time points measured each thy. A two-way ANOVA with main effects for treatment and time and their interaction was used. If an overall treatment effect or a significant interaction was detected, a series of one-way ANOVA at each time point would be performed. The pairwise comparisons at each time point were performed using Dunn's procedure. If no overall treatment effect was detected, then the pairwise difference from control would be performed by adjusting the critical value using a Bonferroni adjustment.

For left ventricular mass, an analysis of covariance with a covariate of final body weights was used to analyze tissue wet weights and tissue dry weights, while Kruskal-Wallis test was used to analyze ratios of tissue wet weight/body weight and tissue dry weight/body weights. If an overall treatment effect among all groups was not detected, Bonferron's adjustment to multiple comparisons was then made.

For body weight a two-way ANOVA with respect to the changes from pre-dose was used to analyze overall effects for treatment, day, and treatment by day interaction. Then a one-way ANOVA was performed for each day, and pairwise comparisons for the drug-treated groups to the vehicle controls were made using Dunn's procedure and Fisher's LSD strategy to adjust for multiple comparisons.

For series I and II, Oral administration of nepicastat at 3 and 10 mg/kg (all doses expressed hereafter are po) did not significantly affect blood pressure on any of the 30 day treatment (data not shown). At 30 mg/kg, nepicastat gradually lowered MBP on day 1 and continued to lower the MBP to a maximal of −20 mmHg on day 3 ($p<0.01$), with little recovery within 24 hr. Similar antihypertensive effects were induced throughout the study. At 100 mg/kg, the compound induced a peak antihypertensive response of −29 mmHg 21 hr after dosing on day 1 ($p<0.01$). MBP continued to decrease and reached its nadir of approximately −42 mmHg on day 3 ($p<0.01$). The MBP remained low throughout the study.

Enalapril at 10 mg/kg, consistently lowered MBP throughout the study. A maximal decrease of −29 mmHg ($p<0.01$) in MBP was observed within 1 hr after dosing on day 5.

In series III, although mono-administration of enalapril at 1 mg/kg (n=6) or nepicastat at 30 mg/kg (n=6) induced only a small antihypertensive effect, the co-administration of the two compounds (n=6) induced a greater antihypertensive response (−21 mmHg at hr 16 on day 1, $p<0.01$). The onset of the response was slow and gradual. With a second administration on day 2, a greater antihypertensive response was observed most of the day with combined treatment (−25 mmHg at hr 13, $p<0.01$). The potentiation was observed throughout the study.

In series IV, potentiation of the effects of nepicastat by a non-antihypertensive dose of enalapril was studied further. In the presence of enalapril (1 mg/kg), although nepicastat at 60 mg/kg initially produced a greater and longer antihypertensive effect than those induced by the compound at 15 or 30 mg/kg, no greater effect was observed on day 8 through day 30. Thus, the potentiation was not related to the doses of nepicastat tested (15, 30 and 60 mg/kg). The group that received nepicastat 15 mg/kg and E1 exhibited low average mean blood pressure with a large standard error (two rats showed greater antihypertensive responses than the rest).

Nepicastat at 3 and 10 mg/kg, did not consistently affect heart rate (HR) in the 30 day studies. The groups treated with nepicastat at 100 mg/kg, however, tended to exhibit lower HR than the vehicle control group, at least in the first few hours after dosing. Although enalapril at 1 mg/kg did not affect HR, the compound at 10 mg/kg tended to induce a transient small tachycardia within 2 hr after dosing. In Series III, none of the treatments, i.e., enalapril (1 mg/kg), nepicastat (30 mg/kg) or the combination, consistently affected HR. In Series IV, the groups treated with nepicastat (15, 30 and 60 mg/kg) and enalapril (1 mg/kg) tended to exhibit lower HR than the group treated with enalapril (1 mg/kg) alone.

Throughout the study, none of the drug treatments showed a significant effect on motor activity (MA).

Nepicastat at 3-100 mg/kg did not affect the cardiac hypertrophy observed in SHRs ($p>0.05$). Enalapril (10 mg/kg) significantly reduced left ventricular mass in Series II, but not in Series I. In Series III, enalapril at 1 mg/kg did not regress the hypertrophy, but the co-administration of enalapril (1 mg/kg) and nepicastat (30 mg/kg) significantly decreased the left ventricular mass of the SHRs ($p<0.01$). In Series IV, however, effects of co-administration of enalapril (1 mg/kg) and nepicastat at 15, 30 and 60 mg/kg on the left ventricular mass were not different from enalapril alone ($p>0.05$).

Compared to that treated with vehicle, treatment of the SHRs with nepicastat at 3 and 10 mg/kg did not have any effect on body weights in SHRs ($p>0.05$). Treatment with the compound at 30 and 100 mg/kg, however, induced greater increases in body weight ($p<0.05$).

In comparison, enalapril at 10 mg/kg significantly decreased ($p<0.05$) or had no effect on the body weights of the rat. Although treatment with enalapril at 1 mg/kg slightly decreased body weight, co-administration of enalapril (1 mg/kg) and nepicastat (30 and 60 mg/kg) slightly increased the body weights of the rat.

The pre-dose body weights of the rats treated with vehicle, enalapril, and nepicastat at 3 and 10 mg/kg were 387±11, 415±12, 407±4, and 415±12 g, respectively.

The pre-dose body weights of the rats treated with vehicle, enalapril, and nepicastat at 30 and 100 mg/kg were 399±10, 389±6, 389±9, and 401±10 g, respectively.

The pre-dose body weights of the rats treated with vehicle, enalapril, and nepicastat at 30 mg/kg without and with enalapril were 365±9, 371±8, 361±7, and 369±7 g, respectively.

The pre-dose body weights of the rats treated with enalapril alone and co-administrations of nepicastat at 15, 30, and 60 mg/kg were 357±6, 363±6, 347±8, and 346±8 g, respectively.

Four deaths were observed in the 4 series of 30-day treatments. The causes of these deaths were undetermined, but it appeared unlikely that these deaths were related to the treatment of nepicastat.

The effects of 30-day chronic oral administration of nepicastat on blood pressure, heart rate, motor activity and left ventricular mass were evaluated in four series of experiments in spontaneously hypertensive rats (SHRs) with radio-telemetry implants. Daily treatment of nepicastat at 3 and 10 mg/kg (n=6) did not affect blood pressure. Nepicastat at 30 mg/kg (n=6) induced a peak antihypertensive effect of −20 mmHg on day 3 ($p<0.01$). The antihypertensive effect was modest but were detected throughout the study. At 100 mg/kg, nepicastat (n=5) induced a greater antihypertensive effect. The effect was gradual and reached its peak of −42 mmHg on day 3 ($p<0.01$). Comparable magnitudes of antihypertensive effects were observed for the rest of the study. In comparison, the angiotensin converting enzyme inhibitor enalapril (10 mg/kg, n=6) induced an antihypertensive effect of −20 to −30 mmHg throughout the study. Although mono-administration of enalapril (1 mg/kg) did not induce significant antihypertensive effects, the co-administration with nepicastat (30 mg/kg; n=6) induced a greater and long-lasting antihypertensive effect ($p<0.01$). The potentiation was observed throughout the 30-day study. The potentiation of the antihypertensive effects of nepicastat by enalapril (1 mg/kg) was also seen at doses of 15, 30, and 60 mg/kg, although these effects were not dose dependent.

In groups treated with nepicastat at 3-10 mg/kg or enalapril at 1 mg/kg, no significant effects on heart rate were observed. The groups that received nepicastat at 30 or 100 mg/kg, however, exhibited slight bradycardia during the awake hours of the rat. In contrast, enalapril at 10 mg/kg induced a transient tachycardia. Co-administration of nepicastat (15, 30, and 60 mg/kg) and enalapril (1 mg/kg) tended to exhibit slower heart rate than enalapril (1 mg/kg) alone. In any of the treatment groups, no significant effect on motor activity was detected.

Treatment with nepicastat at 30 (n=6) and 100 (n=5) mg/kg did not have significant effects on the left ventricular hypertrophy observed in SHRs. Although enalapril (1 mg/kg, n=8) or nepicastat (30 mg/kg, n=7) alone did not regress the hypertrophy, the co-administration of the two compounds (n=8) significantly decreased the left ventricular mass of the SHRs. The effect of co-administration on left ventricular mass, however, was not dose related to nepicastat (15, 30 and 60 mg/kg) and was not statistically different from that of enalapril (1 mg/kg) alone.

In the four series of experiments, four deaths occurred during the course of the 30 day treatments. Three rats were found in groups treated with nepicastat and one with vehicle. The causes of death were undetermined, but appeared unrelated to the treatment of nepicastat.

Nepicastat significantly reduced blood pressure in SHRs over the 30-day period at 30 and 100 mg/kg without causing any reflex tachycardia. Co-administration of nepicastat (30 mg/kg) with a non-antihypertensive dose of enalapril (1 mg/kg) had a greater anti-hypertensive effect and a greater effect on regression of hypertrophy in SHRs than nepicastat treatment alone. These effects, however, were not dose related to nepicastat (15, 30 and 60 mg/kg).

Example 31

A study was conducted to evaluate the effects of nepicastat on responses to autonomic agents in anesthetized, instrumented dogs.

Beagle dogs were administered single intraduodenal doses of 0 (vehicle) or 60 mg/kg of nepicastat through an intraduodenal cannula. The vehicle-control group consisted of 1 male and 1 female, and the nepicastat-treatment group consisted of 2 males and 2 females. Each animal was surgically instrumented while anesthetized with isoflurane gas. Before dosing with test formulation, the average blood pressure responses to intravenous doses of autonomic agents, norepinephrine (3 µg/kg), isoproterenol (0.3 µg/kg), and acetylcholine (10 µg/kg), were evaluated. A single bolus dose of test formulation was then administered to each animal and the blood pressure responses to the autonomic agents were evaluated approximately 1, 2, and 3 hours after dosing. At the completion of the experiment, each dog was euthanatized and removed from the study.

The dog was selected because it is commonly used to evaluate the effects of test compounds on hemodynamic parameters. Beagle dogs were obtained from Marshall Farms, Inc., North Rose, N.Y. Each dog was identified uniquely by an ear tattoo applied by the vendor. The animals were acclimated to laboratory conditions at least 3 weeks before dosing. During the acclimation period, the general condition of each animal was evaluated and those considered healthy were used. The dogs were randomly assigned to treatment groups; males were assigned odd numbers and females were assigned even numbers.

After assignment to the study, the dogs were housed individually in stainless steel cages identified with the study number, animal number, and tattoo number. The room housing the dogs was environmentally controlled. The cages were cleaned daily and the animals were transferred into sanitized cages every other week. Purina Certified Canine Chow® was offered once daily and water was provided ad libitum.

On the day of treatment, the dogs were approximately 14 to 16 months old. Males weighed 10.3 to 12.9 kg and females weighed 8.5 to 11.2 kg.

At the time of dosing, a 60-mg/ml suspension was prepared by mixing nepicastat powder with vehicle. The constituted 60-mg/ml nepicastat formulation retained potency for the duration of use. On each day of dosing, aqueous solutions of norepinephrine (60 µg/ml), isoproterenol (6 µg/ml), and acetylcholine (200 µg/ml) were prepared in sterile water.

A vehicle-control group of 1 male and 1 female were administered 1 ml/kg of vehicle and a nepicastat-treatment group of 2 males and 2 females were administered 1 ml/kg of a 60 mg/ml nepicastat solution. The total dose of nepicastat administered to each animal was 60 mg/kg.

Dose selection was based on data from two studies with nepicastat. In an acute toxicity study in dogs, a single oral dose of 400 mg/kg resulted in transient clinical signs of toxicity. In a 1-month study, doses of 5, 20, or 80 mg/kg were administered to dogs orally once daily. Clinical signs of toxicity were present at 80 mg/kg/day.

A single intraduodenal dose of vehicle or nepicastat formulation was administered directly into the duodenum through an intraduodenal cannula. The intraduodenal route was selected because the oral route is a proposed clinical route of administration of nepicastat. Dose volumes were calculated on the basis of individual body weights recorded before dosing (data not tabulated in this report). At the end of each experiment, the dog being evaluated was euthanatized by an overdose of sodium pentobarbital (300 mg/kg, IV) and removed from the study.

The dogs were surgically instrumented according to procedures described in the protocol. Food was withheld from the animals overnight before surgical instrumentation. Each animal being evaluated was initially anesthetized by injecting (IV) a mixture of ketamine (10 mg/kg) and diazepam (0.5 mg/kg). Each animal was placed on a surgical table on top of a circulating warm-water pad to maintain body temperature and mechanically ventilated throughout the experiment. A surgical plane of anesthesia was maintained with isoflurane gas (1.5% to 2% of tidal volume delivered in oxygen at a flow rate of approximately 1.5 L/minute). Rectal body temperature was monitored only for use in measuring blood gas levels and the data are not presented in this report. External needle electrodes were placed subcutaneously to monitor a standard limb lead II electrocardiogram (ECG) for assessing anesthesia.

The left femoral vein was cannulated and the tip of the polyethylene tubing was advanced into the vena cava for administration of autonomic agents. The left femoral artery was cannulated using a polyethylene tube filled with 50 U/ml of heparin-saline solution. The tip of the arterial cannula was advanced into the thoracic aorta and coupled to an external pressure transducer and systolic and diastolic aortic pressure were recorded. Arterial blood samples were withdrawn from the arterial cannula for blood pH, $PCO_2$, and $PO_2$ analyses.

A midline laparotomy was performed and the duodenum was isolated just caudal to the pyloric sphincter. A needle was inserted into the duodenum and the tip of a saline-filled cannula was advanced through the needle and into the lumen for test formulation administration. The needle was withdrawn from the incision site, the cannula was anchored into position, the cannula's stopcock was exteriorized outside of the abdomen, and the skin of the abdominal incision was reapposed.

Following surgical instrumentation, ventilatory adjustments were made, if necessary, to bring arterial blood pH and $PCO_2$ levels within approximately normal physiological ranges (pH=7.43 to 7.50 and $PCO_2$=22 to 27 mmHg).

The autonomic agents, norepinephrine (3 µg/kg), isoproterenol (0.3 µg/kg), and acetylcholine (10 µg/kg), were administered intravenously by bolus injection (over approximately 15 seconds) using the femoral vein cannula with approximately 10 minutes between each dose. Following each administration of an agent, the cannula was flushed with 3 ml of water. Administration of the agents was repeated approximately 20 minutes after the first administration of acetylcholine.

Approximately 30 minutes after the second administration of acetylcholine, each animal was dosed with vehicle or nepicastat. The dose volume was 1 ml/kg given as a bolus directly into the duodenum using the intraduodenal cannula. Immediately after dosing, the intraduodenal cannula was flushed with 3 ml of vehicle solution. Approximately 50, 110, and 170 minutes after dosing, administration of the autonomic agents was repeated with approximately 10 minutes between administration of each agent.

Aortic blood pressure, heart rate, and ECG parameters were continuously recorded directly on a polygraph recorder. The blood pH, $PCO_2$, and $PO_2$ values from the blood gas analyzer were manually recorded onto the polygraph chart at the approximate time at which the blood samples were withdrawn. Heart rate, ECG, and blood gas parameters were used only for assessing the level of anesthesia and the stability of the animal preparation; these data are not presented in this report.

Systolic, diastolic, and mean aortic blood pressures were evaluated just before administration (baseline) and at the time of peak response to each agent (maximum change from baseline). Systolic, diastolic, and mean aortic blood pressures, and blood pH, $PCO_2$, and $PO_2$ were evaluated before dosing and approximately 50, 110, and 170 minutes after dosing with test formulation.

The responses to norepinephrine were characterized by evaluating the mean aortic blood pressure just before and at the time of peak pressure increase for each norepinephrine administration. The responses to isoproterenol and acetylcholine were characterized by evaluating the diastolic aortic blood pressure just before and at the time of peak pressure decrease for each isoproterenol and acetylcholine administration.

At the end of the experiment, each dog was euthanatized by an overdose of sodium pentobarbital (approximately 300 mg/kg, IV) and removed from the study. No treatment-related differences between predose and postdose responses to norepinephrine were present. In vehicle-control dogs, the postdose responses to norepinephrine were of lesser magnitude than the predose responses; this was considered incidental. No treatment-related differences between predose and postdose responses to isoproterenol were present. No treatment-related differences between predose and postdose responses to acetylcholine were present.

Surgically instrumented, anesthetized beagle dogs were administered a single intraduodenal dose of 60 mg/kg of nepicastat. Blood pressure responses to intravenous doses of autonomic agents (norepinephrine, isoproterenol, and acetylcholine) were evaluated before dosing and approximately 1, 2, and 3 hours after dosing. No treatment-related differences between predose and postdose responses to autonomic agents were present.

Example 32

The effects of acute intraperitoneal administration of nepicastat, a DBH inhibitor (DBHI), on locomotor activity in mice. It has been suggested that compounds of this class have effects on locomotor activity.

Adult male CD-1 (ICR) mice (30-40 g on study day) were housed in groups of eight under a normal light/dark cycle with lights on between 0900 hr and 2100 hr. Food and water were allowed ad libitum. All animals were naive to drug treatment and behavioral testing. Each animal was only used once.

Locomotor activity was monitored in an automated 14 station activity monitoring system (San Diego Instrument Co.). Each station consisted of a clear perspex cage (25 cm×45 cm×20 cm; w×l×h) placed within a metal frame containing 3 photoemmitors and 3 photodetectors spaced equally along the length of the wall. The bottom of each cage was lightly covered in clean cedar bedding.

The mice were placed in the testing room at least 1 hr prior to testing. The mice were placed individually into one of the activity cages and allowed to explore for 30 min. Following this habituation period, the mice were dosed intraperitoneally with either nepicastat (10, 30 and 100 mg/kg), SKF-102698 (30 and 100 mg/kg), cocaine (30 mg/kg) or vehicle and returned immediately to same cage. Following a 60 minute pre-treatment period, motor activity was monitored for 180 minutes. Activity counts and ambulations (defined as a break of 2 consecutive photobeams) for each animal were recorded every 30 minutes.

A repeated measures two-way analysis of variance (ANOVA) was performed using the overall ranked data (nonparametric technique) to test for the overall effects of treatment, time interval and treatment by time interval interaction. At each time interval, a one-way ANOVA was performed to see at which of the intervals, in any, treatment effects existed. Pairwise comparisons were then performed at each time interval using Dunn's procedure and Fisher's LSD strategy to adjust for the problem of multiple comparisons.

For nepicastat, the dose range was 3-100 mg/kg and was dissolved in $dH_2O$ and sonicated. For SKF-102698, the dose range was 30-100 mg/kg. For cocaine hydrochloride, the dose was 30 mg/kg. Compounds were administered in a volume of 1 ml/100 g. All doses reported are represented as the free base, except for cocaine in which the salt weight was used.

In the overall model, there was a significant effect for both treatment and time (both $p<0.01$) while the treatment by time interaction was not significant. The analysis at each time point revealed that there were significant overall treatment effects at time intervals 1-4 (i.e., the first 120 minutes of testing; all $p<0.01$) while no overall significant treatment effect was detected at time intervals 5 and 6 (i.e., the last 60 minutes of testing).

When comparing the cocaine to the vehicle group with respect to both activity counts and ambulations, there was a significant overall effects for treatment and time (both $p<0.01$) while the treatment by time interaction was not significant. The analysis at each time interval revealed the cocaine group had significantly greater total activity counts and a significantly greater number of ambulations at time intervals 1-4, but not 5 and 6 (all $p<0.05$).

In contrast, there were no significant differences in either the total activity counts or the ambulations for any of the nepicastat-treated groups or the SKF-102698-treated groups compared to vehicle control at any time interval.

Cocaine was effectively demonstrated as a locomotor stimulant at the dose of 30 mg/kg. In contrast, acute administration of nepicastat at doses of 3, 10, 30 or 100 mg/kg did not cause any significant change in total activity or the ambulations at any time interval, as compared to vehicle control. Similarly, SKF-102698 at doses of 30 and 100 mg/kg had no significant effects on total activity or ambulations at any time interval examined. These data suggest that these DBHI are devoid of motoric actions in mice.

Example 33

Acute dosing with the dopamine-β-hydroxylase inhibitor nepicastat has been shown to inhibit the enzyme in the mesenteric artery and left ventricle in spontaneously hypertensive rats. Changes in norepinephrine and dopamine levels in the spontaneous hypertensive rat brain cortex and mesenteric artery after 7 and 25 days of oral administration of 1 mg/kg or 10 mg/kg nepicastat were examined.

Nepicastat at 1 and 10 mg/kg was prepared in terms of the free base. The weighings were dissolved in vehicle ($dH_2O$) to yield oral doses that could be administered in a volume of 10.0 ml/kg.

Male spontaneous hypertensive rats (SHRs), 16-17 weeks old at the onset of the study, were used. Animals were allowed food and water ad libitum. Animals were randomly assigned to one of the following treatment groups: oral administration of nepicastat at 10 mg/kg, 1 mg/kg, or a vehicle group of deionized water at 10 ml/kg. Rats were dosed orally once a day for 7 or 25 days with vehicle, 1 mg/kg or 10 mg/kg nepicastat (n=8) except for day 25, where n=9. On day 7, four hours after compound administration, animals were anesthetized with halothane, decapitated and the cortex and mesenteric artery were harvested, weighed, and analyzed from 24 rats (n=8/treatment group). The remaining 31 rats continued receiving oral administration with one of the three treatments for the following 18 days. At 4 hours after the last treatment the mesenteric artery and cortex from this group were harvested, weighed, and analyzed for catecholamine levels.

The animals sacrificed on day 25 were also used for blood pressure measurements. The last blood pressure measurement was made on day 22.

Statistically, the three treatments were compared at each time period (7 or 25 days) using a non-parametric one-way analysis of variance (ANOVA). Pairwise comparisons of each treatment with control were performed using Fisher's LSD strategy on the means, adjusted for differences in sample size, to control the experiment-wise error rate. Each variable was analyzed separately. For FIGS. 6-11, *, $p<0.05$ and **, $P<0.01$.

Figure 6:
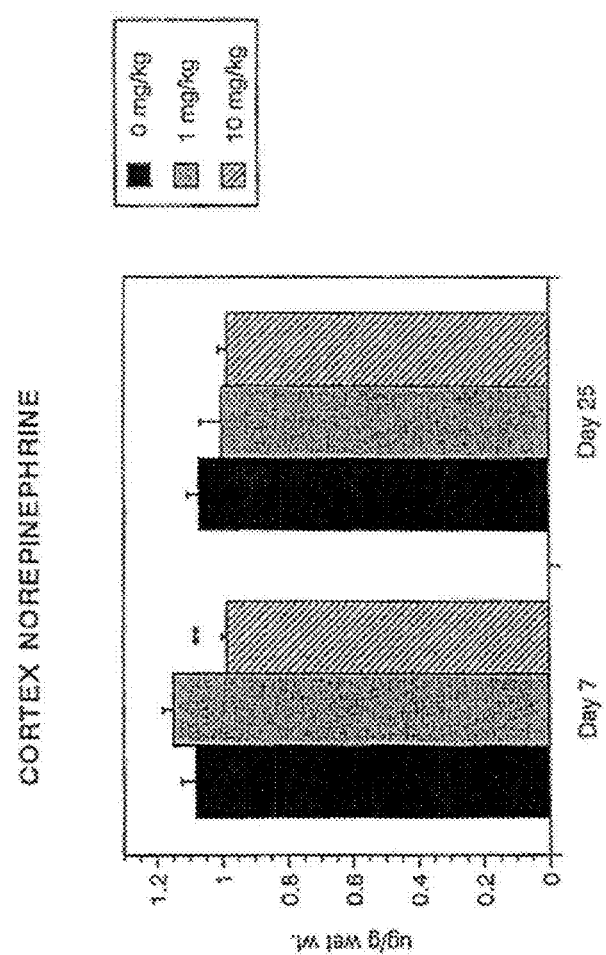
FIG. 6 shows the norepinephrine levels in the cortex in SHRs dosed with vehicle or varying doses of nepicastat.
Figure 7:
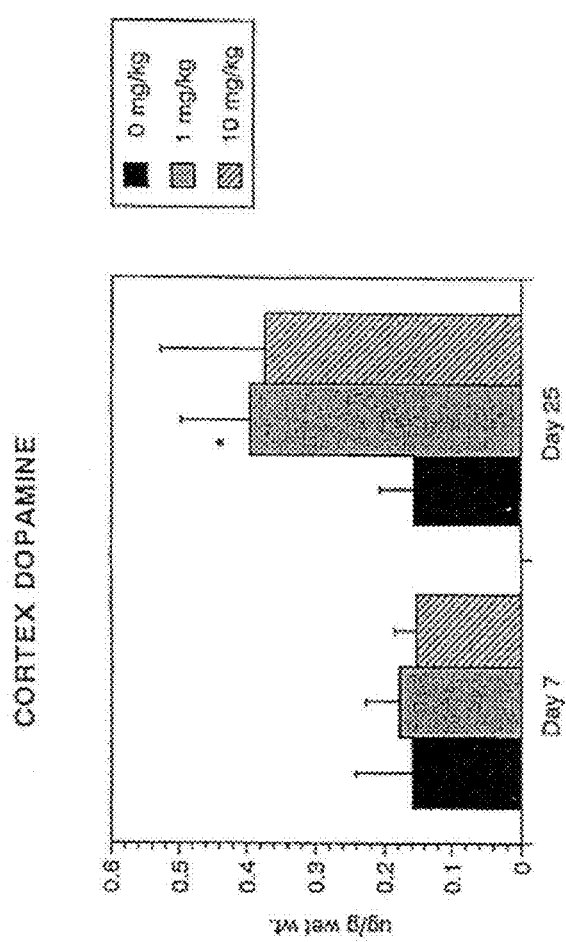
FIG. 7 shows the dopamine levels in the cortex in SHRs dosed with vehicle or varying doses of nepicastat.
Figure 8:
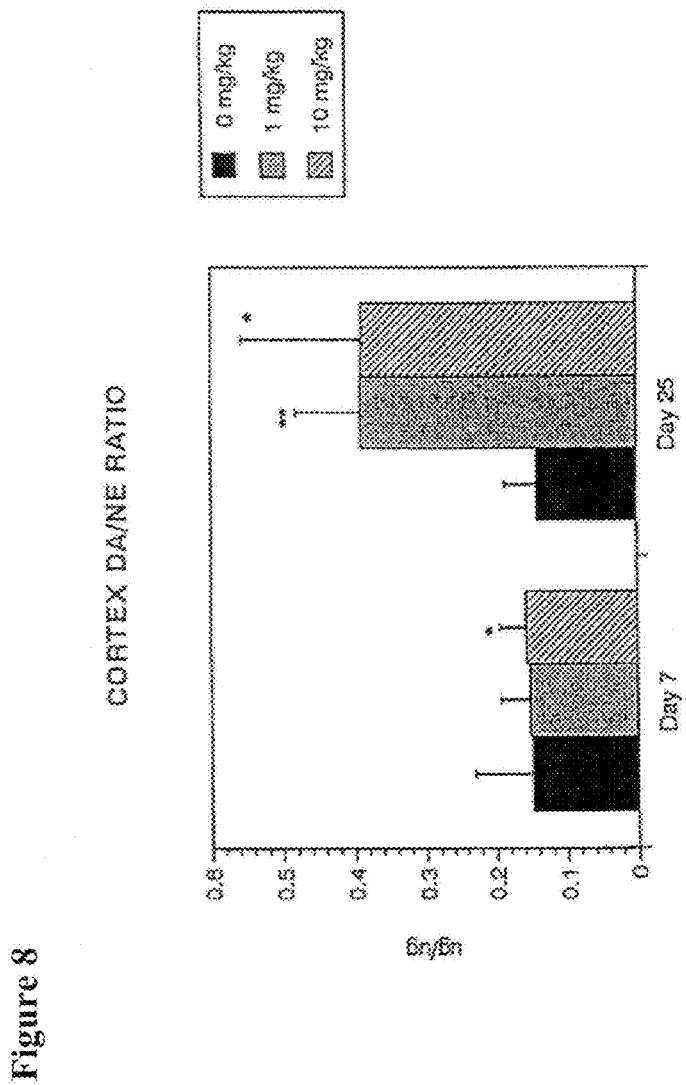
FIG. 8 shows the dopamine/norepinephrine ratio in the cortex in SHRs dosed with vehicle or varying doses of nepicastat.

In the cerebral cortex, after seven days of treatment, the 10 mg/kg dose group had significantly ($p<0.1$) lower norepinephrine levels and a significantly ($p<0.05$) higher dopamine/norepinephrine ratio compared to the vehicle group. There were no significant ($p>0.05$) differences in dopamine levels compared to vehicle in either of the two treatment groups (1 or 10 mg/kg nepicastat), or in the norepinephrine levels or the dopamine/norepinephrine ratio of the 1 mg/kg nepicastat dose group, after seven days of treatment (FIGS. 6-8). There was a slight significant ($p<0.05$) increase in the cortex dopamine/norepinephrine ratio at day 7 with the 10 mg/kg nepicastat dose.

After 25 days of treatment, cortex levels of dopamine in the 1 mg/kg nepicastat dose group were significantly ($p<0.05$) higher compared to the vehicle group. The cortex dopamine/norepinephrine ratio in this group was also significantly ($p<0.01$) greater than the vehicle ratio. The ratio of the 10 mg/kg nepicastat dose group was significantly greater ($p<0.05$) compared to vehicle. Norepinephrine levels in either dose group were not significantly (p.>0.05) different than control, nor were the dopamine levels in the 10 mg/kg dose group (FIGS. 6-8).

Figure 9:
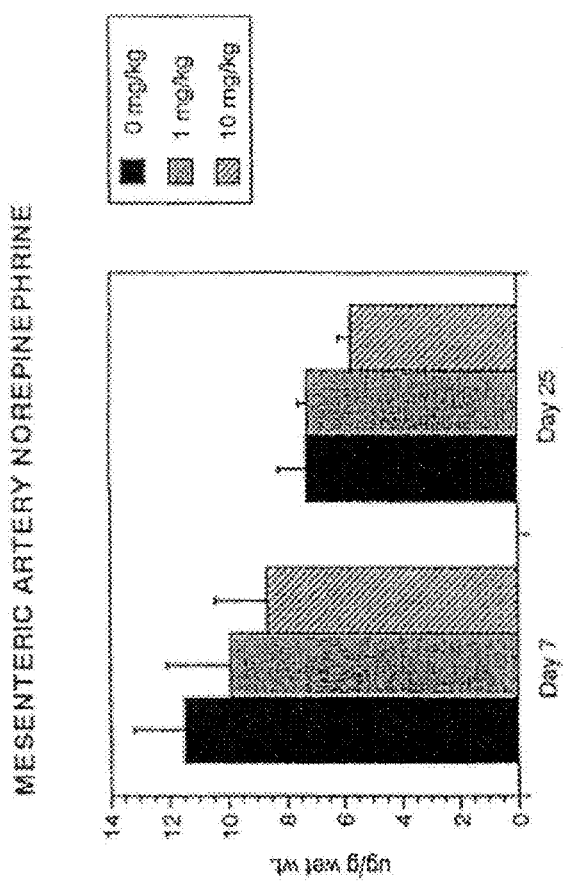
FIG. 9 shows the norepinephrine levels in the mesenteric artery in SHRs dosed with vehicle or varying doses of nepicastat.
Figure 10:
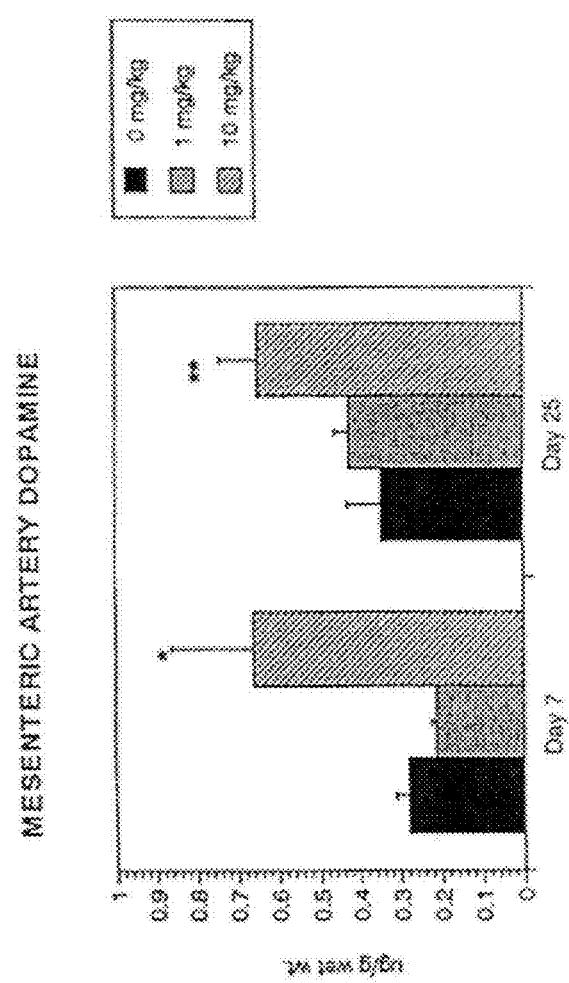
FIG. 10 shows the dopamine levels in the mesenteric artery in SHRs dosed with vehicle or varying doses of nepicastat.
Figure 11:
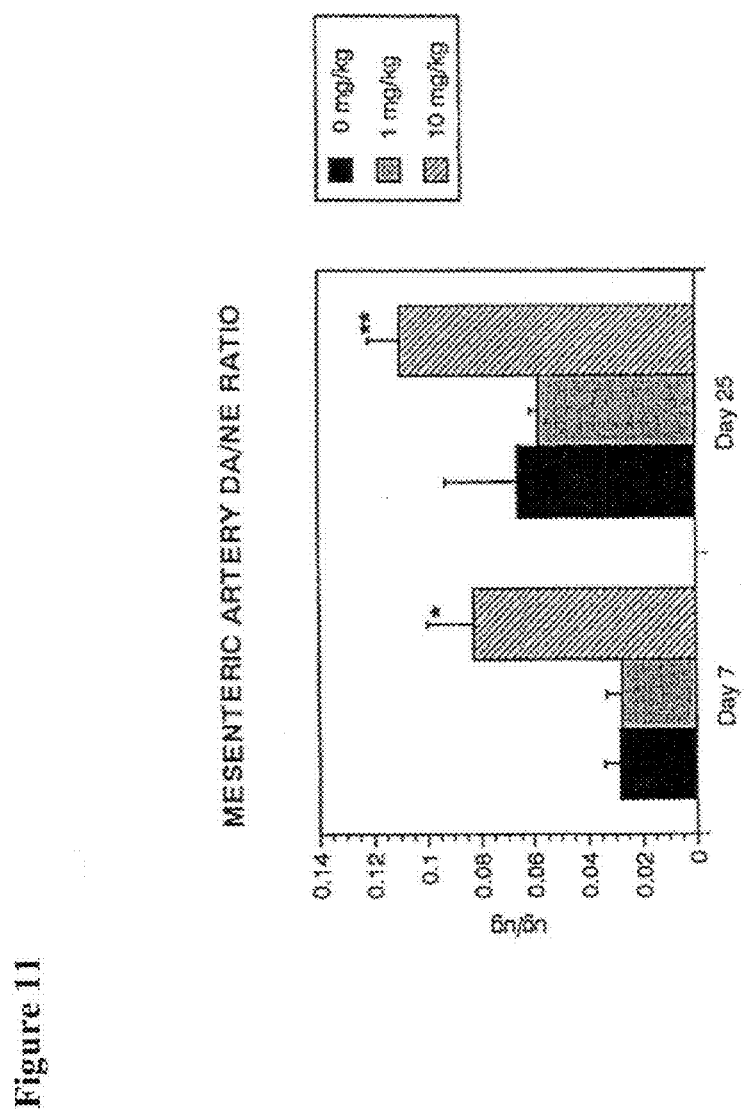
FIG. 11 shows the dopamine/norepinephrine ratio in the mesenteric artery in SHRs dosed with vehicle or varying doses of nepicastat.

In the mesenteric artery, after both 7 days ($p<0.05$) and 25 days ($p<0.01$) of dosing, the 10 mg/kg dose group had significantly higher dopamine levels and dopamine/norepinephrine ratios compared to the vehicle group, but there were no differences in norepinephrine levels. None of the parameters measured were significantly ($p<0.05$) different than control in the 1 mg/kg nepicastat dose group (FIGS. 9-11).

Nepicastat, administered orally for 7 and 25 days, significantly ($p<0.05$) inhibited dopamine-β-hydroxylase in the cortex and mesenteric artery of spontaneously hypertensive rats (SHRs). Greater inhibition was seen with administration of 10 mg/kg nepicastat compared to 1 mg/kg, therefore the effects observed were dose dependent.

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

What is claimed is:

1. A method of treating a patient suffering from or susceptible to at least one symptom of abuse of, dependence on, or withdrawal from at least one substance, the method comprising administering to the patient a therapeutically effective amount of nepicastat or a pharmaceutically acceptable salt thereof,
   wherein the at least one substance is alcohol, with the proviso that the at least one substance is not both cocaine and alcohol.

2. The method of claim 1, wherein the method of treatment further comprises co-administering a therapeutically effective amount of at least one other agent selected from the group consisting of a selective serotonin reuptake inhibitor, a serotonin-norepinephrine reuptake inhibitor, a norepinephrine reuptake inhibitor, a norepinephrine-dopamine reuptake inhibitor, a serotonin 5-HT1A antagonist, a dopamine beta-hydroxylase inhibitor, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, and a serotonin 5HT2 antagonist.

3. The method of claim 2, wherein the therapeutically effective amount of least one other agent is selected from the group consisting of benzodiazepine, levodopa, carisprodol, modafenil, gamma-butyrolactone, and gamma-hydroxybutyrate.

4. The method of claim 2, wherein the at least one other agent is disulfiram.

5. A method of treating at least one phase of substance dependence on at least one substance in a patient, wherein the at least one phase of substance dependence is selected from acquisition, maintenance, extinction, and relapse, comprising administering to the patient a therapeutically effective amount of nepicastat or a pharmaceutically acceptable salt thereof,
   wherein the at least one substance is alcohol, with the proviso that the at least one substance is not both cocaine and alcohol.

6. The method of claim 5, wherein the nepicastat or the pharmaceutically acceptable salt thereof inhibits the development of the acquisition phase in the patient.

7. The method of claim 5, wherein the nepicastat or the pharmaceutically acceptable salt thereof promotes the development of the extinction phase in the patient.

8. The method of claim 1, wherein the patient is a woman.

9. The method of claim 5, wherein the method of treatment further comprises co-administering a therapeutically effective amount of at least one other agent selected from the group consisting of a selective serotonin reuptake inhibitor, a serotonin-norepinephrine reuptake inhibitor, a norepinephrine reuptake inhibitor, a norepinephrine-dopamine reuptake inhibitor, a serotonin 5-HT1A antagonist, a dopamine beta-hydroxylase inhibitor, an atypical antidepressant/antipsychotic, a tricyclic, an anticonvulsant, a glutamate antagonist, a gamma-aminobutyric acid (GABA) agonist, a GABA metabolism enzyme inhibitor, a GABA synthesis activator, a partial dopamine D2 agonist, a dopamine metabolism enzyme inhibitor, a catechol-O-methyl-transferase inhibitor, an opioid receptor antagonist, a mood stabilizer, a direct or indirect dopamine agonist, a partial 5HT1 agonist, and a serotonin 5HT2 antagonist.

* * * * *